United States Patent [19]

Allen et al.

[11] Patent Number: 5,330,987

[45] Date of Patent: Jul. 19, 1994

[54] SUBSTITUTED PYRIDOPYRIMIDINONES AND RELATED HETEROCYCLES AS ANGIOTENSIN II ANTAGONISTS

[75] Inventors: Eric E. Allen, Somerset; Prasun K. Chakravarty, Edison; Stephen E. de Laszlo, Atlantic Highlands; William J. Greenlee, Teaneck; Arthur A. Patchett; Thomas F. Walsh, both of Westfield, all of N.J.

[73] Assignee: Merck & Co., Inc., Rahway, N.J.

[21] Appl. No.: 894,036

[22] Filed: Jun. 4, 1992

Related U.S. Application Data

[63] Continuation-in-part of Ser. No. 590,981, Oct. 1, 1990, abandoned.

[51] Int. Cl.$^5$ .................. A61K 31/505; C07D 403/12; C07D 487/04
[52] U.S. Cl. ...................................... 514/258; 544/279; 544/117; 544/61; 544/58.2; 544/244; 544/80; 544/180; 544/212; 544/2; 544/96; 514/81; 514/222.5; 514/232.5; 514/234.2; 514/228.8; 514/228.5; 514/241; 514/245; 514/253
[58] Field of Search ............ 514/258, 81, 222.5, 514/232.5, 234.2, 228.8, 228.5, 241, 245, 253; 544/279, 117, 61, 58.2, 244, 80, 180, 212, 2, 96

[56] References Cited

U.S. PATENT DOCUMENTS 3,931,183  1/1976  Hardtmann ............... 260/256.4
3,936,453  2/1976  Hardtmann ............... 260/256.4
4,880,804  11/1989 Carini et al. ............. 514/234.5

FOREIGN PATENT DOCUMENTS

58696/90  1/1991  Australia .
253310    1/1988  European Pat. Off. .
407342    1/1991  European Pat. Off. .

Primary Examiner—John M. Ford
Attorney, Agent, or Firm—Robert J. North; Melvin Winokur

[57] ABSTRACT

Novel substituted pyridopyrimidinones of formula (I), which are useful as angiotensin II antagonists, are disclosed.

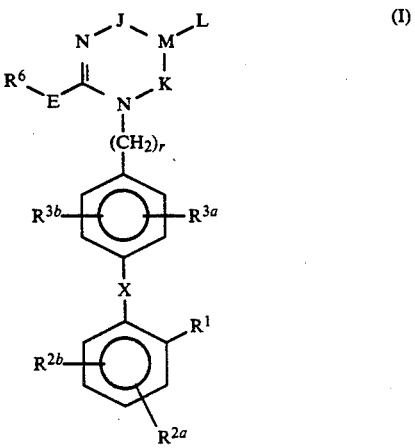

15 Claims, No Drawings

SUBSTITUTED PYRIDOPYRIMIDINONES AND RELATED HETEROCYCLES AS ANGIOTENSIN II ANTAGONISTS

CROSS REFERENCE TO RELATED APPLICATIONS

The instant application is a continuation-in-part application of U.S. Ser. No. 590,981, filed Oct. 1, 1990, now abandoned.

INTRODUCTION OF THE INVENTION

This invention relates to novel substituted pyridopyrimidinone and related heterocyclic compounds which are useful as angiotensin II antagonists in the treatment of elevated blood pressure and congestive heart failure. Thus, the substituted pyridopyrimidinone compounds of the invention are useful as antihypertensives.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. *Clin. Exp, Hypertens.* A4, 27-46 (1982); D. H. P. Streeten and G. H. Anderson, Jr.—*Handbook of Hypertension, Clinical Pharmacology of Antihypertensiye Drugs*, ed. A. E. Doyle, Vol. 5, pp. 246-271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324 ; 4,340,598; 4,576,958; 4,582,847; and 4,880,804; in European Patent Applications 028,834; 245,637; 253,310; 291,969; 323,841; and 324,377; and in articles by A. T. Chiu, et. al. [*Eur. J. Pharm. Exp. Therap,* 157, 13-21 (1988)] and by P. C. Wong, et al, [*J. Pharm. Exp. Therap,* 247, 1-7(1988), *Hypertension,* 13, 489-497 (1989)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxlic acid and analogs thereof as antihypertensive agents.

DETAILED DESCRIPTION OF THE INVENTION

This invention relates to novel substituted pyridopyrimidinone and related heterocyclic compounds which are useful as angiotensin II antagonists, as antihypertensives, in the treatment of congestive heart failure, and in the treatment of elevated intraocular pressure. The compounds of this invention have the general formula (I):

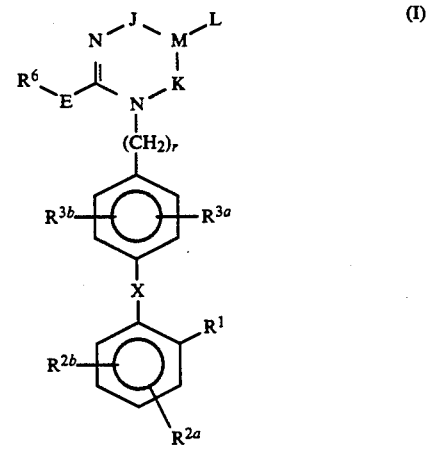

wherein:

M is
  a C atom;
L is
  C or N when connected to K or J to form a ring as defined below;
J is
  —C(=Y)— where Y is O or $NR^{21}$ and K and L are connected together to form a 6 membered aromatic ring containing one N atom that is not at K and five C atoms which may be substituted at the carbon atoms with $R^{8a}$ and $R^{8b}$;
K is
  —C(=Y)— where Y is O or $NR^{21}$ and J and L are connected together to form a 6 membered aromatic ring containing one N atom that is not at J and five C atoms which may be substituted at the carbon atoms with $R^{8a}$ and $R^{8b}$ provided that only one of J or K is —C(=Y)—;
$R^1$ is
  (a) —$CO_2R^4$,
  (b) —$SO_3R^5$,
  (c) —$NHSO_2CF_3$,
  (d) —$PO(OR^5)_2$,
  (e) —$SO_2$—NH—$R^9$,
  (f) —$CONHOR^5$,

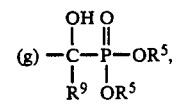

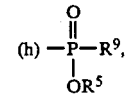

(i) —$SO_2NH$-heteroaryl as defined below,
  (j) —$CH_2SO_2NH$-heteroaryl as defined below,
  (k) —$SO_2NH$—CO—$R^{22}$,
  (l) —$CH_2SO_2NH$—CO—$R^{22}$,
  (m) —$CONH$—$SO_2R^{22}$,
  (n) —$CH_2CONH$—$SO_2R^{22}$,
  (o) —$NHSO_2NHCO$—$R^{22}$,
  (p) —$NHCONHSO_2$—$R^{22}$,

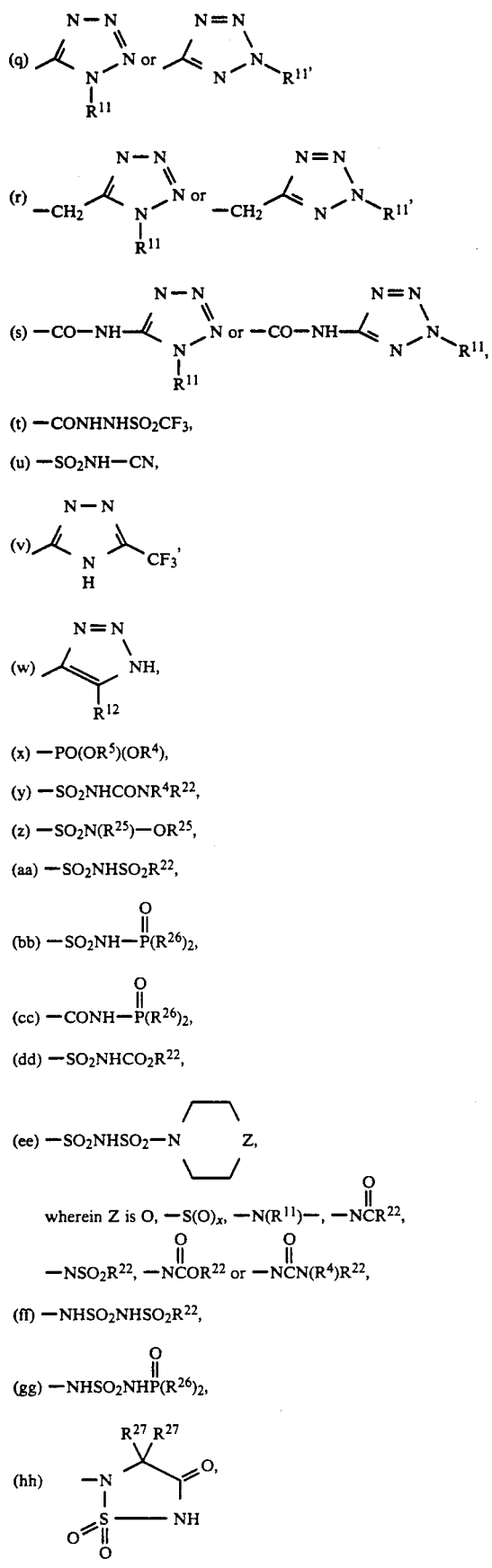
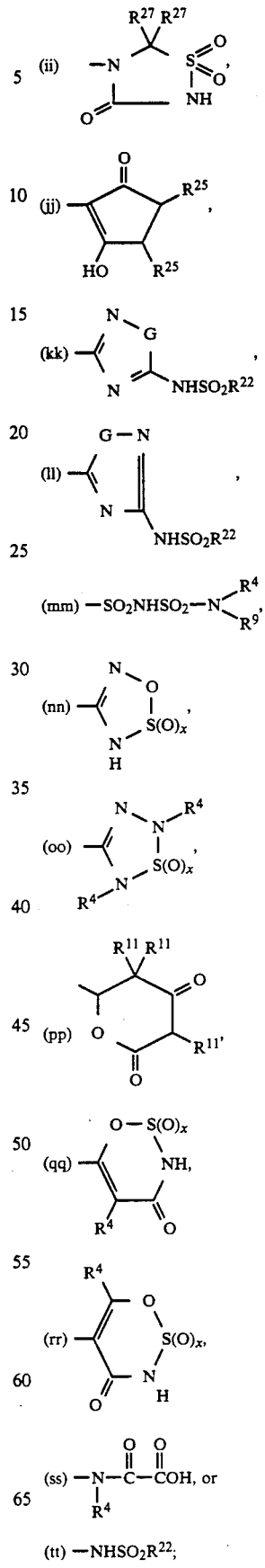

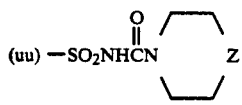

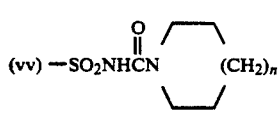

n = 0,1,2.

wherein G is O or S;
wherein heteroaryl is an unsubstituted, monosubstituted or disubstituted five or six membered aromatic ring which can optionally contain from 1 to 3 heteroatoms selected from the group consisting of O, N or S such as pyridine, pyrimidine, pyrazine, triazine, furan, thiophene, oxazole, thiazole, imidazole, triazole, thiadiazole, or the like and wherein the substituents are members selected from the group consisting of —OH, —SH, —$C_1$-$C_4$-alkyl, —$C_1$-$C_4$-alkoxy, —$CF_3$, halo (Cl, Br, F, I), —$NO_2$, —$CO_2H$, —$CO_2$—($C_1$-$C_4$-alkyl), —$NH_2$, —NH($C_1$-$C_4$-alkyl) and —N($C_1$-$C_4$-alkyl)$_2$;

$R^{2a}$ and $R^{2b}$ are each independently
 (a) H,
 (b) halogen, (Cl, Br, I, F)
 (c) $NO_2$,
 (d) $NH_2$,
 (e) $C_1$-$C_4$-alkylamino,
 (f) di($C_1$-$C_4$-alkyl)amino
 (g) $SO_2NHR^9$,
 (h) $CF_3$,
 (i) $C_1$-$C_6$-alkyl,
 (j) $C_1$-$C_6$-alkoxy,
 (k) $C_1$-$C_6$-alkyl-S—,
 (l) $C_2$-$C_6$-alkenyl,
 (m) $C_2$-$C_6$-alkynyl;
 (n) aryl as defined below,
 (o) aryl($C_1$-$C_4$-alkyl),
 (p) $C_3$-$C_7$-cycloalkyl;

$R^{3a}$ is
 (a) H,
 (b) halo (Cl, Br, I, F)
 (c) $C_1$-$C_6$-alkyl,
 (d) $C_1$-$C_6$-alkoxy,
 (e) $C_1$-$C_6$-alkoxyalkyl;

$R^{3b}$ is
 (a) H,
 (b) halo (Cl, Br, I, F)
 (c) $NO_2$,
 (d) $C_1$-$C_6$-alkyl,
 (e) $C_1$-$C_6$-acyloxy,
 (f) $C_3$-$C_7$-cycloalkyl,
 (g) $C_1$-$C_6$-alkoxy,
 (h) —$NHSO_2R^4$,
 (i) hydroxy($C_1$-$C_4$-alkyl),
 (j) aryl($C_1$-$C_4$-alkyl),
 (k) $C_1$-$C_4$-alkylthio,
 (l) $C_1$-$C_4$-alkyl sulfinyl,
 (m) $C_1$-$C_4$-alkyl sulfonyl,
 (n) $NH_2$,
 (o) $C_1$-$C_4$-alkylamino,
 (p) di($C_1$-$C_4$-alkyl)amino,
 (q) fluoro-$C_1$-$C_4$-alkyl-,
 (r) —$SO_2$—$NHR^9$,
 (s) aryl as defined below, (t) furyl,
 (u) $CF_3$,
 (v) $C_2$-$C_6$-alkenyl,
 (w) $C_2$-$C_6$-alkynyl;
wherein aryl is phenyl or naphthyl optionally substituted with one or two substituents selected from the group consisting of halogen(Cl, Br, I, F), $N(R^4)_2$, $CO_2R^4$, $C_1$-$C_4$-alkyl, $C_1$-$C_4$-alkoxy, $NO_2$, $CF_3$, $C_1$-$C_4$-alkylthio, OH,

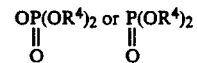

$R^4$ is
 H, aryl as defined above or straight chain or branched $C_1$-$C_6$ alkyl optionally substituted with aryl or heteroaryl as defined above;
$R^{4a}$ is
 aryl as defined above or straight chain or branched $C_1$-$C_6$-alkyl optionally substituted with aryl as defined above
$R^5$ is
 H,

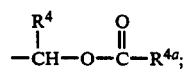

E is
 a single bond, —$NR^{13}(CH_2)_s$—, —$S(O)_x(CH_2)_s$— where x is 0 to 2 and s is 0 to 5, —CH(OH)—, —O—, CO—;
$R^6$ is
 (a) aryl as defined above optionally substituted with 1 or 2 substituents selected from the group consisting of halo (Cl, Br, I, F) —O—$C_1$-$C_4$-alkyl, $C_1$-$C_4$-alkyl, —$NO_2$, —$CF_3$, —$SO_2NR^9R^{10}$, —S—$C_1$-$C_4$-alkyl, —OH, —$NH_2$, $C_3$-$C_7$-cycloalkyl, $C_3$-$C_{10}$-alkenyl;
 (b) straight chain or branched $C_1$-$C_6$-alkyl, $C_2$-$C_5$-alkenyl or $C_2$-$C_5$-alkynyl each of which can be optionally substituted with a substituent selected from the group consisting of aryl as defined above, $C_3$-$C_7$-cycloalkyl, halo (Cl, Br, I, F), $CF_3$, $CF_2CF_3$, —$NH_2$, —NH($C_1$-$C_4$-alkyl), —$OR^4$ —N($C_1$-$C_4$-alkyl)$_2$, —NH—$SO_2R^4$, —$COOR^4$, —$SO_2NHR^9$; or
 (c) heteroaryl,
 (d) $C_3$-$C_7$-cycloalkyl;
 (e) perfluoro-$C_1$-$C_4$-alkyl,
 (f) H;
$R^{8a}$ and $R^{8b}$ are independently
 (a) H, provided they are not both H
 (b) $C_1$-$C_8$-alkyl substituted with a substituent selected from the group consisting of guanidino, —O—$COR^4$, -aryl, -heteroaryl, -tetrazol-5-yl, —$CONHSO_2R^{22}$, —$SO_2NH$-heteroaryl, —$SO_2NHCOR^{22}$, —$PO(OR^4)_2$, —$PO(OR^4)R^9$, —$SO_2NH$—CN, —$NR^{10}COOR^{22}$, morpholino, 4-$R^{22}$-piperazin-1-yl, and 4-$COR^{22}$-piperazin-1-yl;
 (c) —CO-aryl,
 (d) —$C_3$-$C_7$-cycloalkyl,
 (e) —$COOR^4$,
 (f) —$SO_3H$,
 (g) —$NR^4R^{22}$,
 (h) —$NR^4COR^{22}$,
 (i) —$NR^4COOR^{22}$, (j) —SO$_2$NR$^4$R$^9$,
(k) —NO$_2$,
(l) —N(R$^4$)SO$_2$R$^{22}$,
(m) —NR$^4$CONR$^4$R$^{22}$,

(o) -aryl or -heteroaryl as defined above,
(p) —NHSO$_2$CF$_3$,
(q) —SO$_2$NH-heteroaryl,
(r) —SO$_2$NHCOR$^{22}$,
(s) —CONHSO$_2$R$^{22}$,
(t) —PO(OR$^4$)$_2$,
(u) —PO(OR$^4$)R$^4$,
(v) -tetrazol-5-yl,
(w) —CONH(tetrazol-5-yl),
(x) —COR$^4$,
(y) —SO$_2$NHCN
(z) —NR$^4$SO$_2$NR$^4$R$^{22}$,
(aa) —NR$^4$SO$_2$OR$^{22}$,
(bb) —CONR$^4$R$^{22}$,

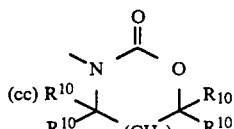

where n = 0 or 1.

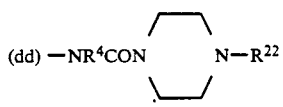

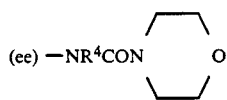

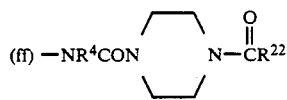

R$^9$ is
H, C$_1$-C$_5$-alkyl, aryl or arylmethyl;
R$^{10}$ is
H, C$_1$-C$_4$-alkyl;
R$^{11}$ is
H, C$_1$-C$_6$-alkyl, C$_1$-C$_4$-alkenyl, C$_1$-C$_4$-alkoxy-C$_1$-C$_6$-alkyl, C$_1$-C$_6$-alkoxycarbonyl, aryl-C$_1$-C$_6$-alkoxycarbonyl, or

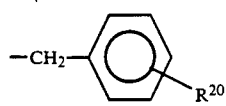

R$^{12}$ is
—CN, —NO$_2$ or —CO$_2$R$^4$;
R$^{13}$ is
H, (C$_1$-C$_4$-alkyl)CO—, C$_1$-C$_6$-alkyl, allyl, C$_3$-C$_6$-cycloalkyl, aryl or arylmethyl;
R$^{14}$ is
H, C$_1$-C$_8$-alkyl, C$_1$-C$_8$-perfluoroalkyl, C$_3$-C$_6$-cycloalkyl, aryl or arylmethyl;
R$^{15}$ is
H, C$_1$-C$_6$-alkyl;
R$^{16}$ is
H, C$_1$-C$_6$-alkyl, C$_3$-C$_6$-cycloalkyl, aryl or arylmethyl;
R$^{17}$ is
—NR$^9$R$^{10}$, —OR$^{10}$, —NHCONH$_2$, —NHCSNH$_2$,

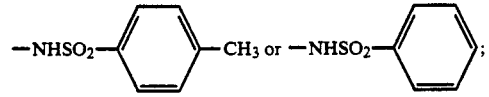

R$^{18}$ and R$^{19}$ are independently C$_1$-C$_4$-alkyl or taken together are —(CH$_2$)$_q$— where q is 2 or 3;
R$^{20}$ is
H, —NO$_2$, —NH$_2$, —OH or —OCH$_3$;
R$^{21}$ is
(a) aryl as defined above,
(b) heteroaryl as defined above,
(c) C$_1$-C$_4$-alkyl optionally substituted with a substituent selected from the group consisting of aryl as defined above, heteroaryl as defined above, —OH, —NH$_2$, —NH(C$_1$-C$_4$-alkyl), —N(C$_1$-C$_4$-alkyl)$_2$, —CO$_2$R$^{4a}$, halo(Cl, Br, F, I), —CF$_3$;
R$^{22}$ is
(a) aryl as defined above,
(b) heteroaryl as defined above,
(c) C$_3$-C$_7$-cycloalkyl,
(d) C$_1$-C$_8$-alkyl optionally substituted with a substituent selected from the group consisting of aryl as defined above, heteroaryl as defined above, —OH, —SH, —C$_1$-C$_4$-alkyl, —O(C$_1$-C$_4$-alkyl), —S(-C$_1$-C$_4$-alkyl), —CF$_3$, halo (Cl, Br, F, I), —NO$_2$, —CO$_2$H, CO$_2$-(C$_1$-C$_4$-alkyl), —NH$_2$, —NH(-C$_1$-C$_4$-alkyl), —N(C$_1$-C$_4$-alkyl)$_2$, —PO$_3$H$_2$, —PO-(OH)(O—C$_1$-C$_4$-alkyl), —PO(OR$^4$)R$^9$, —OPO-(OR$^4$)$_2$ or —C$_3$-C$_6$-cycloalkyl;
(e) perfluoro—C$_1$-C$_4$-alkyl;
R$^{25}$ is
(a) H,
(b) aryl as defined above, or
C$_1$-C$_6$-alkyl optionally substituted with aryl, F, Cl, Br, —OH, —NH$_2$, —NH(C$_1$-C$_4$-alkyl), —N(-C$_1$-C$_4$-alkyl)$_2$, or CF$_3$;
R$^{26}$ is
(a) aryl as defined above,
(b) C$_1$-C$_6$-alkyl optionally substituted with aryl, F, Cl, Br, —OH, —NH$_2$, —NH(C$_1$-C$_4$-alkyl), —N(-C$_1$-C$_4$-alkyl)$_2$, CF$_3$, —COOR$^4$, or CN,
(c) —OCH(R$^4$)—O—CO—R$^{4a}$, or
(d) —OH or —O—C$_1$-C$_6$-alkyl wherein alkyl is as defined in (b);
R$^{27}$ is
(a) H,
(b) C$_1$-C$_6$-alkyl optionally substituted with aryl, F, Cl, Br, —OH, —NH$_2$, —NH(C$_1$-C$_4$-alkyl ), —N(-C$_1$-C$_4$-alkyl)$_2$, CF$_3$, —COOR$^4$, or CN, or
(c) F, Cl, Br;
X is
(a) a carbon-carbon single bond,
(b) —CO—,
(c) —O—,
(d) —S—, (e) 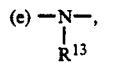

(f) 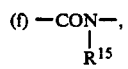

(g) 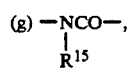

(h) —OCH$_2$—,
(i) —CH$_2$O—
(j) —SCH$_2$—,
(k) —CH$_2$S—,
(l) —NHC(R$^9$)(R$^{10}$),
(m) —NR$^9$SO$_2$—,
(n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—, (v) 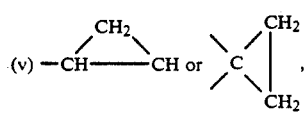

(w) 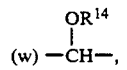

(x) 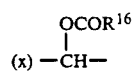

(y) 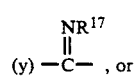, or (z) 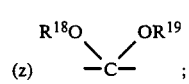;

r is 1 or 2; and
the pharmaceutically acceptable salts thereof.

One embodiment of the compounds of formula (I) are those compounds wherein:

J is
  a C atom;
M is
  —C(O)—;
K and L are
  connected together to form a 6 membered aromatic ring containing one N atom that is not at K and five C atoms which may be substituted at the carbon atoms with R$^{8a}$ and R$^{8b}$;
R$^1$ is
  (a) —NH—SO$_2$CF$_3$;
  (b) —SO$_2$NH-heteroaryl as defined above,
  (c) —CH$_2$SO$_2$$_1$NH-heteroaryl as defined above,
  (d) —SO$_2$NH—CO—R$^{22}$,
  (e) —CH$_2$SO$_2$NH—CO—R$^{22}$,
  (f) —CONH—SO$_2$R$^{22}$,
  (g) —CH$_2$CONH—SO$_2$R$^{22}$,
  (h) —NHSO$_2$NHCO—R$^{22}$,
  (i) —NHCONHSO$_2$—R$^{22}$,
  (j) —SO$_2$NHCO$_2$R$^{22}$,
  (k) —SO$_2$NHCON$^4$R$^{22}$,
  (l) —COOH or,
  (m) —tetrazolyl;
R$^{2a}$ is
  H;
R$^{2b}$ is
  H, F, Cl, CF$_3$, C$_1$-C$_6$-alkyl, C$_2$-C$_6$-alkenyl, C$_2$-C$_6$-alkynyl, or aryl;
R$^{3a}$ is
  H;
R$^{3b}$ is
  H, F, Cl, CF$_3$, C$_1$-C$_4$-alkyl, C$_2$-C$_4$-alkenyl, C$_2$-C$_4$-alkynyl, C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$ or —NH—SO$_2$CH$_3$;
E is
  a single bond, —O— or —S—;
R$^6$ is
  (a) C$_1$-C$_5$ alkyl optionally substituted with a substituent selected from the group consisting of C$_3$-C$_5$-cycloalkyl, Cl, CF$_3$, CCl$_3$, —O—CH$_3$, —OC$_2$H$_5$, —S—CH$_3$, —S—C$_2$H$_5$, phenyl, or F;
  (b) C$_2$-C$_5$-alkenyl or C$_2$-C$_5$-alkynyl; or,
  (c) C$_3$-C$_5$-cycloalkyl;
R$^{8a}$ and R$^{8b}$ are independently
  (a) H, provided they are not both H,
  (b) C$_1$-C$_8$-alkyl substituted with OCOR$^{4a}$, or aryl;
  (c) —NO$_2$, (d) 

(e) —CONR$^4$R$^{22}$, (f) 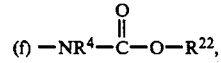

(g) —NR$^4$R$^{22}$,
(h) —CF$_3$,
(i) —CO$_2$R$^{4a}$,
(j) —CO-aryl as defined above
(k) —SO$_2$—NR$^4$R$^9$,
(l) —N(R$^4$)SO$_2$R$^{22}$,
(m) aryl
(n) —NR$^4$CONR$^4$R$^{22}$,
(o) —N(R$^4$)SO$_2$N(R$^4$)R$^{22}$, (p) 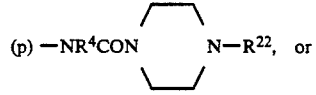, or (q) 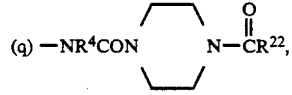

(r) 

(s) heteroaryl
X is
  a single bond;
r is one.

In a class of this embodiment are those compounds of Formula (I) wherein:

R¹ is
(a) —NH—SO₂—CF₃,
(b) —SO₂NH-heteroaryl as defined above.
(c) —SO₂NH—CO—R²²,
(d) —CONH—SO₂R²²,
(e) —SO₂NHCO₂R²²,
(f) —SO₂NHCON⁴R²²;
(g) —COOH or
(h) —tetrazolyl:

E is
a single bond;

r is
one,

R²ᵃ, R²ᵇ, R³ᵃ and R³ᵇ are each
H, —C₁-C₆-alkyl, —C₂-C₆-alkenyl, —C₂-C₆-alkynyl, —Cl, —F, —NO₂, —CF₃;

R⁶ is
—C₁-C₄-alkyl, -cyclopropyl, —CH₂CH₂CH₂CF₃, —CH₂CH₂CF₃, —C₂-C₅-alkenyl, -cyclopropylmethyl or methyl;

R⁸ᵃ and R⁸ᵇ are each independently
H, —NO₂, —NR⁴R²², —NR⁴COOR²², NR⁴CONR⁴R²², CH₂OCO(C₁-C₄-alkyl), NR⁴COR²², CO₂R⁴ᵃ, heteroayl, —CH₂Ph, —CONR⁴R²²,

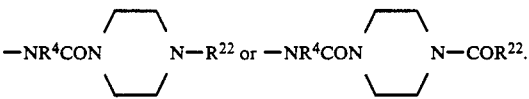

In a subclass are those compounds of Formula (I) wherein:

R¹ is
(a) —SO₂NHCOR²²,
(b) —CONHSO₂R²²,
(c) —NHSO₂CF₃;
(d) —SO₂NHCO₂R²²,
(e) —SO₂NHCON⁴R²²,
(f) —COOH, or
(g) —tetrazolyl;

R²ᵃ, R²ᵇ, and R³ᵃ and R³ᵇ each
H, —C₁-C₄-alkyl, —Cl or F;

R⁶ is
-n-propyl, ethyl, -n-butyl, -trans-2-butenyl, CH₂CH₂CF₃, —CH₂CH₂CH₂CF₃-cyclopropyl, -cyclopropylmethyl, methyl;

R⁸ᵃ and R⁸ᵇ are each independently
H, —NO₂, —NH₂, —NHCOCH₃, —NHCH₃, —N(CH₃)₂, —COOH, —COOCH₃, —CH₂COCH₃, —N(R⁴)CON(R⁴)₂, —N(R⁴)CO₂R²², —N(R⁴)COR²², NHMe, CH₂Ph, heteroaryl,

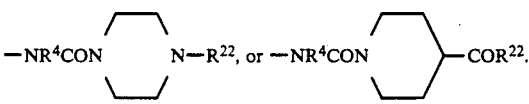

Exemplifying this subclass are the following compounds:
(1) 1-[(2'-(N-Benzoylsulfonamido)biphen-4-yl)-methyl]-2-n-butyl-5,7-dimethylpyrido[2,3-d]-pyrimidin-4-(1H)-one;

(2) 2-n-Butyl-5,7-dimethyl-1-[(2'-(N-trifluoro-methylsulfonylcarboxamido)biphen-4-yl)methyl]-pyrido[2,3-d]pyrimidin-4(1H)-one;
(3) 6-Amino-2-n-butyl-1-[2'-(tetrazol-5-yl)biphen-4-yl)methyl]pyrido[2,3-d]pyrimidin-4-(1H)-one; and
(4) 6-Amino-2-n-butyl-6-methyl-1-[(2'-(tetrazol-5-yl)biphen-4-yl)methyl]pyrido[3,2-d]pyrimidin-4-(1H)-one.

In a second embodiment are those compounds of formula (I) wherein:
M is
a C atom;

K is
—C(O)—;

J and L are connected together to form a 6 membered aromatic ring containing one N atom that is not at J and five C atoms which may be substituted at the carbon atoms with R⁸ᵃ and R⁸ᵇ. The class and subclass of this embodiment are the same as those described above.

Exemplifying this subclass are the following compounds:
(1) 3-[(2'-(N-Benzoylsulfonamido)biphen-4-yl)]-methyl-2-n-butyl-6-(N-isopropyloxycarbonyl-N-benzyl)aminopyrido[2,3-d]pyrimidin-4(3H)-one;
(2) 2-n-Butyl-6-(N-isopropyloxycarbonyl-N-methyl)amino-3-[(2'-(N-trifluoromethylsulfonyl-carboxamido)biphen-4-yl)methyl]pyrido[2,3-d]-pyrimidin-a(3H)-one;
(3) 6-(N-Benzoyl-N-n-pentyl)amino-3-[2'-(N-benzoylsulfonamido)biphen-4-yl)methyl]-2-n-propyl-pyrido[3,2-d]pyrimidin-4(3H)-one;
(4) 6-(N-Benzoyl-N-n-pentyl)amino-3-[2'-(N-benzoylsulfonamido)biphen-4-yl)methyl]-2-n-propyl-pyrido[2,3-d]pyrimidin-4(3H)-one;
(5) 6-Amino-2-n-Butyl-3-[(2'-(tetrazol-5-yl)biphen-4-yl)methyl]pyrido[2,3-d]pyrimidin-4-(3H)-one;
(6) Acetamido-2-n-Butyl-3-[2'-(tetrazol-5-yl)-biphen-4-yl)methyl]pyrido[2,3-d]pyrimidin-4(3H)-one;
(7) 2-n-Butyl-7-carboxy-3-[(2'-(tetrazol-5-yl)-biphen-4-yl)methyl]pyrido[2,3-d]pyrimidin-4-(3H)one;
(8) 2-n-Butyl-6-(N-isobutyloxycarbonyl)amino-3-[(2'-(tetrazol-5-yl)biphen-a-yl)methyl]pyrido-[2,3-d]pyrimidin-4-(3H)-one;
(9) 2-n-Butyl-6-[N-(morpholin-4-yl)carbamoyl)-N-methyl]amino-3-[(2'-tetrazol-5-yl)biphen-4-yl)-methyl]pyrido[2,3-d]pyrimidin-4(3H)-one;
(10) 2-n-Butyl-6-(N-isopropyloxycarbonyl-N-methyl)-amino-3-[2'-tetrazol-5-yl)biphen-4-yl)methyl]-pyrido[2,3-d]pyrimidin-4(3H)-one;
(11) 6-(N-Benzyloxycarbonyl-N-methyl)amino-2-n-butyl-3-[(2'-(tetrazol-5-yl)biphen-4-yl)methyl]-pyrido[2,3-d]pyrimidin-4(3H)-one;
(12) 6-[N-Benzyl-N-n-butyloxycarbonyl]amino-2-propyl3-[(2'-tetrazol-5-yl)biphen-4-yl)methyl]-pyrido[2,3-d]pyrimidin-4(3H)-one;
(13) 6-(N-(p-Chloro)benzoyl-N-isobutyl)amino-2-n-propyl-3-[2'-tetrazol-5-yl)biphen-4-yl)methyl]-pyrido[3,2-d]pyrimidin-4(3H)-one;
(14) 6-(N-n-Propyl-N-isobutyloxcarbonyl)amino-2-n-propyl-3-[2'-tetrazol-5-yl)biphen-4-yl)methyl]-pyrido[3,2-d]pyrimidin-4(3H)-one;
(15) 2-n-Butyl-6-(N-methyl-N-isobutyloxcarbonyl)-amino-3-[2'-tetrazol-5-yl)biphen-4-yl)methyl]-pyrido[2,3-d]pyrimidin-4(3H)-one;
(16) 6-(N-Benzyl-N-butanoyl)amino-2-n-propyl-3[2'-(tetrazol-5-yl)biphen-4-yl)methyl]pyrido[2,3-d]pyrimidin-4(3H)-one;

(17) 6-(N-(p-Chloro)benzoyl-N-n-pentyl)amino-2-n-propyl-3-[2'-tetrazol-5-yl)biphen-4-yl)methyl]-pyrido[2,3-d]pyrimidin-4(3H)-one; and
(18) 6-(N-n-Propyl-N-isobutyloxcarbonyl)amino-2-n-propyl-3-[2'-(tetrazol-5-yl)biphen-4-yl)methyl]-pyrido[2,3-d]pyrimidin-4(3H)-one;

Additional exemplifications of pyrido[3,2-d]pyrimidinones are as follows:

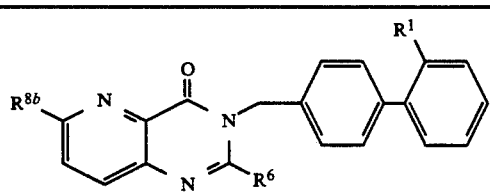

| ACID | R⁶ | R⁸ᵇ |
|---|---|---|
| TET | Pr | —N(Bn)CO₂Bu |
| TET | Bu | —N(Me)CO₂iBu |
| TET | Pr | —N(Bn)COPr |
| TET | Pr | —N(Pn)COPh |
| TET | Pr | —N(Pn)COPh-4-Cl |
| TET | Pr | —N(iBu)CO₂iBu |
| SO₂NHCOPh | Pr | —N(Pn)COPh |
| TET | Pr | —N(Bu)COPh |
| TET | Pr | —N(Bn)Bz |
| TET | Et | —N(Bn)Bz |
| TET | Me | —N(Bn)Bz |
| TET | Pr | —N(Bu(CO₂Bu |
| TET | Pr | —N(Bn)CO₂Et |
| TET | Pr | —N(Pn)CO-4-Pyr |
| TET | Pr | —N(Bu)COPh-4-F |
| TET | Pr | —N(Bu)CO-4-Pyr |
| TET | Pr | —(CH2-3-Pyr)CO₂Pr |
| TET | Pr | —(CH2-2-Pyr)CO₂Pr |
| TET | Pr | —(CH2-2-Pyr)CO₂Et |
| TET | Pr | —N(Pn)COPh-4-OH |
| TET | Pr | —N(Bn)CO-2-Pyr |
| TET | Pr | —N(Bz)CH₂-3-Pyr |
| TET | Pr | —N(Bz)CH₂-4-Pyr |
| TET | Pr | —N(Bn)CO-4-Pyr |
| TET | Pr | —N(Bz)CH₂-2-Pyr |
| TET | Pr | —N(Bn)CO-3-Pyr. |

Further exemplifications of the embodiment include:

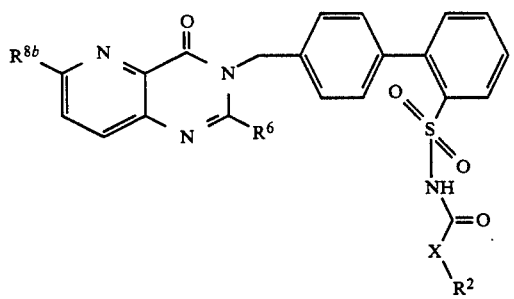

X = O, CH₂ or NH
X—R² = R²³

| R⁶ | R² | R⁸ᵇ |
|---|---|---|
| Pr | butyl | 2-pyridyl |
| Pr | butyl | NH2— |
| Pr | butyl | BuNHCONH— |
| Pr | butyl | EtNHCONH— |
| Pr | 2-dimethyaminoethyl | EtNHCONH— |
| Bu | butyl | iPrN(Me)CONH— |
| Pr | butyl | iPrNHCONH— |
| Pr | propyl | iPrNHCONH— |
| Pr | pentyl | iPrNHCONH— |
| Pr | butyl | MeNHCONH— |

-continued

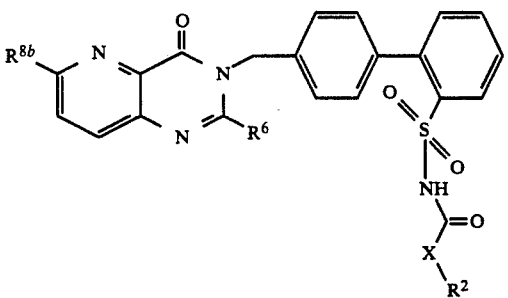

X = O, CH₂ or NH
X—R² = R²³

| R⁶ | R² | R⁸ᵇ |
|---|---|---|
| Pr | 3-methylbutyl | EtNHCONH— |
| Pr | 3-methylbutyl | MeNHCONH— |
| Pr | butyl | EtNHCONH— |
| Pr | 2-cyclopropylethyl | EtNHCONH— |
| Pr | 3.3-dimethylbutyl | EtNHCONH— |
| Bu | pentyl | iPrNHCONH— |
| Bu | butyl | iPrNHCONH— |
| Pr | 2-methoxyethyl | iPrNHCONH— |
| Pr | 3-methylbutyl | Me₂NCOHN— |
| Pr | 3-methylbutyl | PhCONH— |
| Pr | 3-methylbutyl | 4-HO—PhCONH— |
| Pr | 3-methylbutyl | 4-MeO—PhCONH— |
| Pr | 3-methylbutyl | 4-Me₂N—PhCONH— |
| Bu | 3.3-dimethylbutyl | PhCONH— |
| Pr | 2-cyclopropylethyl | 2-FurylCONH— |
| Bu | butyl | HOCH₂CH₂CONH— |
| Pr | 3.3-dimethylbutyl | —NHCOCH₂CH₂COOH |
| Bu | butyl | —NHCOCH₂COOH |
| Pr | 3-methylbutyl | Me₂NCH₂CH₂CONH— |
| Bu | butyl | Me₂NC(N)NH— |
| Pr | 3.3-dimethylbutyl | 4-cPrCO-piperazine-CO—NH |
| Bu | butyl | EtNHCOHN— |
| Pr | butyl | EtNHCOHN— |
| Pr | cyclopropylethyl | EtNHCONH— |
| Pr | cyclopropylethyl | EtNHCOHN— |
| Pr | 3.3-dimethylbutyl | 4-Me-piperazine-CO—NH |
| Bu | 2-cyclopropylethyl | morpholineCONH— |
| Pr | butyl | PrOCONH— |
| Pr | 3.3-dimethylbutyl | H₂NCONH— |
| Bu | 2-cyclopropylethyl | HOCH₂CONH— |
| Bu | 3.3-dimethylbutyl | 4-pirydylCONH— |
| Et | 2-cyclopentylethyl | EtNHCONH— |
| Pr | 3-methylbutyl | MeNHCONH— |
| Pr | 3-methylbuten-2-yl | EtNHCONH— |
| Bu | 2-cyclopropylethyl | EtNHCONH— |
| Bu | 3-methylbutyl | EtNHCONH— |
| i-Bu | 3-methylbutyl | EtNHCONH— |
| c-PrCH₂ | 3-methylbutyl | EtNHCONH— |
| n-Pn | 3-methylbutyl | EtNHCONH— |
| Bu | 2-cyclopropylethyl | MeNHCONH— |
| Bu | 3-methylbutyl | MeNHCONH— |
| Bu | 3-methylbutyl | Et₂NCONH— |
| Bu | 3-methylbutyl | i-PrNHCONH— |
| Bu | 3-methylbutyl | EtNMeCONH— |
| Bu | 3.3-dimethylbutyl | MeNHCONH |
| Bu | 2-methoxyethyl | EtNHCONH— |
| Bu | 2-ethoxyethyl | EtNHCONH— |
| Bu | 2-isopropoxyethyl | EtNHCONH— |
| Bu | 2-isopropoxylethyl | MeNHCONH— |
| Pr | 2-cyclopropylpropyl | EtNHCONH— |
| Pr | 3-methylbutyl | 2-furoylCONH— |
| Pr | 2-phenylethyl | EtNHCONH— |
| Et | cyclopentylmethyl | iPrNHCONH— |
| Pr | 2-methoxybenzyl | EtNHCONH— |
| Et | 3-methoxybenzyl | EtNHCOHN— |
| Pr | 3-methoxybenzyl | morpholineCONH— |
| Et | benzyl | EtCONH— |
| Pr | 2-cyclopropylpropyl | EtCONH— |

In a third embodiment are those compounds formula (I) wherein:

M is
a C atom;
K is
C=NR$^{22}$;
J and L are connected together to form a 6 membered aromatic ring containing one N atom that is not at J and five C atoms which may be substituted at the carbon atoms with R$^7$, R$^{8a}$ and R$^{8b}$. The class and sub-class of this embodiment are the same as those described above.

Exemplifying this subclass are the following compounds:

(1) N-Methyl3-[(2'-(N-benzoylsulfonamido)biphen-4-yl )methyl]-2-n-butyl-6-(N-isopropyloxy-carbonyl-N-methyl)aminopyrido[2,3-d]pyrimidin-4(3H)-imine; and, (2) N-Methyl 2-n-butyl-6-(N-isopropyloxycarbonyl-N-methyl )amino-3-[(2'-(N-trifluoromethylsulfonyl-carboxamido)biphen-4-yl)methyl]-pyrido[2,3-d]pyrimidin-4(3H)-imine.

(3) N-Phenyl-5-amino-2-n-butyl-3-[(2'-(tetrazol-5-yl)biphen-4-yl)methyl]pyrido[2,3-d]-pyrimidin-4(3H)-imine;

(4) N-Butyl-2-n-butyl-3-[(2'-tetrazol-5-yl)-biphen-a-yl)methyl]-5-(N-isopropylcarbamoyl)-aminopyrido[2,3-d]pyrimidin-4(3H)imine;

(5) N-Methyl-2-n-butyl-6-[N-(N-isopropyl-carbamoyl)-N-methyl]amino-3-[(2'-(tetrazol-5-yl)biphen-4-yl)methyl]pryrido[2,3-d]pyrimidin-4(3H)-imine;

(6) N-Propyl-2-n-butyl-6-[N-(morpholin-4-yl-carbamoyl) -N-methyl]amino-3-[(2'-tetrazol-5-yl)biphen-4 -yl)methyl]pyrido[2,3-d]pyrimidin-4(3H)-imine;

(7) N-Methyl-2-n-butyl-6-(N-isopropyloxycarbonyl-N-methyl)amino-3-[(2'-(tetrazo;-5-yl)biphen-4-yl)methyl)pyrido[2,3-d]pyrimidin-4(3H)-imine;

(8) N-Benzyl-6-(N-benzyloxycarbonyl-N-methyl)amino-2-n-butyl-3-[(2'(tetrazol-5-yl)biphen-4-yl) methyl]pyrido[2,3-d]pyrimidin-4(3H)-imine;

In naming compounds of Formula (I) which contain a biphenylmethyl substituent, it should be noted that the following two names for compound (i) shown below are considered to be equivalent:

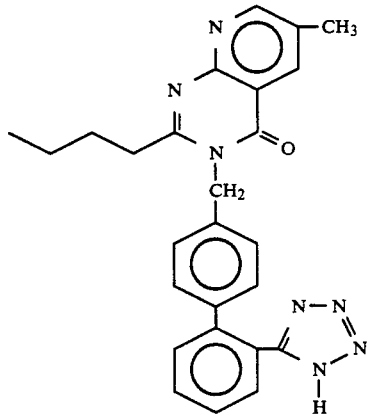

(i)

(1) 2-n-Butyl-6-methyl-3-[(2'-(tetrazol-5-yl)biphen-4-yl)methyl]pyrido[2,3-d]pyrimidin-4-(3H)-one; or, (2) 2-n-Butyl-6-methyl-3-[(2'-(tetrazol-5-yl)[1,1']-biphenyl-4-yl)methyl]pyrido[2,3-d]pyrimidin4(3H)-one.

For a general review of the synthesis and reactivity of 2,3-disubstituted pyrido[2,3-d] or [3,4-d] or [3,2-d] or [4,3-d]pyrimidin-4(3H)-ones, see A. R. Katritzky, et. al., *Comprehensive Heterocyclic Chemistry*, Vol. 3,201 (1984) and W. J. Irwin, et al., *Advances in Heterocyclic Chemistry*, vol. 10,149 (1969).

| ABBREVIATIONS | |
|---|---|
| DMAP | Dimethylaminopyridine |
| —OTs | p-toluenesulphonate |
| —OTf | Trifluoromethanesulfonate |
| DMF | Dimethylformamide |
| DBU | 1,8-Diazabicyclo[5.4.0]undecane |
| FABMS | Fast Atom bombardment mass spectroscopy |
| THF | Tetrahydrofuran |
| DMSO | Dimethylsulfoxide |
| EtAc | Ethyl acetate |
| HOAc | Acetic Acid |
| TFA | Trifluoroacetic acid |
| Bu | butyl |
| Tet | tetrazolyl |
| Pr | propyl |
| iPr | isopropyl |
| cPr | cyclopropyl |
| n-Pn | n-pentyl |
| Bn | benzyl |
| Bz | benzoyl |

Scheme 1 illustrates the preferred preparation of 2-substituted pyrido[2,3-d] or [3,2-d] or [3,4-d] or [4,3-d]pyrimidin-4(3H)-one of formula (I) where E is a single bond. An appropriately substituted ortho amino pyridine carboxylic acid 1 is treated with two equivalents of the requisite acyl chloride in dimethylformamide (DMF) with triethylamine and dimethylaminopyridine (DMAP) at 0° C. This mixture is then heated to 110° C. for 2 hours after which time excess ammonium carbonate is added. Any recovered bis amide 2 may be converted to the pyrimidin-4(3H)-one 3 by treatment with base.

SCHEME 1

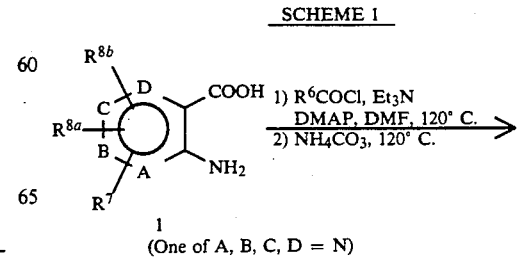

1
(One of A, B, C, D = N)

-continued
SCHEME 1

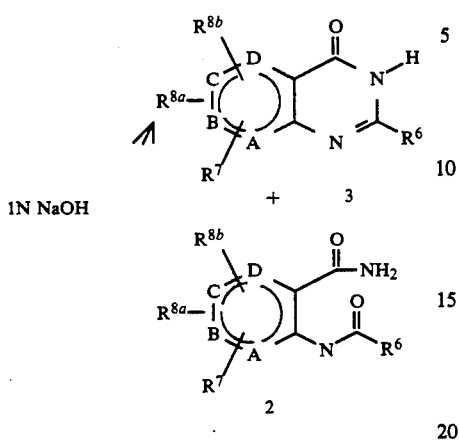

Scheme 2 illustrates the general preparation of 2,3-disubstituted pyrido[2,3-d] or [3,2-d] or [3,4-d] or [4,3-d]pyrimidin-4(3H)-one of Formula I (6) where E is a single bond. An appropriately substituted 2-alkyl-pyrimidin-4(3H)-one 4 is alkylated using sodium hydride and the appropriate alkyl halide 5 (or pseudo halide; i.e, Q is an appropriate leaving group such as

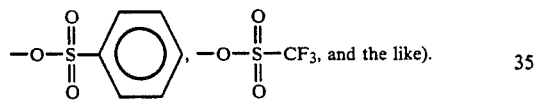

The alkylated material 6 may be transformed into the desired compound of Formula (I) by deprotection of the protecting groups for $R^1$ or by chemical transformation into the $R^1$ group desired. For example, when $R^1$ is a carboxy t-butyl ester or N-triphenylmethyl tetrazole, treatment of 6 with HCl/MeOH or acetic acid will give the desired $R^1$ carboxy or tetrazolyl functional group. When $R^1$ in 6 is nitrile, heating with trimethyltin azide will give the tetrazole function.

SCHEME 2

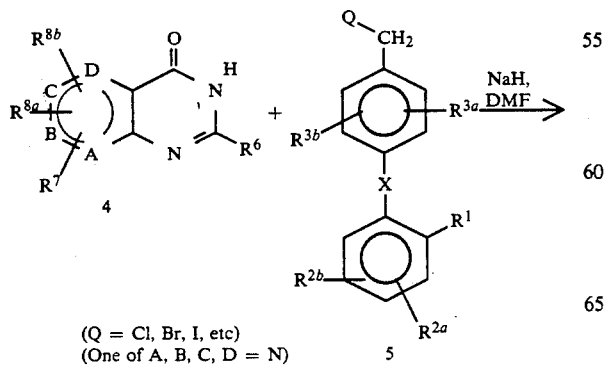

(Q = Cl, Br, I, etc)
(One of A, B, C, D = N)

-continued
SCHEME 2

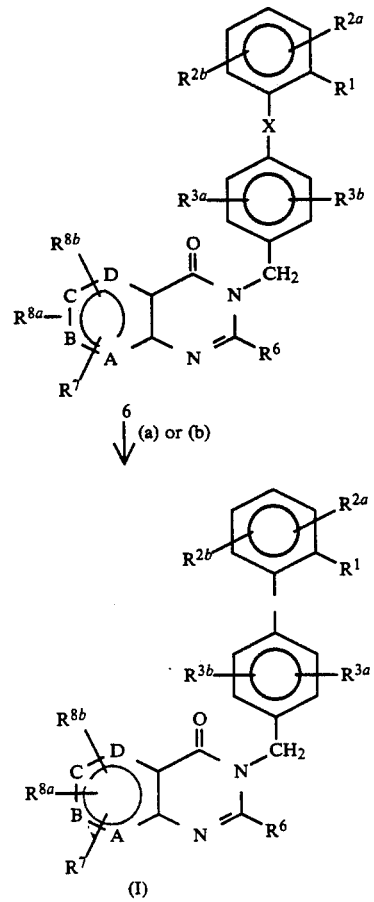

(a) when $R^1$ is t-butoxycarbonyl or N-triphenylmethyltetrazole treated with or HCl/MeOH or acetic acid respectively.

(b) when $R^1$ is C≡N treated with $(CH_3)_3SnN_3$.

REACTION SCHEME 3

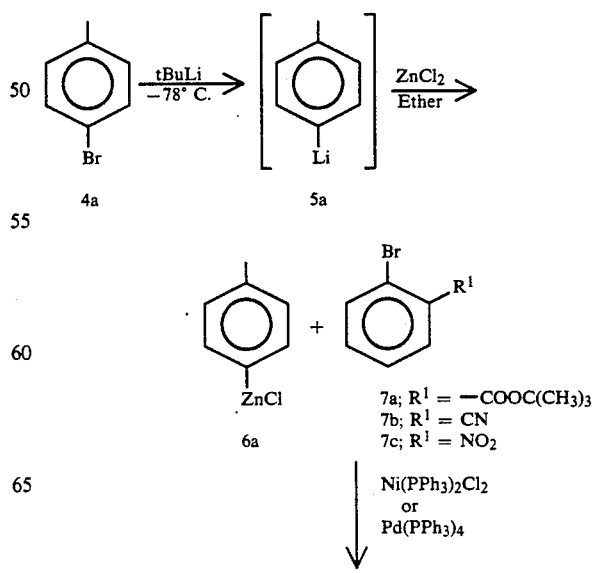

7a; $R^1$ = —COOC(CH$_3$)$_3$
7b; $R^1$ = CN
7c; $R^1$ = NO$_2$

Ni(PPh$_3$)$_2$Cl$_2$
or
Pd(PPh$_3$)$_4$

REACTION SCHEME 3 (continued)

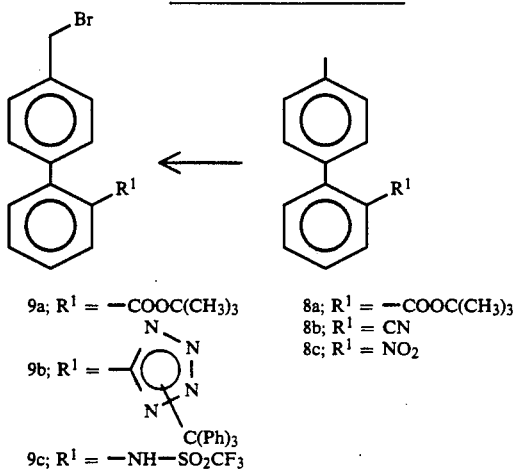

9a; $R^1$ = —COOC(CH$_3$)$_3$

9b; $R^1$ = [tetrazole-C(Ph)$_3$]

9c; $R^1$ = —NH—SO$_2$CF$_3$

8a; $R^1$ = —COOC(CH$_3$)$_3$
8b; $R^1$ = CN
8c; $R^1$ = NO$_2$

The benzyl halides (5) including the more preferred alkylating agents (9a and 9b, Reaction Scheme 3) can be prepared as described in European Patent Applications 253,310 and 291,969 and the references cited therein. However, a preferred method to prepare the biphenyl precursors 8a, 8b and 8c using Ni(O) or Pd(O) catalyzed cross-coupling reaction [E. Negishi, T. Takahashi, and A. O. King, Org. Synthesis, 66, 67 (1987)] is outlined in Reaction Scheme 3. As shown in Reaction Scheme 3, treatment of 4-bromotoluene (4a) with t-BuLi, followed by the addition of a solution of ZnCl$_2$, produces the organo-zinc compound (6a). Compound (6a) is then coupled with 7a or 7b in the presence of Ni(PPh$_3$)$_2$Cl$_2$ catalyst to produce the desired biphenyl compound 8a or 8b (PPh$_3$=triphenylphosphine). Similarly, 1-iodo-2-nitro-benzene (7c) is coupled with organo-zinc compound 6a in the presence of Pd(PPh$_3$)$_4$ catalyst [prepared by treating Cl$_2$Pd(PPh$_3$)$_2$ with (i-Bu)$_2$AlH (2 equiv.)] to give the biphenyl compound 8c. These precursors, 8a, 8b and 8c, are then transformed into halomethylbiphenyl derivatives 9a, 9b and 9c, respectively, according to procedures described in European Patent Applications 253,310 and 291,969.

When there is additional substitution on the second phenyl ring ($R^{2a}$, $R^{2b}$=hydrogen) the preferred method to prepare the biphenyl precursors 8d and 8e, using the Pd(O) catalyzed cross-coupling reaction [J. K. Stille, Angrew, Chem. Int. Ed. Engl., 25, 508 (1986)], is outlined in reaction Scheme 3a. As shown in reaction Scheme 3a, p-tolyltrimethyltin (6a) is coupled with 7d or 7e in refluxing toluene in the presence of 5 mole % of Pd(PPh$_3$)$_4$ to produce the desired biphenyl compounds 8d and 8e. Table I illustrates the synthetic utility of this protocol. Compounds 8d ($R^2$=NO$_2$) and 8e ($R^2$=NO$_2$) could be converted to their respective chlorides by catalytic hydrogenation, diazotization and treatment with copper (I) chloride. The biphenyl fluorides which could not be obtained by direct coupling to a fluoro arylbromide were prepared from 8d ($R^2$=NO$_2$) and 8e ($R^2$=NO$_2$) via reduction, formation of the diazonium tetrafluoroborate salt and thermal decomposition. These precursors 8d ($R^2$=NO$_2$ or F or Cl) and 8e ($R^2$=NO$_2$ or F or Cl) are then transformed into the halomethyl biphenyl derivatives 9d and 9e, respectively according to the procedures described in European Patent Applications 253,310 and 292,969.

REACTION SCHEME 3a

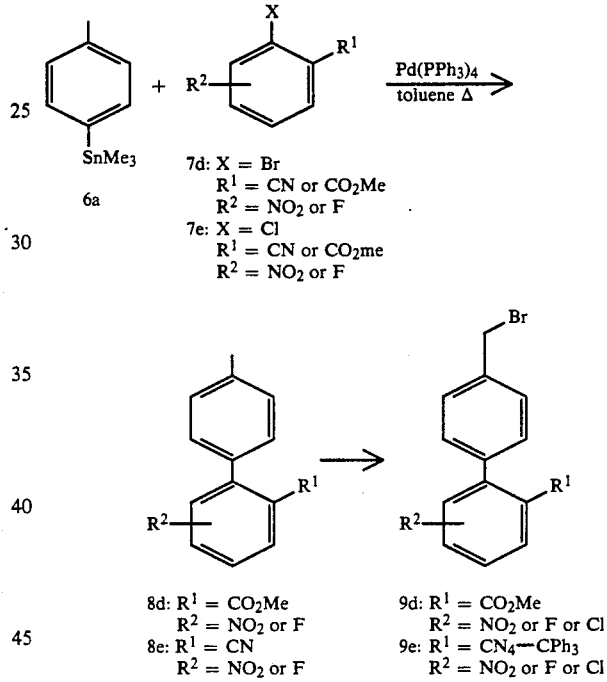

7d: X = Br
$R^1$ = CN or CO$_2$Me
$R^2$ = NO$_2$ or F

7e: X = Cl
$R^1$ = CN or CO$_2$me
$R^2$ = NO$_2$ or F

8d: $R^1$ = CO$_2$Me
$R^2$ = NO$_2$ or F
8e: $R^1$ = CN
$R^2$ = NO$_2$ or F

9d: $R^1$ = CO$_2$Me
$R^2$ = NO$_2$ or F or Cl
9e: $R^1$ = CN$_4$—CPh$_3$
$R^2$ = NO$_2$ or F or Cl

TABLE I

Biphenyl Synthesis

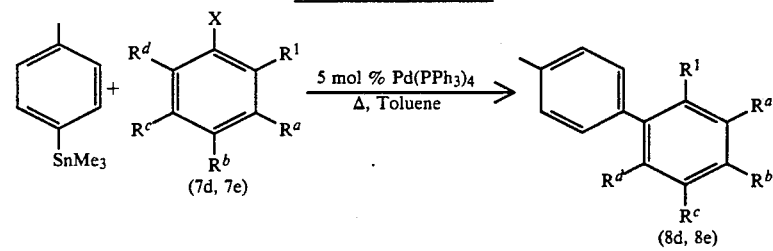

| X | $R^1$ | $R^a$ | $R^b$ | $R^c$ | $R^d$ | Product ($R^a$) | Rf (solvent) | Yield |
|---|---|---|---|---|---|---|---|---|
| Br | CO$_2$Me | NO$_2$ | H | H | H | 8d (3'nitro) | 0.35(15:1 Hex/EtOAC) | 71% |
| Br | CN | H | NO$_2$ | H | H | 8e (4'-nitro) | 0.62(2x 6:1 Hex/EtOAc) | 74% |
| Br | CO$_2$Me | H | F | H | H | 8d (4'-fluoro) | 0.43(15:1 Hex/EtOAc) | 83% |
| Cl | CO$_2$Me | H | H | NO$_2$ | H | 8d (5'-nitro) | 0.22(15:1 Hex/EtOAc) | 70% |
| Br | CO$_2$Me | H | H | H | NO$_2$ | 8d (6'-nitro) | 0.24(15:1 Hex/EtOAc) | 79% |
| Br | CN | H | F | H | H | 8e (4'-fluoro) | 0.44(15:1 Hex/EtOAc) | 64% |

TABLE I-continued

Biphenyl Synthesis

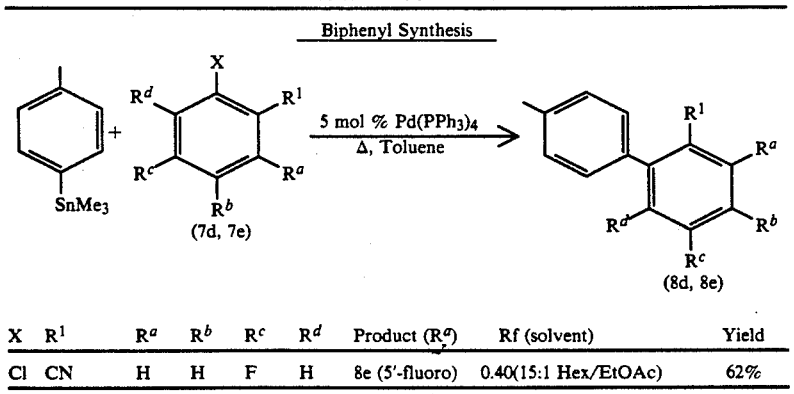

| X | R¹ | $R^a$ | $R^b$ | $R^c$ | $R^d$ | Product ($R^a$) | Rf (solvent) | Yield |
|---|----|----|----|----|----|----|----|----|
| Cl | CN | H | H | F | H | 8e (5'-fluoro) | 0.40(15:1 Hex/EtOAc) | 62% |

Scheme 4 illustrates an alternative method of preparing 2-substituted pyrido[2,3-d] pyrimidin-4-(3H)-one [A. Dornow, et al. *Chem. Ber.* 98, 1505 (1965); D. M. Mulrey, et al, *J.. Org. Chem.*, 29, 2903 (1964); and, S. C. Cottis, et al, *J. Org. Chem.*, 26, 79 (1961)]. An appropriately substituted 2-aminonicotinic acid amide 10 (prepared by partial hydrolysis of the corresponding nitrile) when treated with an alkyl ortho ester gives the corresponding 2-substituted pyrido[2,3-d]pyrimidin-4(3H)-one 11. This conversion could be applied to other isomeric pyridines.

SCHEME 4

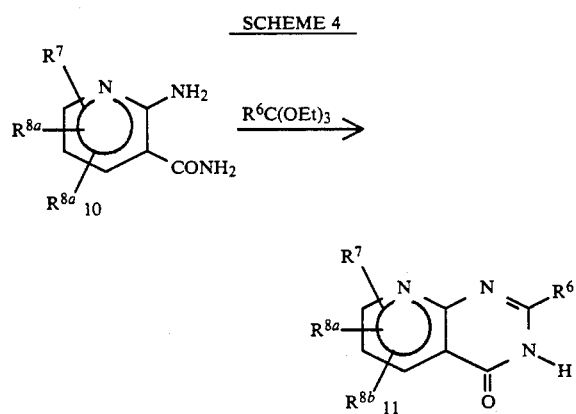

Scheme 5 illustrates an alternative method of preparing 2-substituted pyrido[3,4-d]pyrimidin-4(3H)-ones. An appropriately substituted 3-aminoisonicotinic acid 12 may be reacted with an alkyl imidate ester 13 to give a 2-substituted pyrido [3,4-d]pyrimidin-4(3H)-one 14. [A. deCat, et al, *Chem. Abstr.*, 50, 12063 (1956) and W. Ried, et al, *Ann. Chem.*, 707, 250 (1967)]. This methodology may also be applied to isomeric 2-aminopyridine carboxylic acids.

SCHEME 5

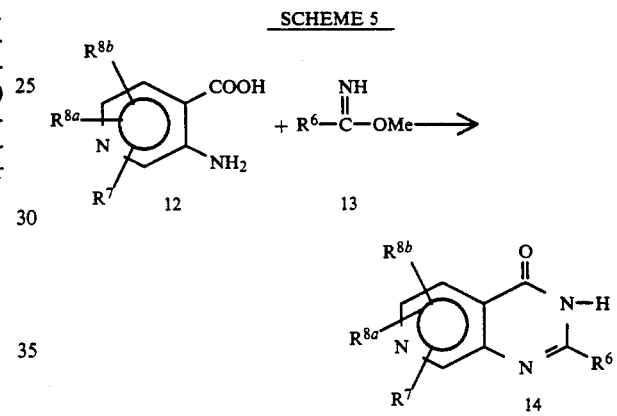

Scheme 6 illustrates a method of preparing 2,3-disubstituted pyrido[2,3-d], [3,2-d], [4,3-d], or [3,4-d]pyrimidin-4(3H)-ones. [A. G. Ismail, et al, *J. Chem. Soc.*, C, 2613 (1967); and W. J. Irwin, et al., *J. Chem. Soc.*, C, 4240 (1965]. An appropriately substituted ortho aminopyridine carboxylic acid 15 when treated with either two equivalents of an acid chloride in pyridine or in the presence of a base such as triethylamine in a solvent such as DMF will give rise on heating to a 2-substituted pyrido[2,3-d] or [3,2-d] or [4,3-d] or [3,4-dJ[1,3]oxazin-4-ones 16. These may be treated with an alkyl amine 17, and give rise to either the bis amide 18 or the cyclized pyrido-pyrimidin-4(3H)-one 19. The bis amide 18 may in turn be converted to the pyridopyrimidin4(3H)-one upon dissolution in phosphorus oxychloride.

SCHEME 6

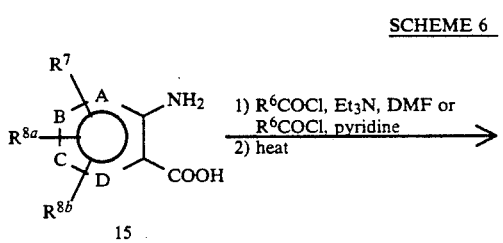

1) R⁶COCl, Et₃N, DMF or R⁶COCl, pyridine
2) heat (One of A, B, C, or D is nitrogen and the others are carbon)

SCHEME 6

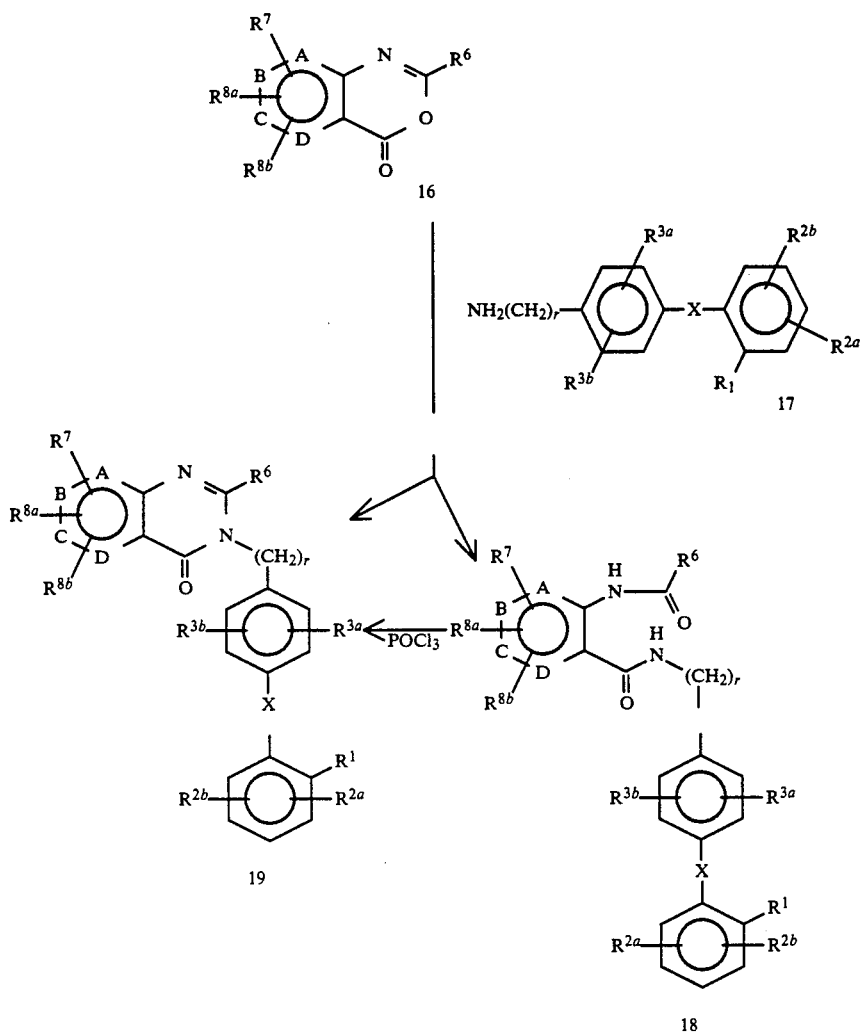

Scheme 7 illustrates the preparation of 1,2-disubstituted pyrido [2,3-d] or [3,2-d] or [3,4-d] or [4,3-d]pyrimdin-4(1H)-ones 20. An appropriately substituted ortho amino pyridine nitrile 21 may be acylated using the requisite acid chloride. The resulting amide 22 may be alkylated with an appropriate alkyl halide (or pseudo halide) 23 in the presence of sodium hydride. The resulting tertiary amide 24 is then rearranged/cyclized with basic hydrogen peroxide.

SCHEME 7

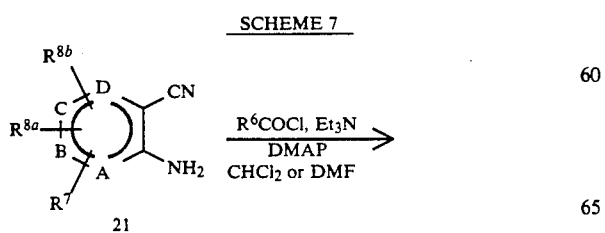

(One of A, B, C, or D is nitrogen and the others are carbon)

-continued
SCHEME 7

(Q = Cl, Br, I, etc.)

SCHEME 7 -continued

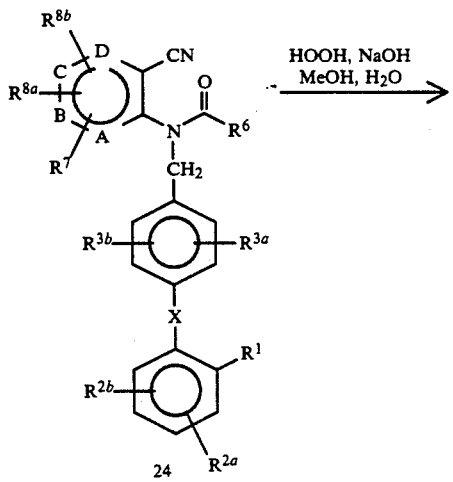

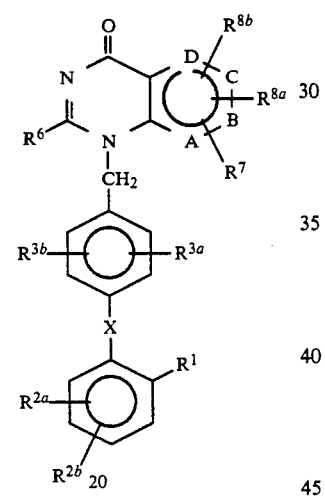

Scheme 8 illustrates a method of preparing 1,2-disubstituted pyrido[2,3-d]pyrimidin-4(1H)-ones 25. An appropriately substituted 2-alkylamino-3-cyanopyridine 26 may be hydrolyzed to the acid salt 27. Reaction with oxalyl chloride will give rise to the isotin 28. Condensation of the isotin with an imidate ester will give the 1,2-disubstituted pyrido 2,3-d]pyrimidin-4(1H)-one 25. [D. G. M., Coppala, et al, *J. Het. Chem.*, 22, 193 (1985)]. Use of a thioamidine will give a 1-alkyl-2-aminoalkyl-pyrido2,3-d]pyrimidin-4(1H)-one 29. This chemistry may be applicable to other isomeric pyridines.

SCHEME 8

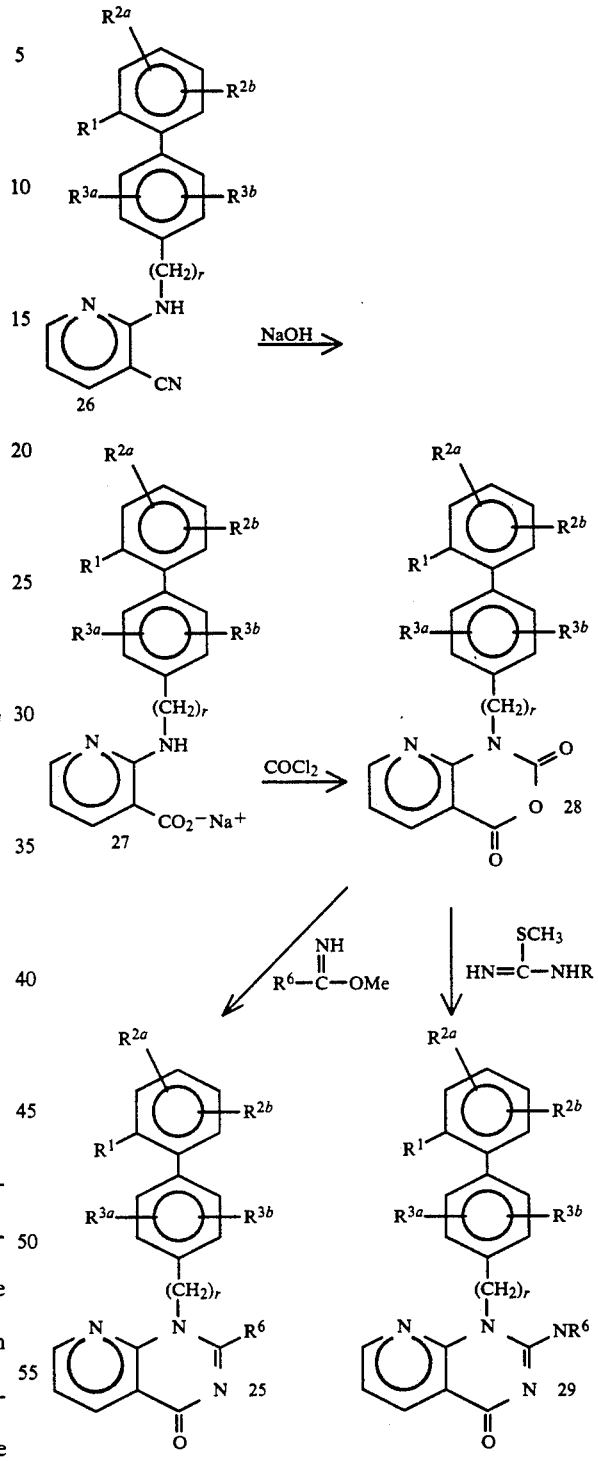

A method of preparing 2,3-disubstituted pyrido[2,3-d]pyrimidin-4(1H)-ones 30 where E=O, S or N is illustrated in Scheme 9. Condensation of the appropriate pyrimidine-2,3-dione or a derivative thereof 31 with an amino aldehyde 32 gives the pyrido[2,3-d]pyrimidinedione 33. [E. Stark, et al., *Tetrahedron*, 29, 2209 (1973)]. Alkylation of the heterocycle with an alkyl halide (or pseudohalide) in the presence of sodium hydride gives the 2-substituted pyrido[2,3-d]pyrimidin-4(1H)-one 30.

[A. Srinivason, et al, *J. Org. Chem.*, 43, 828 (1978)]. Alkylation of 30 in DMF as described in Scheme 2 gives the desired 2,3-disubstituted pyrido[2,3-d]pyrimidin-4(3H)-one.(I)

SCHEME 9

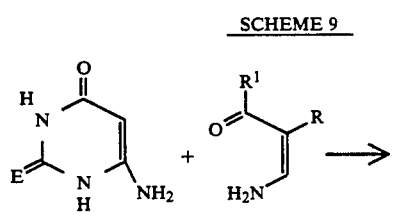

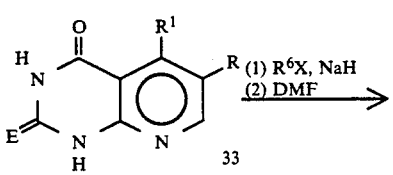

E = O, N, S
X = Cl, Br, I, OTs, OTf, etc
OTf = OSO$_2$CF$_3$
OTs = OSO$_2$-(4-methyl)phenyl

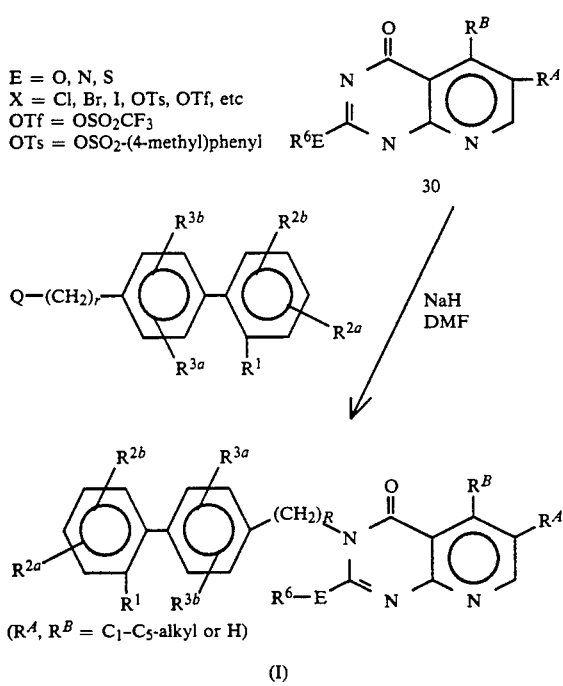

(R$^A$, R$^B$ = C$_1$-C$_5$-alkyl or H)

(I)

Scheme 10 describes a method for preparing 2,3-disubstituted pyrido[3,4-d]pyrimidin-4(3H)-ones where E=O, N, S, or C 34 from an ortho aminopyridine carboxylic acid 35 combined with an imidate ester where E=O, N, S, or C. The resulting heterocycle may subsequently be alkylated in the usual fashion to give the desired 2,3-disubstituted pyrido[3,4-d]-pyrimidin-4(3H)-one 34.

SCHEME 10

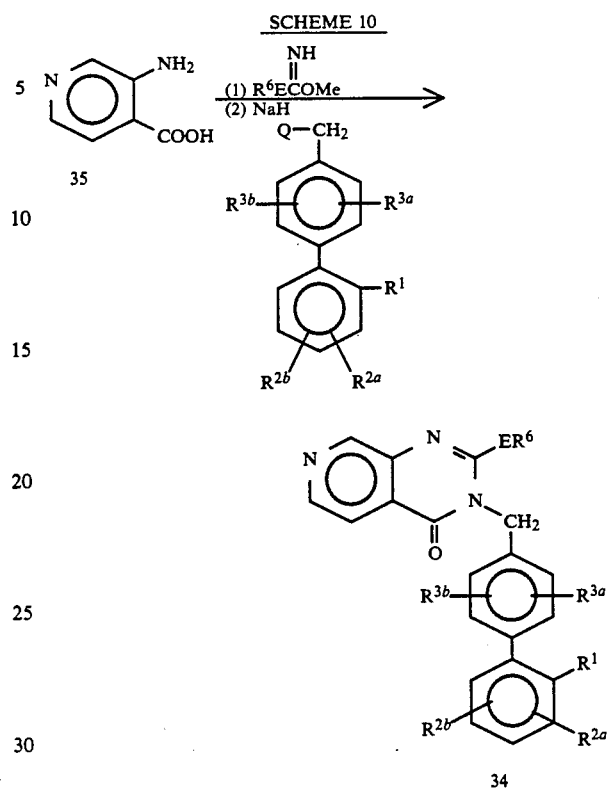

Scheme 11 illustrates a method for preparing N-alkyl, 2,3-disubstituted pyrido[4,3-d], or [3,4-d], or [2,3-d], or [3,2-d]pyridin-4(3H)-imines 36. A suitably protected 2,3-di substituted pyrido[4,3-d], [3,4-d], [2,3-d] or [3,2-d] pyrimidin-4(3H)-one 37 is treated with Lawesson's Reagent to give the corresponding thione 38. Condensation of the thione with an amine at an elevated temperature in a suitable solvent (e.g., benzene, DMF) gives the desired heterocycle 36 [T. Zimaitg, et al., *Indian J. Chem.*, 15B, 750–751 (1977) and L. Legrand et al, *Bull. Chem. Soc. Fr.*, 1411 (1975)].

SCHEME 11

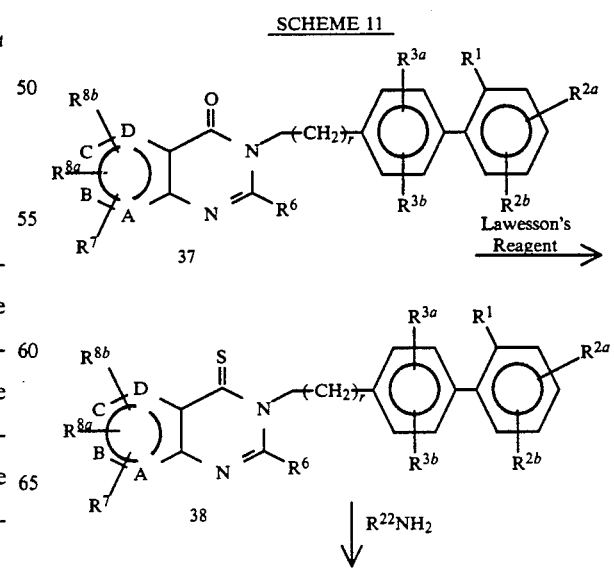

-continued
SCHEME 11

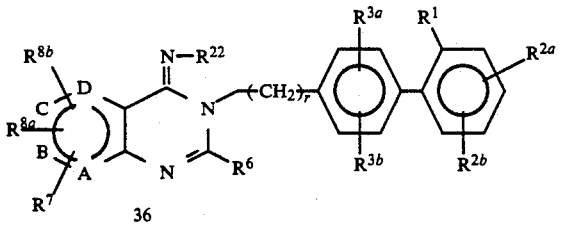

36

Note: one of A, B, C, or D is N and the others C.

Compounds of formula I where $R^1$ is —CONHSO$_2$R$^{22}$ (where $R^{22}$=alkyl, aryl or heteroaryl) may be prepared from the corresponding carboxylic acid derivatives (39) as outlined in Scheme 12. The carboxylic acid (39), obtained as described in Scheme 2, can be converted into the corresponding acid chloride by treatment with refluxing thionyl chloride or preferably with oxalyl chloride and a catalytic amount of dimethylformamide at low temperature [A. W. Burgstahler, L. O. Weigel, and C. G. Shaefer-*Synthesis*, 767, (1976)]. The acid chloride then can be treated with the alkali metal salt of $R^{22}SO_2NH_2$ to form the desired acylsulfonamide (40). Alternatively, these acylsulfonamides may be prepared from the carboxylic acids using N,N-diphenylcarbamoyl anhydride intermediates [F. J. Brown et al, European Patent Application, EP 199543; K. L. Shepard and W. Halczenko—*J. Het. Chem.*, 16, 321 (1979)]. Preferably the carboxylic acids can be converted into acyl-imidazole intermediates, which then can be treated with an appropriate aryl or alkylsulfonamide and diazabicycloundecane (DBU) to give the desired acylsulfonamide 40 [J. T. Drummond and G. Johnson, *Tetrahedron. Lett.*, 29, 1653 (1988)].

Compounds of formula I where $R^1$ is SO$_2$NHCOR$^{22}$ may be prepared as outlined in Scheme 13. The nitro compound, for example 8c (prepared as described in Scheme 3), can be reduced to the corresponding amino compound and converted into aromatic diazoniun chloride salt, which then can be reacted with sulfur-dioxide in the presence of a copper (II) salt to form the corresponding arylsulfonyl chloride 41 [H. Meerwein, G. Dirtmar, R. Gollner, K. Hafner, F. Mensch and O. Steifort, *Chem. Ber.*, 90, 841 (1957); A. J. Prinsen and H. Cerfontain, Recueil, 84, 24 (1965); E. E. Gilbert, *Synthesis*, 3 (1969) and references cited therein]. The sulfonyl chloride can be reacted with ammonia in aqueous solution or in an inert organic solvent [F. H. Bergheim and W. Baker, *J. Amer. Chem. Soc.*, 66, (1944), 1459], or with dry powdered ammonium carbonate, [E. H. Huntress and J. S. Autenrieth, *J. Amer Chem. Soc.*, 63 (1941), 3446; E. H. Huntress and F. H. Carten, *J. Amer. Chem. Soc.*, 62, (1940), 511] to form the sulfonamide 42. The sulfonamide must then be protected preferably with the triphenylmethyl group by reaction with triphenylmethylchloride and triethylamine to give 43. The benzyl bromide 44 may be prepared from the sulfonamide 43 as outlined in Scheme 16, and then can be reacted with an alkali metal salt of an appropriate heterocyclic compound to form the key sulfonamide 45. The sulfonamide 45 may be also prepared from the aromatic sulfonyl chloride 48 by treatment with ammonia. In addition, 48 may be prepared from the aryl amine 47 as outlined in Scheme 14. The reaction of 48 with appropriate amines followed by acyl chlorides (or acyl-imidazoles or other acylating agents) may produce the desired acylsulfonamides 46.

The compounds bearing $R^1$ as —SO$_2$NHR$^{22}$ (where $R^{22}$ is heteroaryl) may be prepared by reacting the aromatic sulfonyl chloride 48 with appropriate heteroaryl amines as outlined in Scheme 14 to give 49. The sulfonyl chloride 48 may be prepared using similar chemistry to that outlined above. The sulfonyl chloride 48 may be the preferred intermediate for the synthesis of this class of compounds. The aromatic sulfonyl chlorides may also be prepared by reacting the sodium salt of aromatic sulfonic acids with PCl$_5$ or POCl$_3$ [C. M. Surer, *The Organic Chemistry of Sulfur*, John Wiley & Sons, 459, (1944)]. The aromatic sulfonic acid precursors may be prepared by chlorosulfonation of the aromatic ring with chlorosulfonic acid [E. H. Huntress and F. H. Carten, *J. Amer. Chem. Soc.*, 62, 511 (1940)].

SCHEME 12

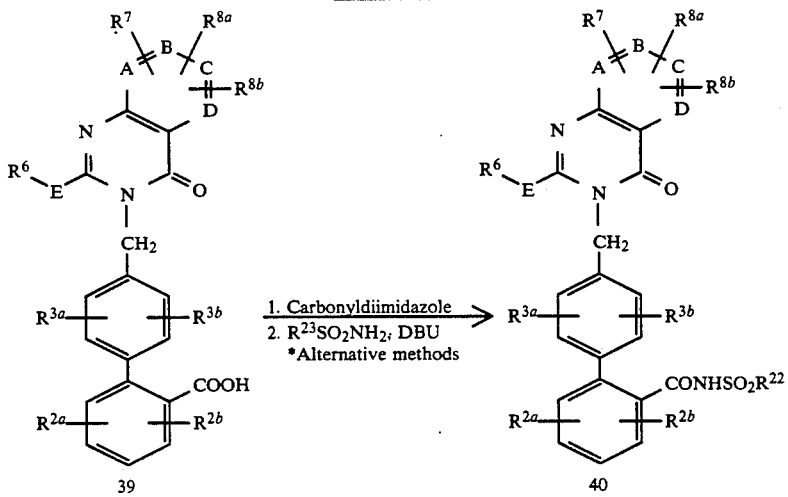

One of A, B, C, D is N and the others C
*Alternative Methods:
a) (i) SOCl$_2$, reflux
(ii) R$^{22}$SO$_2$NH$^-$M$^+$ (where M is Na or Li)

SCHEME 12
-continued
b) (i) (COCl)$_2$-DMF, −20° C.
   (ii) R$^{22}$SO$_2$NH$^-$M$^+$
c) (i) N(N,N-Diphenylcarbamoyl)pyridinium chloride/Aq. NaOH
   (ii) R$^{22}$SO$_2$NH$^-$M$^+$.
SCHEME 13
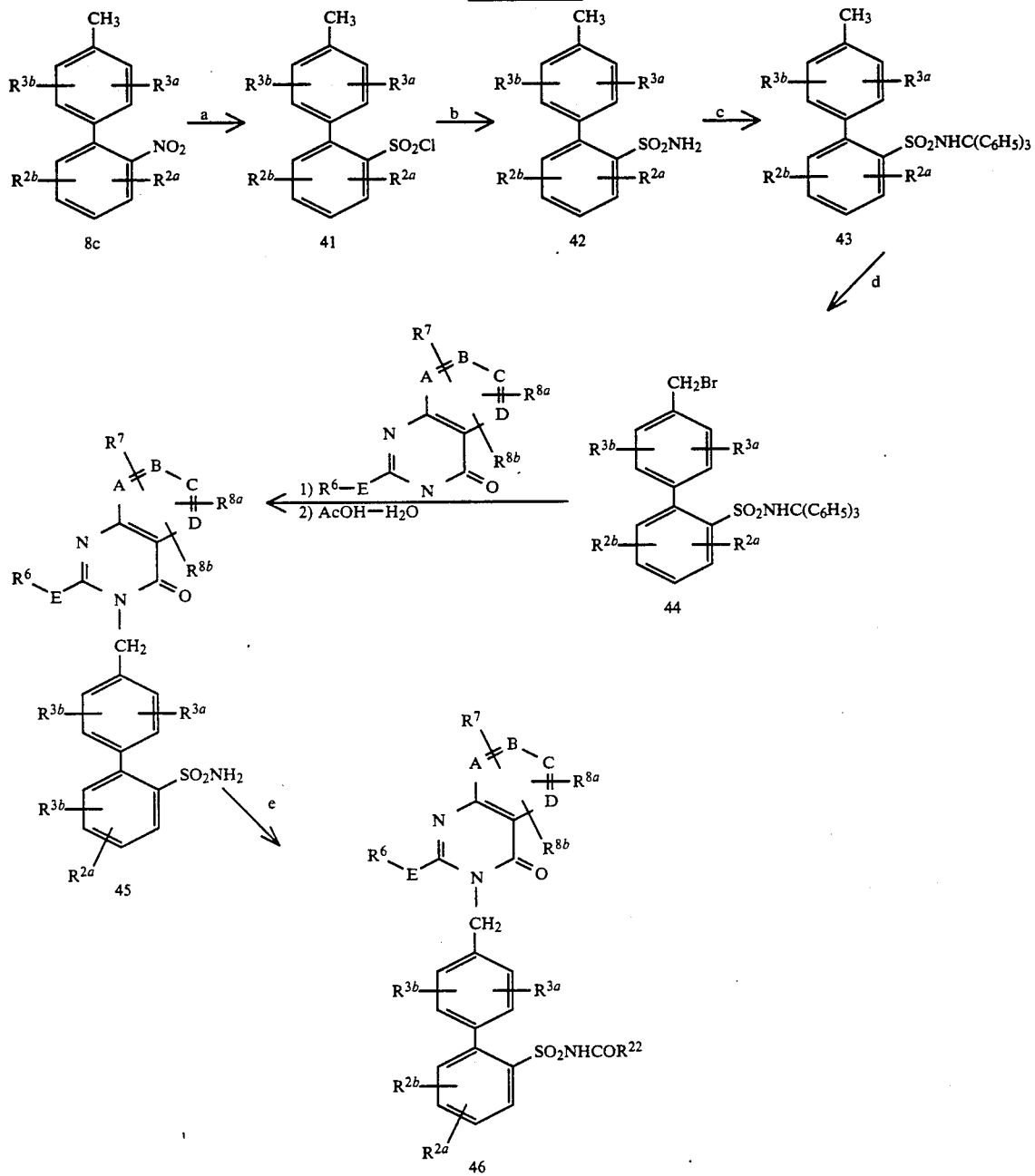
One of A, B, C, D is N and the others C
a. (i) H$_2$/Pd—C,
   (ii) NaNO$_2$—HCl,
   (iii) SO$_2$, AcOH, CuCl$_2$
b. NH$_3$ or (NH$_4$)$_2$CO$_3$
c. (C$_6$H$_5$)$_3$CCl, Et$_3$N, CH$_2$Cl$_2$, 25° C.
d. N-Bromosuccinimide
e. R$^{22}$COCl or R$^{22}$CO—Im or other acylating agents.

SCHEME 14
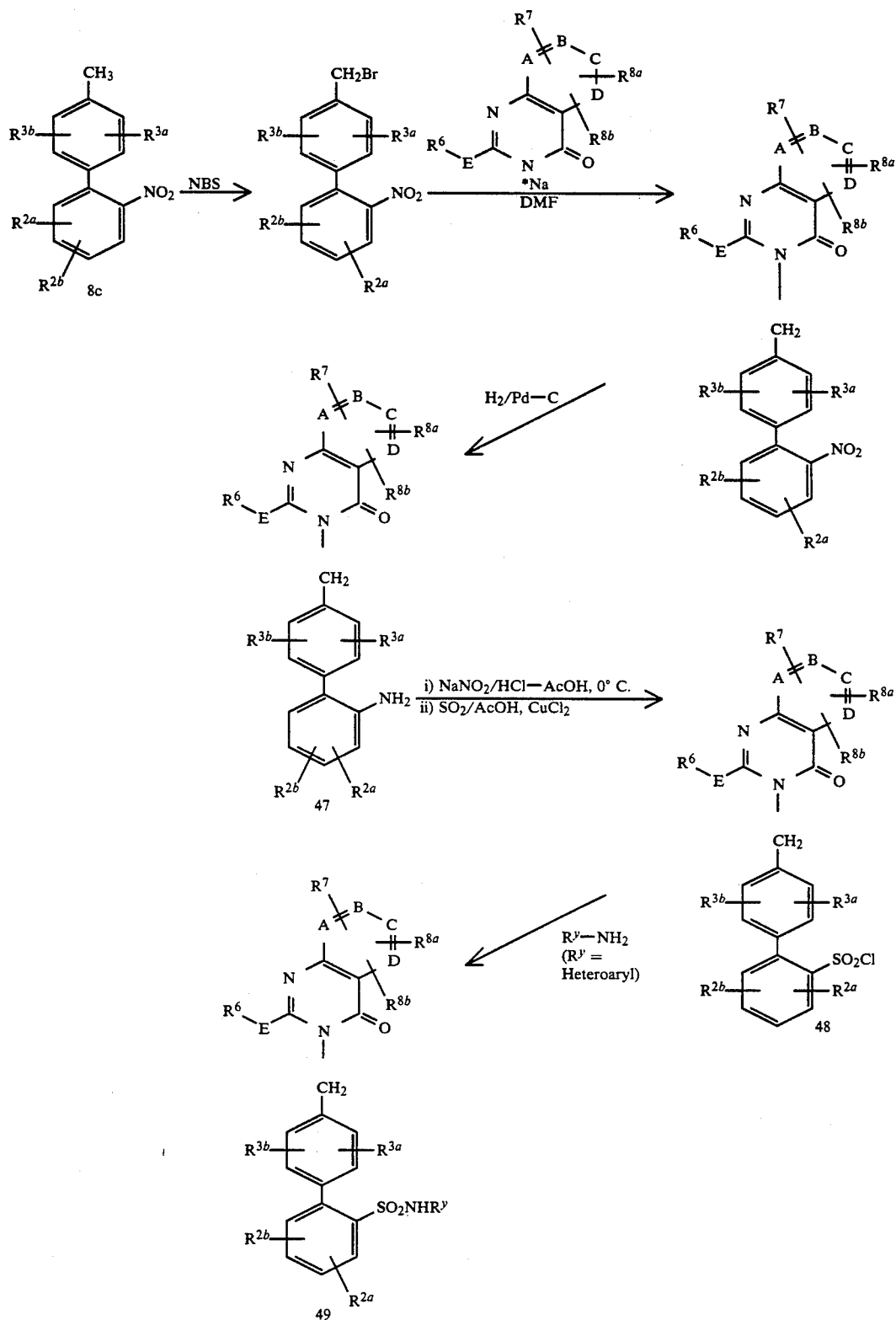
One of A, B, C, D is N and the others C

SCHEME 15

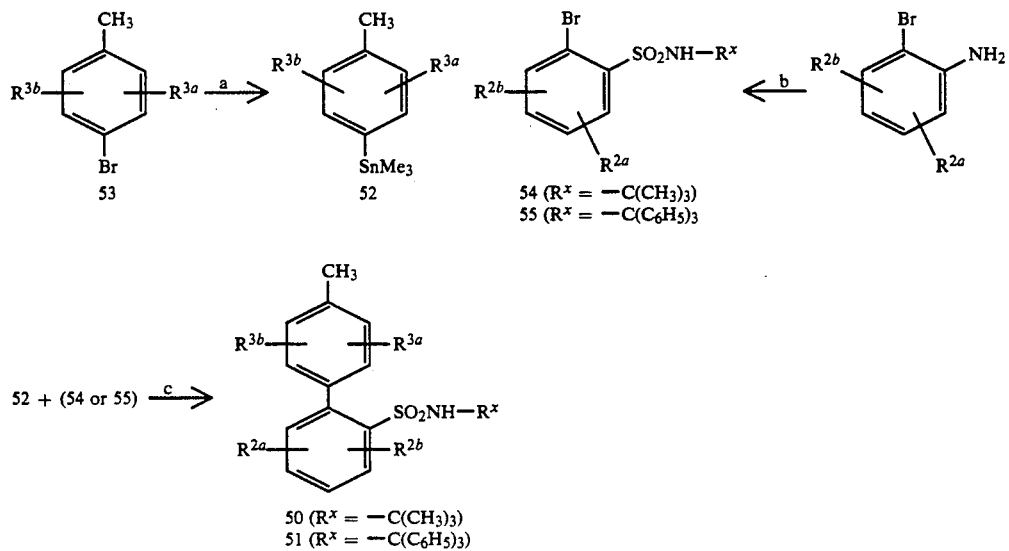

a. (i) t-BuLi/ether, −78° C.
   (ii) Me₃SnCl
b. (i) NaNO₂/HCl
   (ii) SO₂, CuCl₂
c. Pd(PPh₃)₄, Toluene, reflux or (PPh₃)₂PdCl₂, DMF, 90° C.

The biaryl sulfonamides 50 and 51 (described in Scheme 13 as 43) can be prepared alternatively using palladium(O) catalyzed cross-coupling reactions of appropriate aryl-organotin precursors [J. K. Stille, *Pure Appl. Chem.*, 57, 1771 (1985); T. R. Baiely, *Tetrahedron Lett.*, 27, 4407 (1986); D. A. Widdowson and Y. Z. Zhang, *Tetrahedron*, 42, 2111 (1986)], as outlined in Scheme 15. The organotin compound 52 [S. M. Moerlein, *J. Organometallic Chem.*, 319, 29 (1987)], obtained from the aromatic precursor 53, may be coupled with aryl sulfonamide 54 and 55 using Pd(PPh₃)₄ or (PPh₃)₂PdCl₂ as catalysts to give biaryl sulfonamide 50 and 51. Similarly, the benzyl bromide 56 may be alternatively prepared from the appropriate organotin precursor 57 using the Pd(O) catalyzed cross-coupling reaction as outlined in Scheme 16.

SCHEME 16

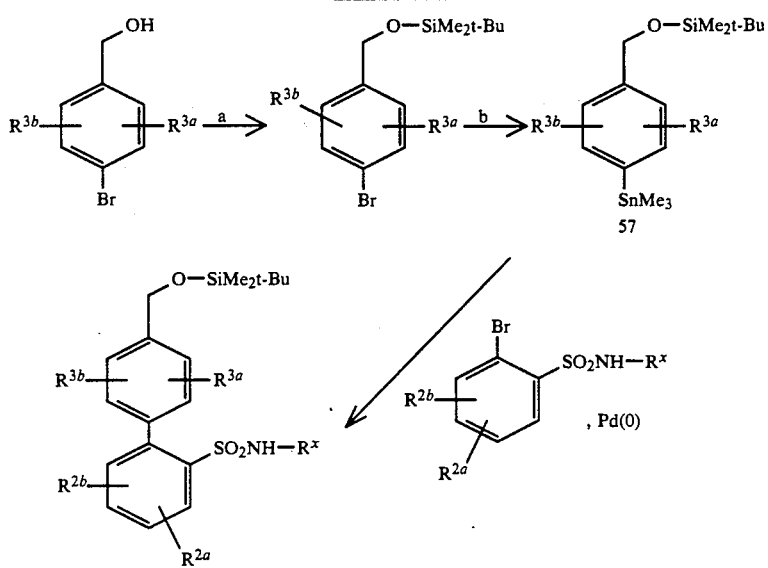

SCHEME 16
-continued
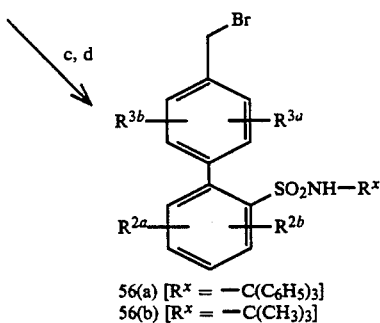
56(a) [$R^x = -C(C_6H_5)_3$]
56(b) [$R^x = -C(CH_3)_3$]
a. t-BuMe$_2$Si—Cl/Imidazole, DMF
b. t-BuLi, −78° C., Me$_3$SnCl
c. Tetrabutylammonium fluoride
d. CBr$_4$/Ph$_3$P.
SCHEME 17
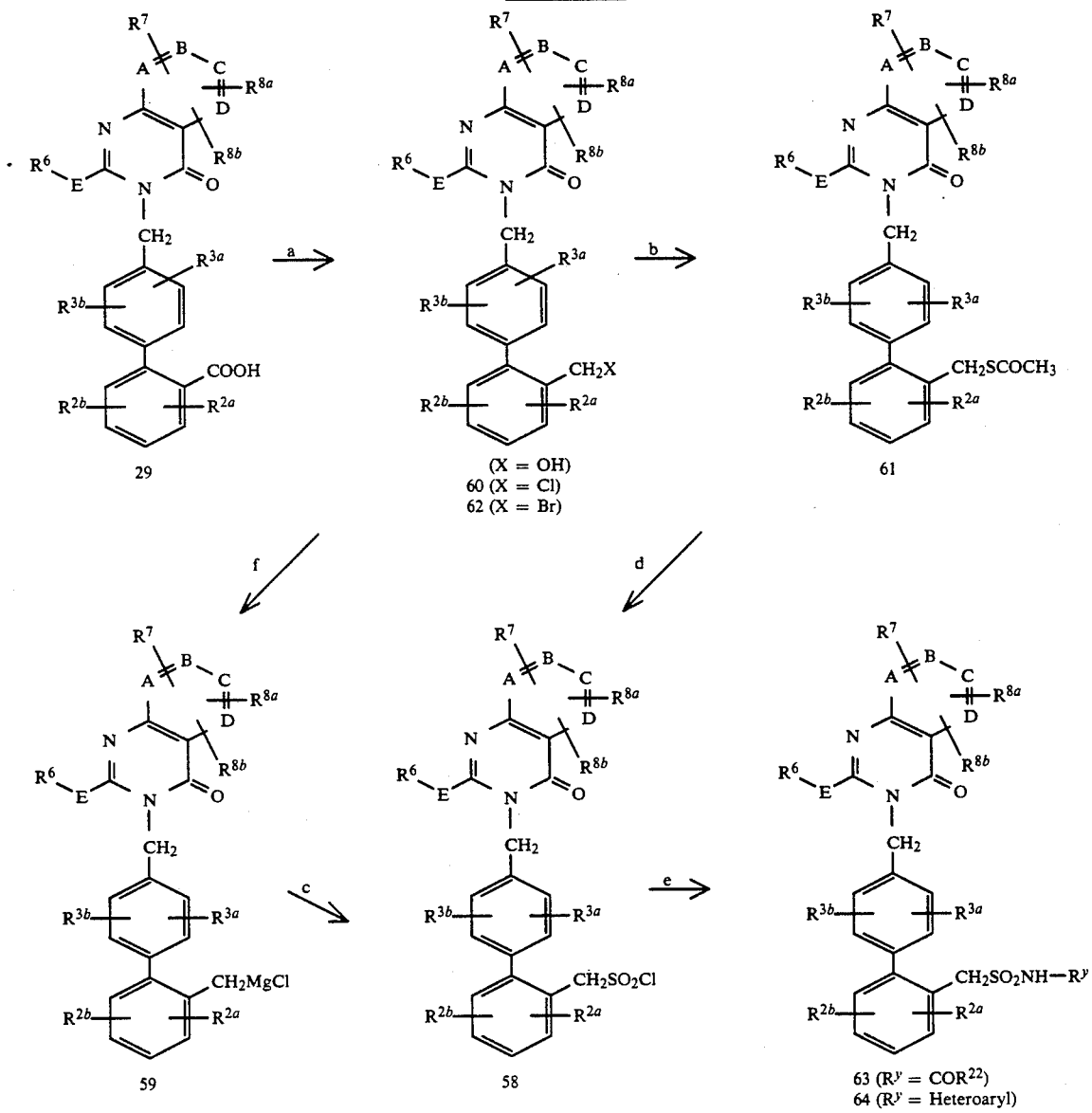
One of A, B, C, D is N and the others C

-continued
SCHEME 17 a. (i) EtOCOCl/Et$_3$N, THF, 0° C.
   (ii) NaBH$_4$
   (iii) CCl$_4$ or CBr$_4$/PPh$_3$
b. AcSK
c. SO$_2$Cl$_2$
d. Cl$_2$, AcOH, H$_2$O or,
   (i) SO$_2$Cl$_2$
   (ii) oxidation
e. R$^j$NH$_2$ or,
   (i) NH$_3$
   (ii) Acylation
f. Mg.

The compounds bearing R$^1$=—CH$_2$SO$_2$NHCOR$^{22}$ and —CH$_2$SO$_2$NHR$^{22}$ may be prepared as outlined in Scheme 17. The key precursor aryl-methanesulfonyl chloride 58 may be prepared either from the reaction of arylmethylmagnesium chloride 59, obtained from the corresponding benzyl chloride 60 and magnesium, or by oxidation of the aryl-methylthioacetate 61 (prepared from the benzyl bromide 62 with chlorine in presence of trace amount of water [Bagnay and Dransch, *Chem. Ber.* 93, 784 (1960)]. Alternatively, the aryl-methylthioacetate 61 can be oxidized with sulfuryl chloride in presence of acetic anhydride to form arylmethylsulfinyl chloride [S. Thea and G. Cevasco, *Tet. Lett.*, 28, 5193 (1987)], which can be further oxidized with appropriate oxidizing agents to give the sulfonyl chloride 58. The compounds 63 and 64 can be obtained by reacting the sulfonyl chloride 58 with appropriate amines.

Compounds where R$^1$=—NHSO$_2$NHR$^{22}$ may be prepared by the reaction of appropriate primary amines with the sulfamide 65 [S. D. McDermott and W. J. Spillane, *Synthesis*, 192 (1983)], as described in Scheme 18. The compound 65 may be obtained from the corresponding N-t-butylsulfamide 66 after treatment with anhydrous trifluoroacetic acid [J. D. Cart and W. L. Matier, *J. Org. Chem.*, 39, 566 (1974)]. The N-t-butylsulfamide 66 may be prepared by the reaction of the aromatic amine 67 (prepared as in Scheme 14) with t-butylsulfamoyl chloride [W. L. Matier, W. T. Comer and D. Deitchman, *J. Med. Chem.*, 15, 538 (1972)].

SCHEME 18

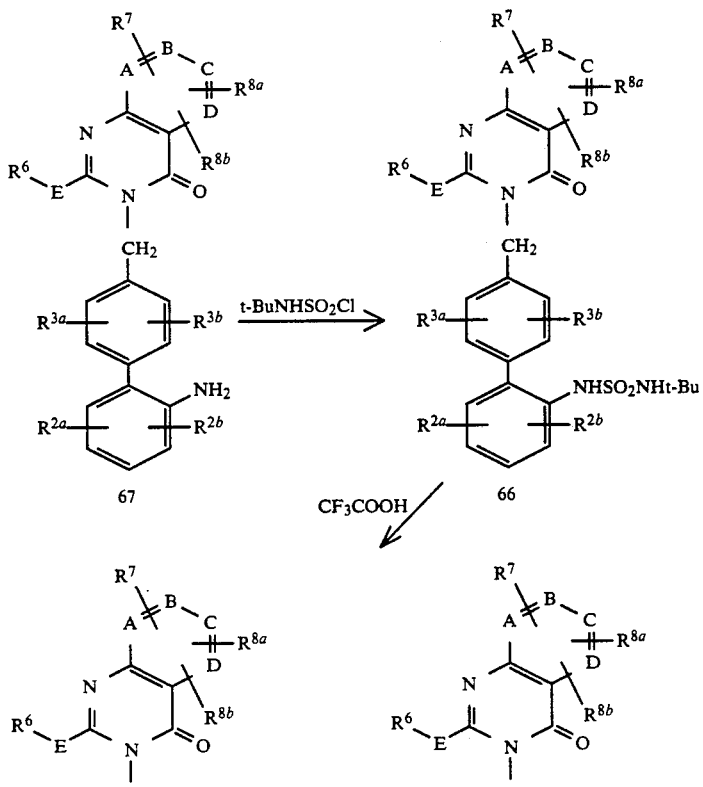

SCHEME 18

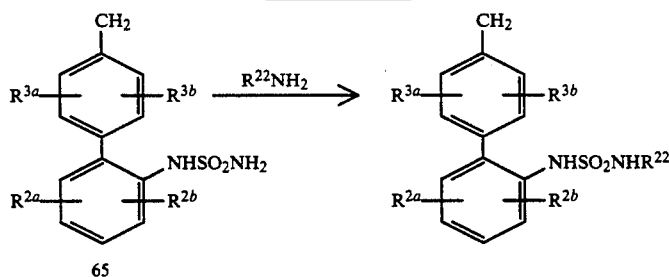

65

One of A, B, C, or D can be N and the others are C

Further functionalization of compounds of Formula 1 where $R^{8a}$ or $R^{8b}$ is nitro is available through the following route (Scheme 19). The nitro group of 68 may be reduced to the amine 69 by reduction with hydrogen over palladium on carbon. The amine may then be acylated with acid chlorides to give amides under basic conditions. The acylation of the amine with chloroformates is best carried out in the presence of sodium hydride to form the anilinium anion. This anion reacts quickly with chloroformates to give the carbamates 70. The carbamate may be isolated and then deprotonated with lithium hexamethyldisilazide and alkylated to give the N,N-dialkylated carbamates 71. Alternatively this process may be carried out in one pot by first preforming the anilinium anion, acylating it and then deprotonating in situ and alkylating with $R^4$ iodide group to give 71. The amine 69 reacts slowly with isocyanates to give ureas 72. Trisubstituted ureas 73 may be prepared from the benzyl carbamate 70 ($R^{22}$=benzyl) by treatment with the magnesium salt of a secondary amine. The trisubstituted ureas may be N-alkylated by deprotonation with lithium hexamethyldisilazide and alkylation with an $R^4$ iodide to give 74. The amine may be further derivatized or converted to other groups by means of chemical procedures well known to those skilled in the art.

SCHEME 19

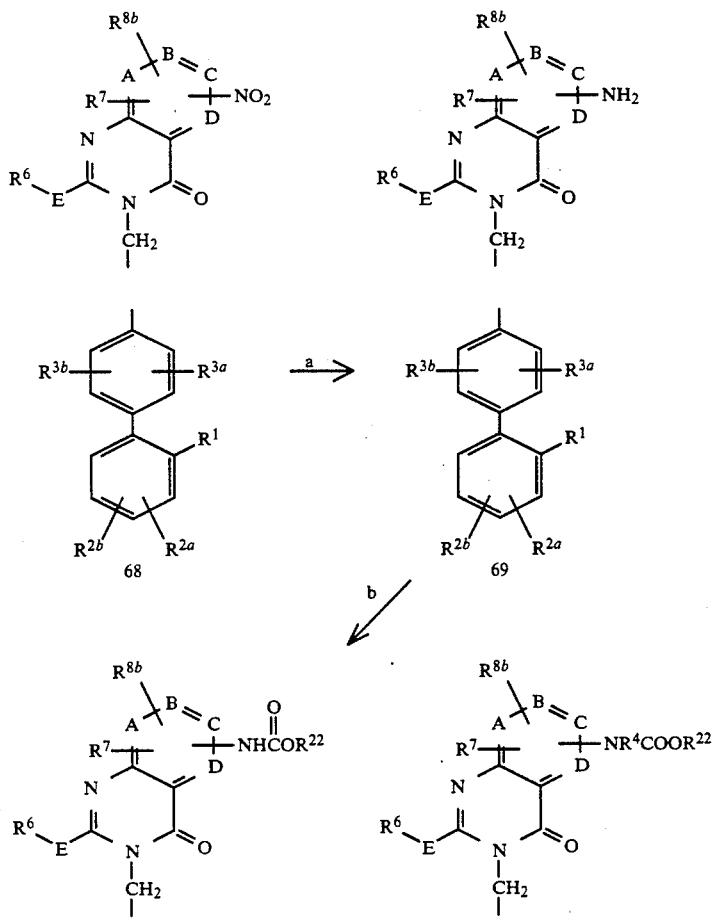

SCHEME 19
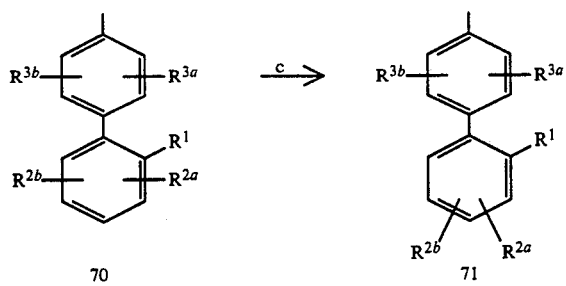
70 → 71
One of A, B, C or D is N and the others are carbon
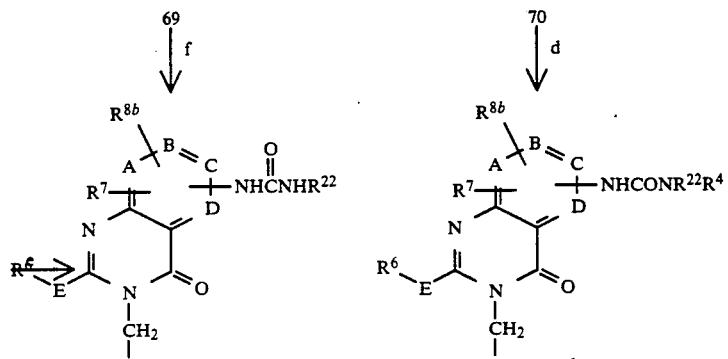
72    73
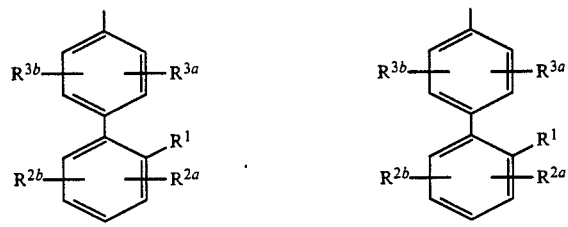
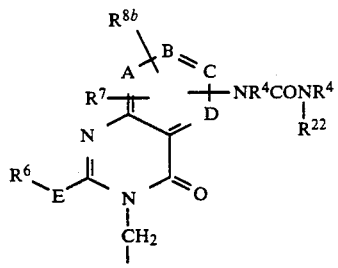
74
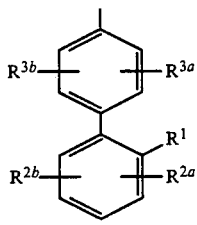
a. H₂, 10% Pd/C, EtAc
b. NaH, ClCOR²², DMF
c. LiN(TMS)₂, R⁴I

SCHEME 19

-continued d. MeMgBr, $R^4NHR^{22}$, THF, reflux
e. $LiN(TMS)_2$, $R^4I$, DMF
f. $R^{22}NCO$, $CH_2Cl_2$ Compounds of formula I where $R^1$ is

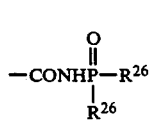

may be prepared from the corresponding carboxylic acid derivatives (I) as outlined in Scheme 20. The carboxylic acid (I), obtained as described in Scheme 2, can be converted into the corresponding amide by treatment with carbonyldiimidazole and then with ammonia. The resulting amide then can be treated with sodium hydride or n-butyllithium in THF at $-20°$ C. followed by an appropriately substituted phosphonyl or phosphinyl halide to form the desired compounds (30).

SCHEME 20

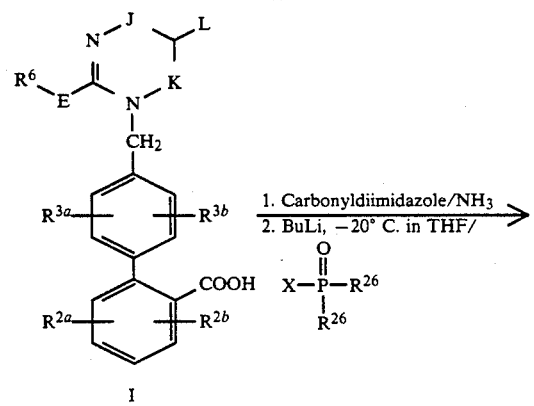

Compounds of formula I where $R^1$ is $-SO_2N-HSO_2R^{22}$ may be prepared from the key sulfonamide intermediate 42 as outlined in Scheme 21. The intermediate 42 may be prepared by the alkylation of appropriate heterocycles with the alkylating agent 5 as outlined in Scheme 2. Treatment of 76 with trifluoroacetic acid followed by acylation of the resulting sulfonamide 77 with appropriate sulfonyl chlorides may produce the desired compounds (79).

SCHEME 21

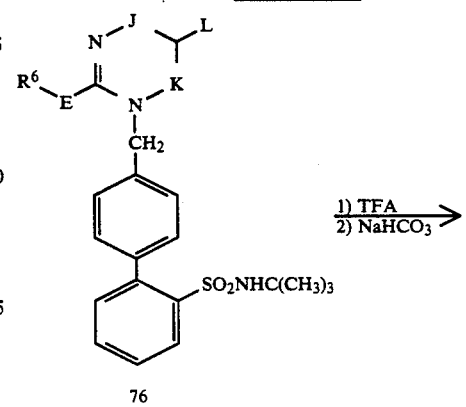

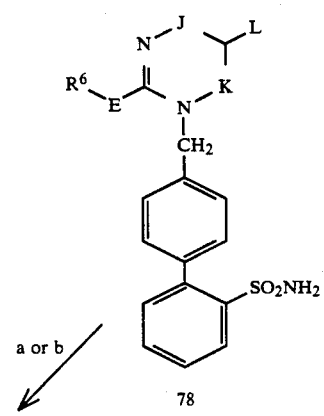

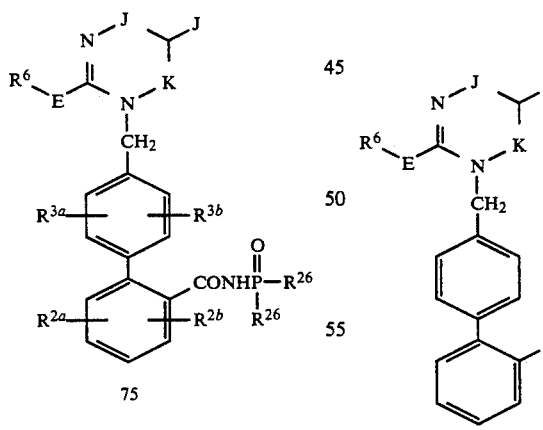

a. i) NaH/THF or DMF  (ii) $R^{22}SO_2Cl$
b. $R^{22}SO_2Cl$, DBU, THF

Compounds of Formula (I) wherein $R^1$ is $-SO_2NH-CO_2R^{22}$ may be prepared by reacting an appropriate chloroformate with the sulfonamide (78) in pyridine or in the presence of DBU in THF to afford the desired compound (80), as outlined in Scheme 22.

SCHEME 22

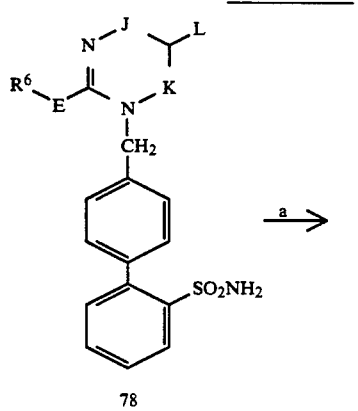

78

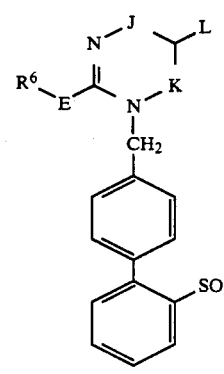

90 a. R²²OCCl, pyridine or DBU, THF

Compounds of Formula (I) wherein R¹ is

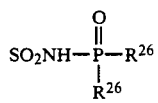

may be prepared by treating sulfonamide (78) with n-butyllithium in THF followed by the treatment of the resulting anion with an appropriately substituted phosphonyl or phosphinyl halide to form the desired compounds (91). (Scheme 23)

SCHEME 23

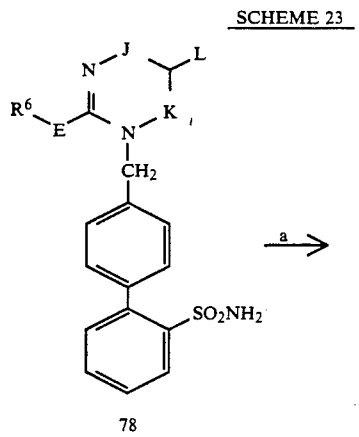

78

-continued
SCHEME 23

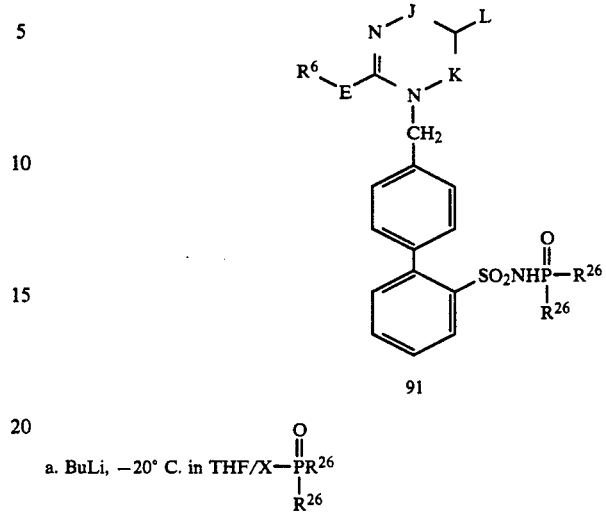

91 a. BuLi, −20° C. in THF/X—PR²⁶ (O, R²⁶)

Compounds of Formula (I) wherein R¹ is SO₂N-HSO₂N(R⁴)(R⁹) or

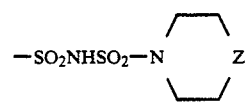

may also be prepared from sulfonamide (78) as outlined in Scheme 24. Treatment of 78 with n-butyllithium in THF at −25° C. and then with an appropriate sulfamoyl halide may produce the desired product (92) or (93).

SCHEME 24

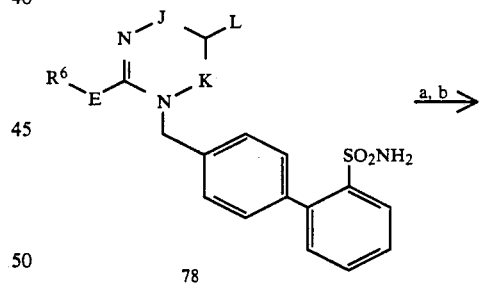

78

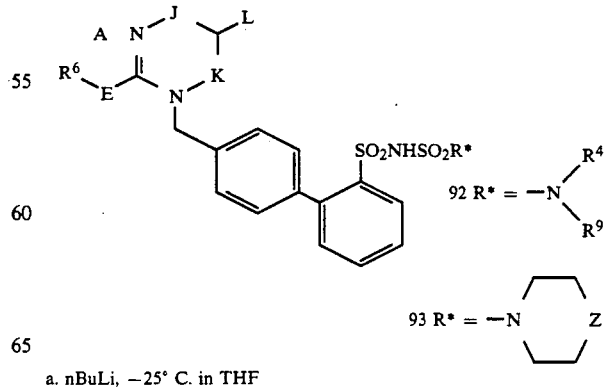

92 R* = —N(R⁴)(R⁹)

93 R* = —N⟨Z⟩ a. nBuLi, −25° C. in THF
b. R*SO₂Cl

Compounds of Formula (I) wherein $R^1$ is —NHSO$_2$NHSO$_2$R$^{22}$ or

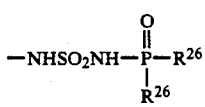

may be prepared from arylamine (95) as outlined in Scheme 25. The arylamine (95) obtained from the corresponding nitro compound 94 can be treated with t-butylsulfamoyl chloride to afford the protected amino sulfonamide (96). The amino sulfonamide (97) obtained after removal of the t-butyl protecting group may then be reacted with an appropriate acylating agent in the presence of a base such as pyridine or DBU in an organic solvent such as THF or DMF to form the desired products (98a) or (98b).

Compounds of the Formula (I) wherein $R^1$ is —NHSO$_2$R$^{22}$ may be prepared by the reaction of an appropriate sulfonyl halide (R$^{22}$SO$_2$Cl) or sulfonyl imidazole derivative with the aryl amine 95 in the presence of an appropriate base such as pyridine, triethylamine or DBU.

SCHEME 25

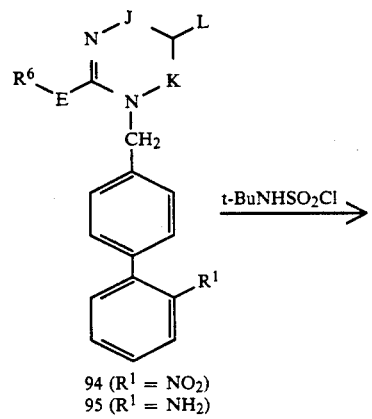

94 ($R^1 = NO_2$)
95 ($R^1 = NH_2$)

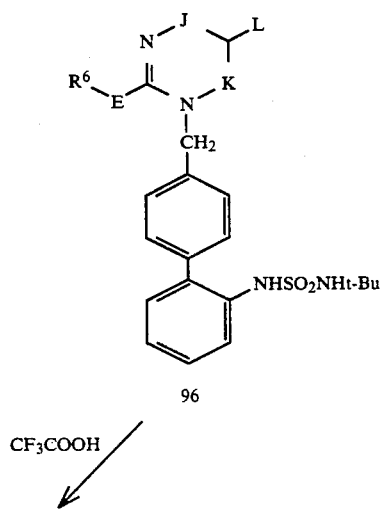

96

CF$_3$COOH

-continued
SCHEME 25

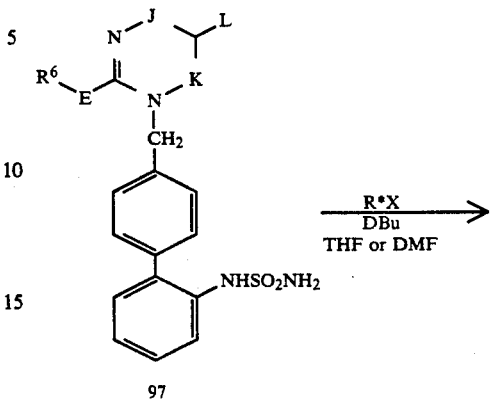

97

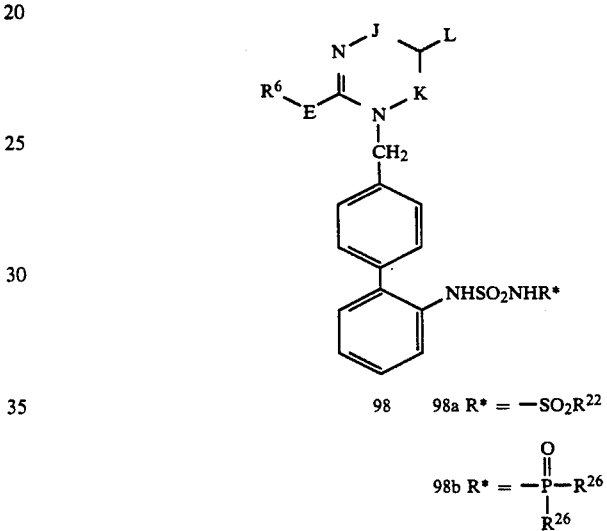

98    98a R* = —SO$_2$R$^{22}$

98b R* = —P(=O)(R$^{26}$)R$^{26}$

Compounds of Formula (I) and the benzyl halides of the formula (104) wherein $R^1$ is 1,2,3,5-oxathiadiazole-2-oxide may be prepared from the corresponding cyano derivative (99) or cyano precursor (8b) as outlined in Scheme 26 and 27, respectively utilizing procedures described in U.S. Pat. No. 4,910,019. The cyano derivatives (99), obtained as described in Scheme 2, can be converted into the corresponding amidoxime (100) by treatment with hydroxylamine hydrochloride and sodium methoxide in an organic solvent, such as methanol or DMSO. The amidoxime (100) then can be treated with base and thionyl chloride in an aprotic solvent to form the desired 1,2,3,5-oxathiadiazole-2-oxide (101). Similarly, the oxathiadiazole-2,2-dioxide 101a can be prepared by treatment of amidoxime 100 with a base and sulfuryl chloride. As shown in Scheme 26, the cyano precursor (8b) may be converted into the desired 1,2,3,5-oxathiadiazole (104) which is then protected with the trityl group prior to the formation of the desired benzyl halide (104). The protecting group is removed subsequent to the alkylation of heterocycle (1) to give the desired product 101).

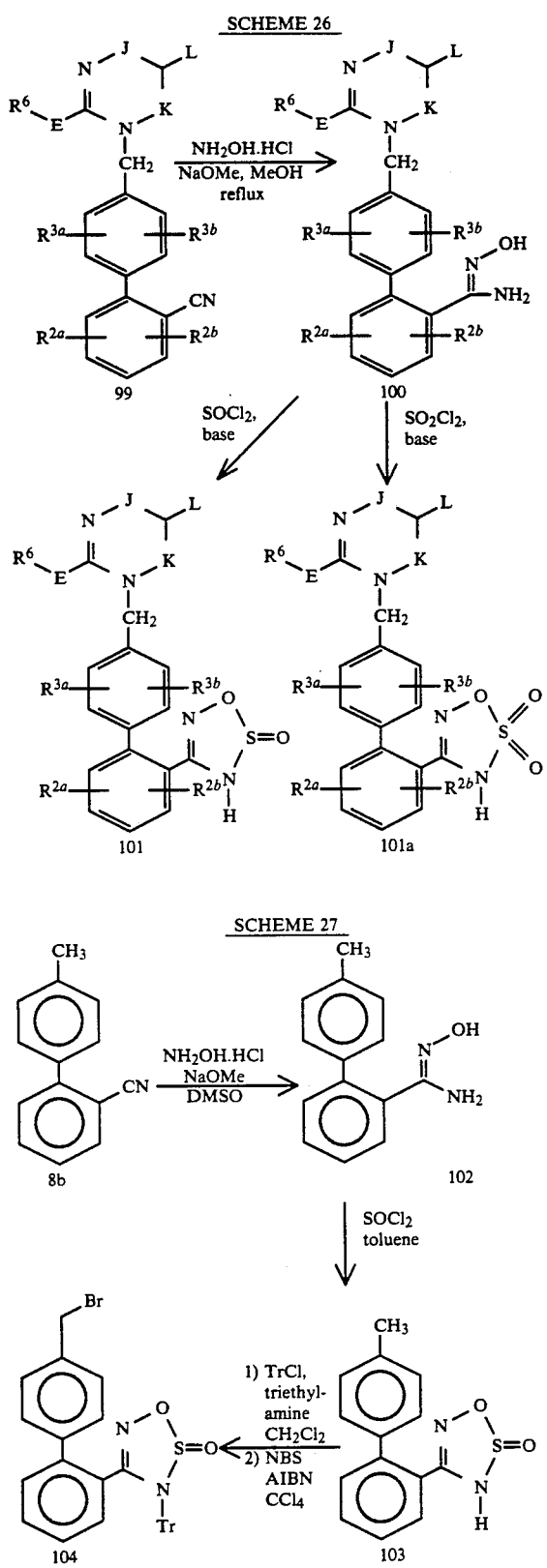

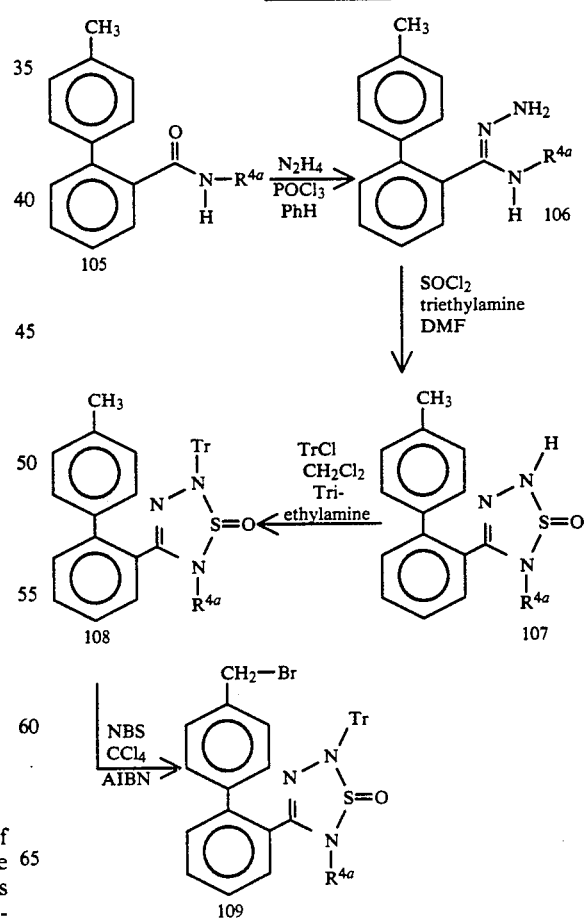

phenyl 8a according to the scheme illustrated (see procedures in U.S. Pat. No. 4,870,186), Intermediates (106) and (111) can be treated with SOCl$_2$ (see procedures in: *Ber. Deutsch. Chem. Ges.* 1971, 104 pp 639) to give intermediates, (107) and (112). Bromination of the N-protected compounds (107) and (112) provides intermediates 109 and 113 respectively. After alkylation with an appropriate heterocycle, the trityl group of the intermediate derived from 109 is removed with aprotic acid and the cyanoethyl group of the intermediate derived from 113 is removed upon treatment with hydroxide. Alternatively, (109) and (113) may be prepared as shown in Scheme 30 and 31. Treatment (110) with SOCl$_2$ ( see procedures in: *Ber. Deutsch. Chem. Ges.* 1971, 104 pp 639) provides (115), which under mild hydrolytic conditions provides (107). The conversion of (107) to (109) is as described for Scheme 28. Alkylation of the trityl protected analog (116) by treatment with a base such as NaH and an alkyl halide would provide (109), which then may be converted to (113) as previously described.

Compounds of Formula (I) and the benzyl halides of the formula (5) wherein R$^1$ is 1,2,3,5-thiatriazole-1-oxide may be prepared from the corresponding precursors 105 or 110 as outlined in Schemes 28 and 29, respectively, Intermediate 110 may be prepared from the bi-

SCHEME 29

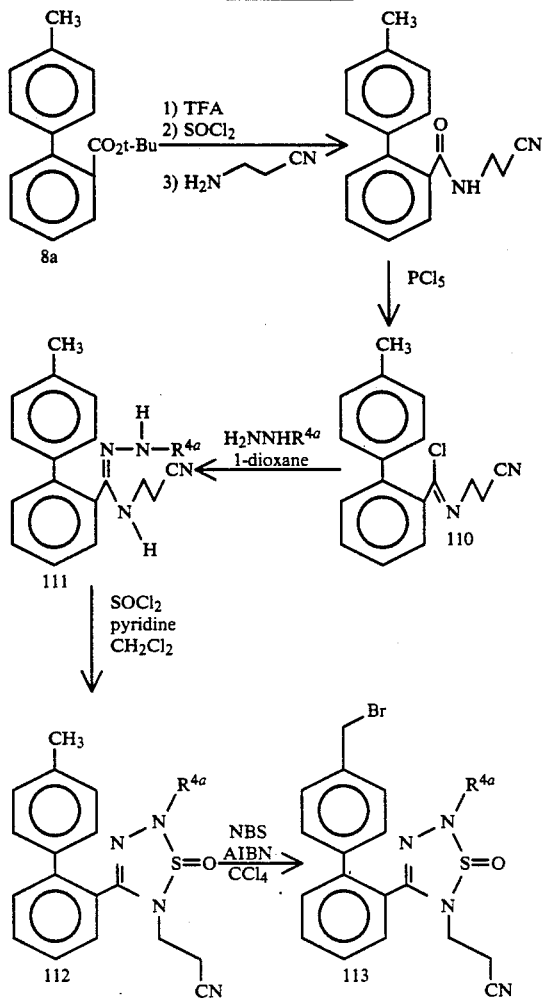

SCHEME 30

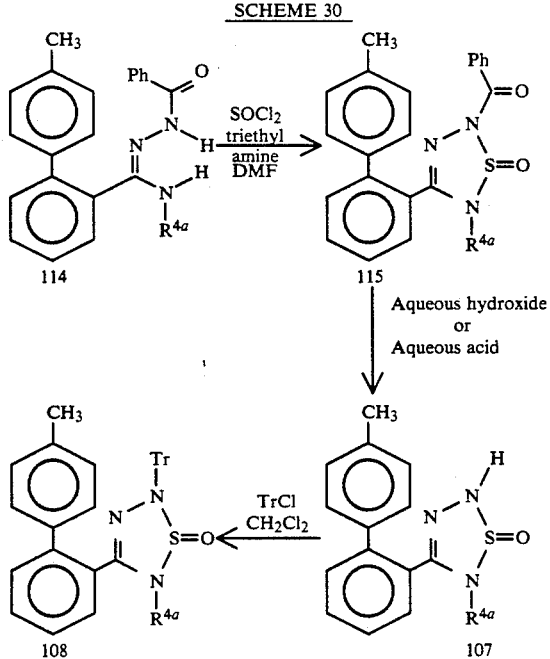

SCHEME 30 -continued

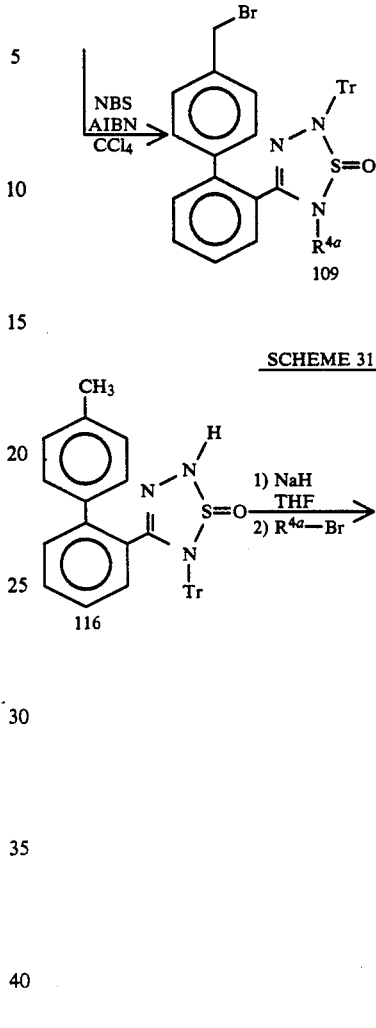

SCHEME 31

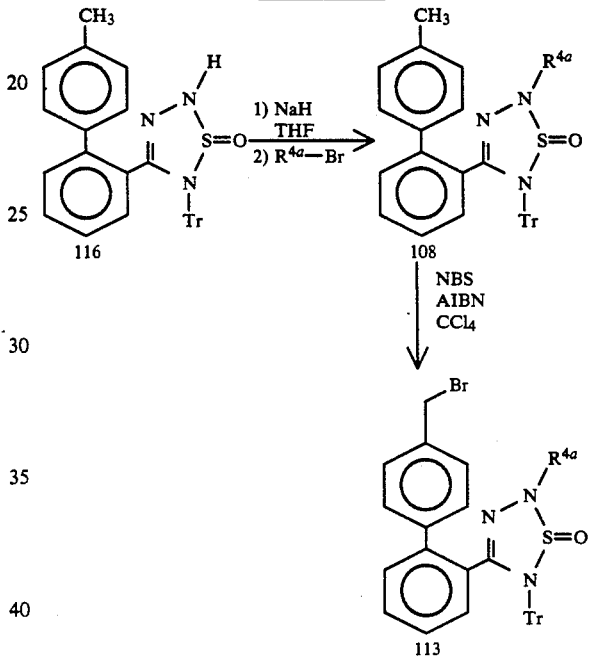

Compounds of Formula (I) and the benzyl halides of formula (5) wherein $R^1$ is 1,2,3,5-thiatriazole-1,1-dioxide-4-yl may be prepared using procedures described in *Monatsch. Chem.*, 1985, 116, pp 1321 and described herein. Sequential treatment of intermediates such as (110) or (106) with n-BuLi and $SO_2F_2$ will provide the 1,2,3,5-thiatriazol-1,1-dioxide analogs of (107) and (111). Further elaboration the aforementioned analogs by the methods described for the conversion of (107) to (111) in Scheme 28 and the methods described for the conversion of (111) to (113) in Scheme 29 would give the benzyl halides formula (5) wherein $R^1$ is 2-triphenylmethyl1 2,3,5-thiatriazole-1-dioxide-4-yl and 5-triphenylmethyl-1,2,3,5 -thiatriazole-1,1-dioxide-4-yl, respectively.

Compound of Formula (I) wherein $R^1$ is 3-oxo-1,2,4-thiadiazolidine-1,1-dioxide may be prepared from the nitro derivative (8c) as outlined in Scheme 32. The amino compound 117 obtained from 8c may be reacted with t-butyl sulfamoylchloride to form the intermediate 118, which then can be alkylated with an appropriate bromoacetic acid derivative to give 119. Treatment of 119 with trifluoroacetic acid followed by the treatment with an appropriate base such as sodium or potassium alkoxide may produce the desired compound 120, which can be elaborated further to give the key alkylating agent 122 as outlined in the scheme. Alkylation of an appropriate heterocyclic compound with 122 may then furnish the desired antagonist.

SCHEME 33

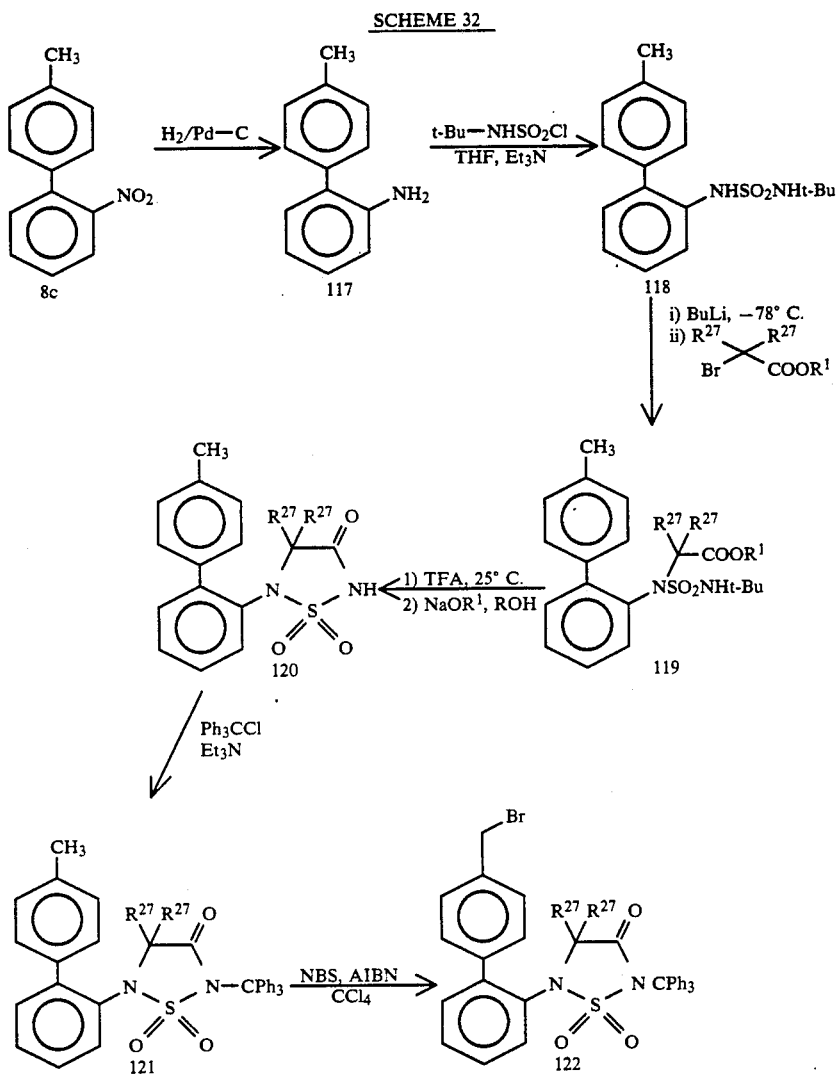

Compound of Formula (I) wherein $R^1$ is 5-aminosulfonyl-1,2,4-oxadiazole may be prepared using the bromomethyl biphenyl derivative 126 and appropriate heterocyclic compound. The synthesis of 126 can be accomplished as outlined in Scheme 33. The amidoxime 102 may be reacted with S-methylisothiourea to form the 5-amino-1,2,4-oxadiazole 123, which can be then treated with an appropriate sulfonylchloride to give the corresponding 5-aminosulfonyl-1,2,4-oxadiazole 124. The appropriately protected derivative 125 then can be brominated to form the desired alkylating agent 126.

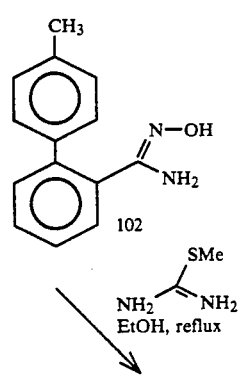

Compounds of Formula (I) wherein $R^1$ is 3-aminosulfonyl-1,2,4-oxadiazole can be prepared starting from the carboxylate derivative (8a) as outlined in Scheme 34. The ester derivative 127 obtained from 8a is treated with N-hydroxy guanidine sulfate in the presence of an alkoxide base to form the 3-amino-1,2,4-oxadiazole derivative 128, which may be reacted with an appropriate sulfonyl chloride to give the 3-aminosulfonyl-1,2,4-oxadiazole compound 129. The compound 130 can be prepared from 129 as outlined in Scheme 34.

Compounds of Formula (I) and the benzyl halides of formula (5) wherein $R^1$ is 1,2,3-oxathiazin-4(3H)-one-2,2-dioxide-6-yl may be prepared as outlined in Scheme 35. As shown and according to procedures in *Angew. Chem. Int. Edn.*, (1973), 12, pp 868, the beta ketoester (131) is treated with fluorosulphonyl isocyante, heated to extrude $CO_2$ and iso-butene, then treated with base such as KOH to form the oxathiazolinone dioxide intermediate (132). Treatment of (132) with triphenylmethyl chloride and triethylamine in $CH_2Cl_2$ gives (133) which in turn is converted to benzyl halide (134) by treatment with N-bromosuccinimide. AIBN, in $CCl_4$ at reflux.

SCHEME 35

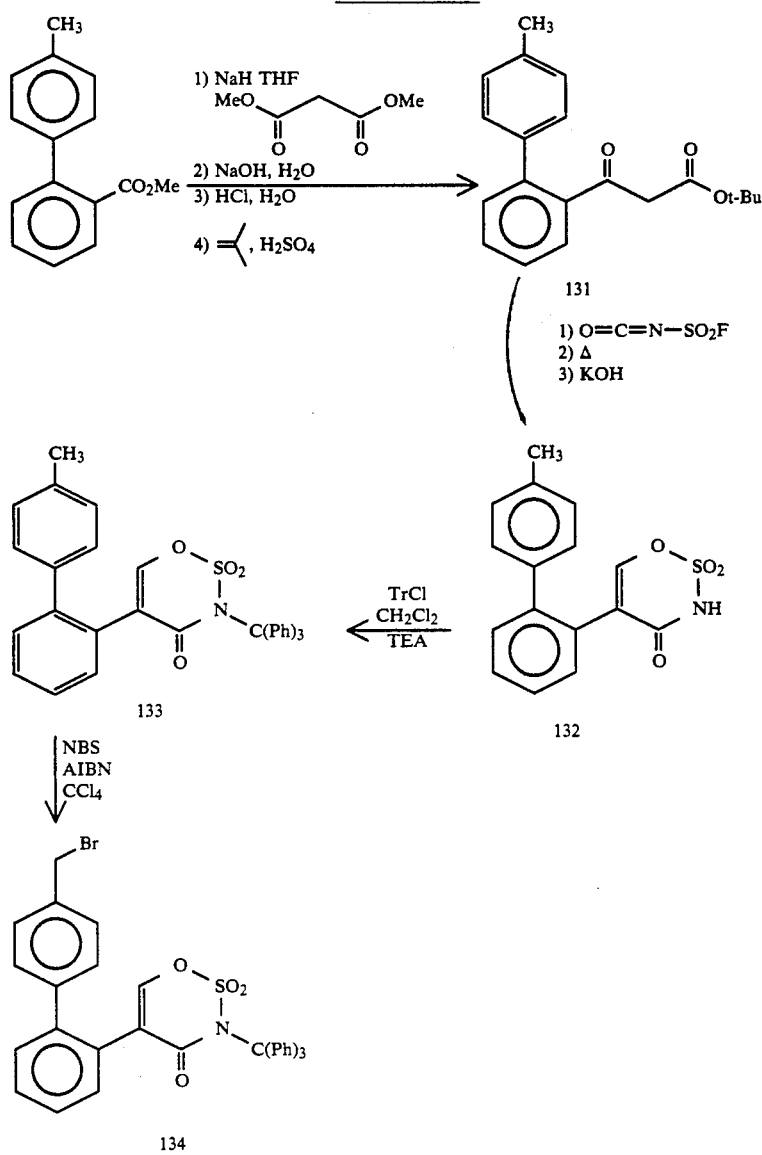

Compounds of Formula (I) wherein $R^1$ is oxamio acid may be prepared utilizing procedures described in *J. Ned. Chem.*, 1981, 24, pp 742-748 and as outlined in Scheme 36. The amine (95) is reacted with ethyl oxalyl chloride in the presence of a base such as pyridine or triethylamine and a solvent such as $CH_2Cl_2$ to form the intermediate oxalyl ester which as subsequently saponified with hydroxide to form oxamic acid (135).

SCHEME 36

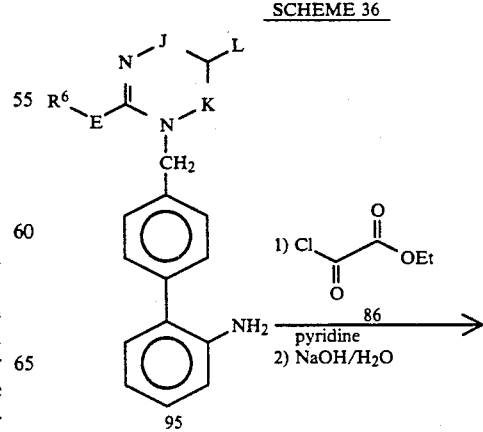

-continued
SCHEME 36

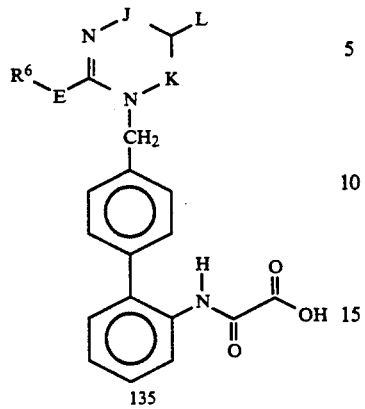

135

Compounds of Formula (I) wherein $R^1$ is —$SO_2NR^{25}OR^{25}$ may be prepared as outlined in Scheme 37. The key intermediate 137 is prepared by the reaction of an appropriate heterocyclic compound (1), preferably as an alkali metal salt, with the alkylating agent 136 (prepared from 57). The compound 139, prepared from the sulfonyl chloride 138 and O-t-butylhydroxylamine, is then reacted with 137 in the presence of a Pd(O) catalyst to give 140. Removal of the t-butyl protecting group produces the desired N-hydroxy sulfonamide 141.

SCHEME 37

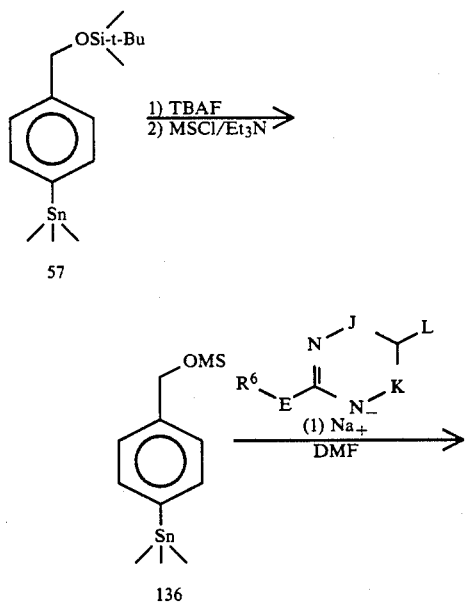

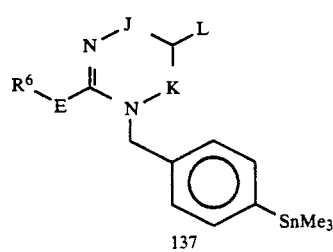

-continued
SCHEME 37

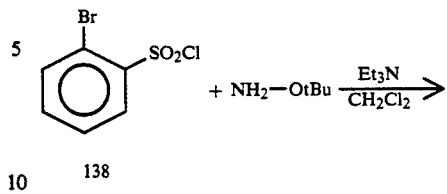

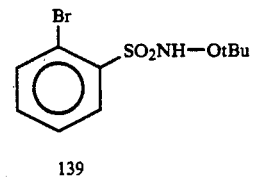

139

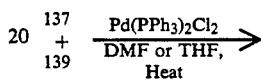

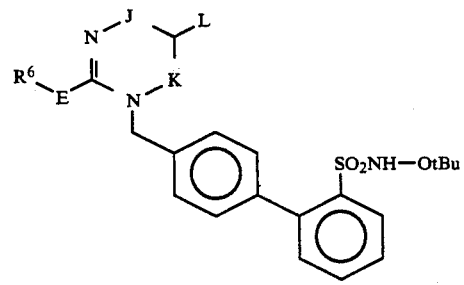

140

TFA
25° C.

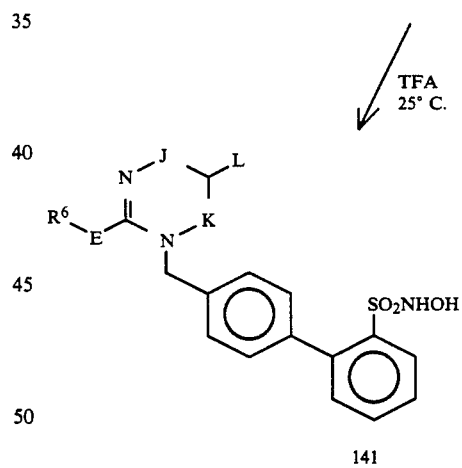

141

Substituted sulfonylcarbamates of structure 142 may be prepared by a variety of general routes as outlined in Scheme 38. The appropriate route should be chosen with regard to the relative ease of purification of intermediates as well as relative reactivity of the functional groups by one skilled in the art. In this scheme $R^{22}$ is generally a substituted or unsubstituted alkyl chain. This alkyl chain may be converted into another alkyl by heating with the requisite alcohol. $R^{29}$ is $R^{22}$ or $NR^4R^{22}$ of general structure as defined for $R^8$ in the generic description. The urea may be readily prepared utilizing method 2 or method 6 from the carboxybenzyl derivative.

SCHEME 38
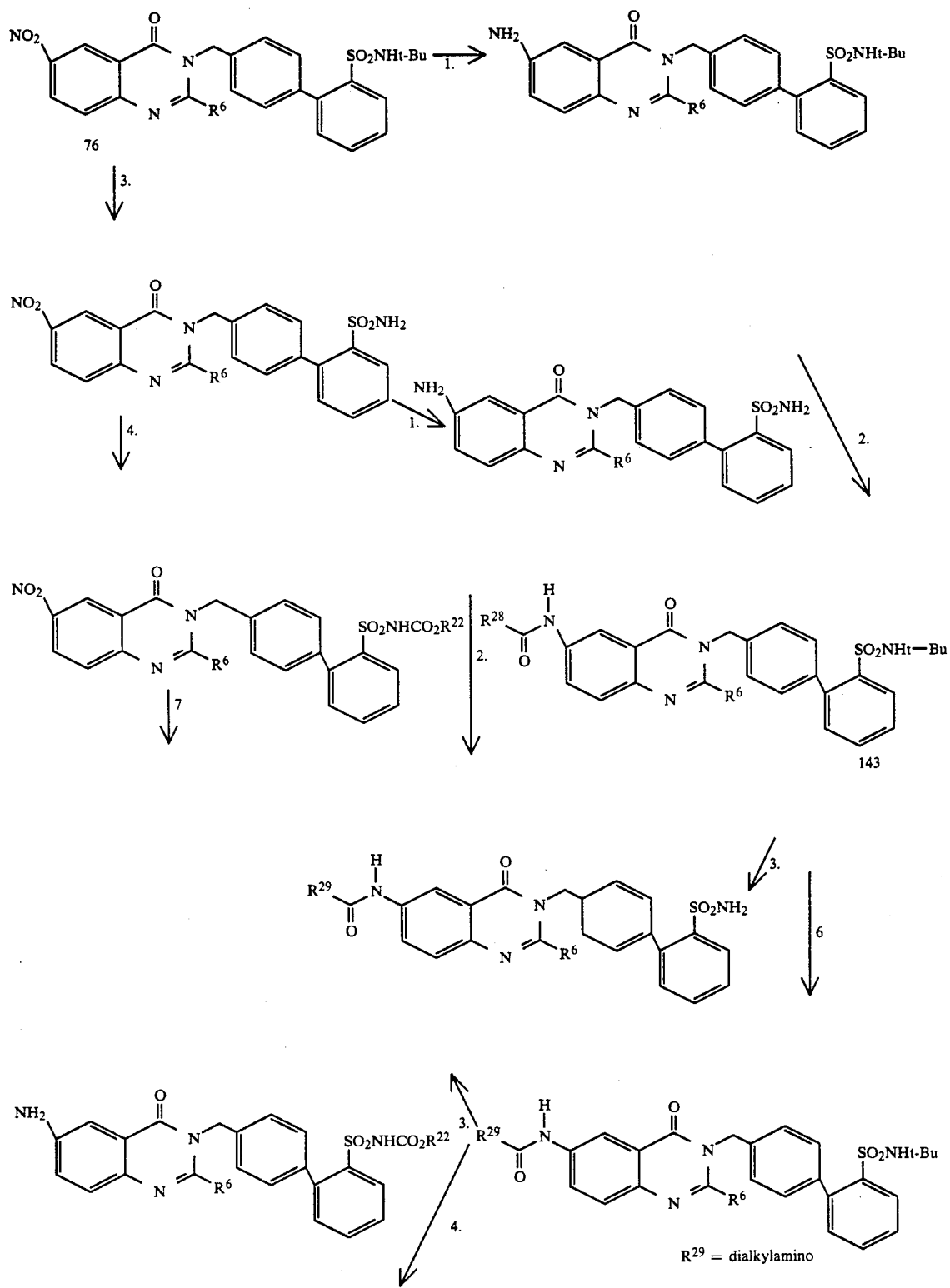

-continued
SCHEME 38

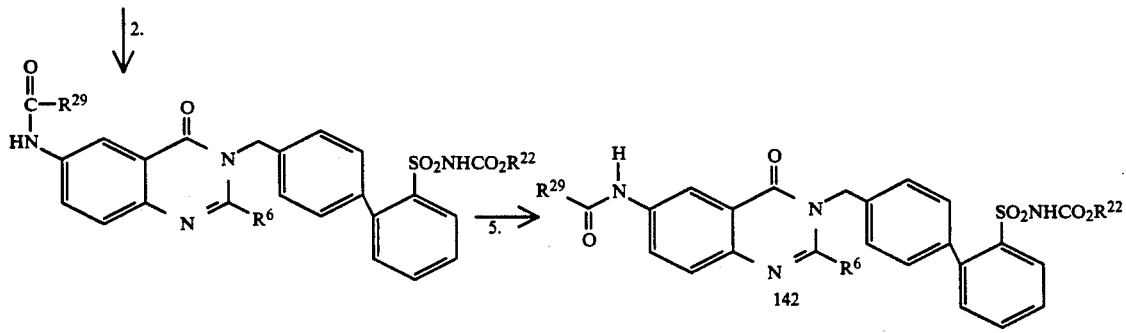

1. H₂, 10% Pd/C, dioxane
2. For amide: R²²COCl, Et₃N, CH₂Cl₂; for urea: R²⁸NCO, r.t.: for carbamate R²²ROCOCl, Et₃N, DMAP.
3. TFA
4. R²²OCOCl, pyridine, DMAP
5. R²²OH, heat
6. If R²² = OCH₂Ph in 143 then dialkylamino-NH, MeMgBr, THF, heat will convert carbamate to urea.

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

It also will be appreciated by those skilled in the art that the synthetic approaches to substituted pyridines and their transformation into substituted pyridopyrinidinones are considered obvious in the case of this work.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H₂SO₄, H₃PO₄, methane-sulfonic, toluensulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for: 30 minutes at 20,000 rpm at 4° C. The pellet thus obtained was resuspended in 30 ml of 50 mM Tris-5 mM MgCl₂ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added ¹²⁵I-Sar¹Ile⁸-angiotensin II [obtained from New England Nuclear] (10 μl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC₅₀) of potential AII antagonist which gives 50% displacement of the total specifically bound ¹²⁵I-Sar¹Ile⁸-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [Na₂HPO₄ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 μl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

Receptor assay using rat brain membrane preparation

Membranes from rat brain (thalamus, hypothamus and midbrain) were prepared by homogenization in 50 mM Tris HCl (pH 7.4), and centrifuged at 50,000 × g. The resulting pellets were washed twice in 100 mM NaCl, 5 mM $Na_2$·EDTA, 10 mM $Na_2HPO_4$ (pH 7.4) and 0.1 mM PMSF by resuspension and centrifugation. For binding assays, the pellets were resuspended in 160 volumes of binding assay buffer (100 mM NACl, 10 mM $Na_2HPO_4$, 5 mM $Na_2$·EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$,Ile$^8$-angiotensin II (23–46 pM) were added to duplicate tubes. The receptor membrane preparation (500 μl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

Using the methodology described above, representative compounds of the invention were evaluated and all were found to exhibit an activity of at least $IC_{50} < 10$ μM against the $AT_1$ and $AT_2$ subtype receptors thereby demonstrating and confirming the utility of the compounds of the invention as effective A II antagonists with "balanced" $AT_1/AT_2$ activity.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later, antagonists of formula (I) were administered intravenously or orally. Angiotensin II was then typically given at 5, 10, 15, 30, 45 and 60 minute intervals and every half hour thereafter for as long as the test compound showed activity. The change in the mean arterial blood pressure was recorded for each angiotensin II challenge and the percent inhibition of angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy, and in the management of vascular disorders such as migraine, Raynaud's disease, luminal hyperplasia, and to minimize the atherosclerotic process. The application of the compounds of this invention for these and similar disorders will be apparent to those skilled in the art.

The compounds of this invention are also useful to treat elevated intraocular pressure and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, tric hlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, reprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg),amiloride (5-20 mg), furosemide (5-80 mg), propranolol (20-480 mg), timolol maleate (5-60 mg. ), methyldopa (65-2000 mg), felodipine (5-60 mg), nifedipine (5-60 mg), and nitrendipine (5-60 mg). in addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and such are not to be considered as limiting the invention set forth in the claims appended hereto. All $^1$H-NMR spectra were recorded on a Varian XL-300 Fourier transform spectrometer. Chemical shifts are reported as (parts per million) downfield from tetramethyl silane. Mass spectra were obtained from the Merck and Co. mass spectral facility in Rahway N.J. Analytical TLC was conducted on E. M. Merck precoated silica plates (0.25 mm in glass, Kieselgel 60 $F_{254}$) with UV visualization. All chromatography was conducted on E. M. Merck silica gel. All reactions were carried out under an atmosphere of nitrogen under standard conditions for those skilled in the art.

PREPARATION OF INTERMEDIATES

2-Cyano-4'-methylbiphenyl

To a solution of p-bromotoluene (30 g) in dry ether (150 ml) at $-78°$ C., a solution of t-BuLi in pentane (1.7M) (210 ml) was added slowly over a period of 1.5 hours, using a dropping funnel. The bath was then removed and the mixture was stirred at room temperature for an additional 2 hours. The contents of the flask were then added slowly (using a cannula) at room temperature to a premixed solution of $ZnCl_2$ in ether (1M) (180 ml) and dry THF (360 ml). The mixture was stirred for 2 hours at that temperature and then the slurry was added (using a cannula) to a solution of 2-bromobenzonitrile (21.3 g) and $NiCl_2(Ph_3P)_2$ (2.1 g) in dry THF (300 ml). The mixture, after stirring at room temperature overnight (18 hours), was poured slowly while stirring into ice-cold 1N HCl (1500 ml). The organic layer was separated, and the aqueous phase was extracted with ether ($3\times300$ ml). The combined organic layer was washed with water, brine and then dried over $MgSO_4$. Removal of the solvent gave the crude product as a semisolid mass (34 g). The material was purified on a silica-gel flash column eluting with ethylacetatehexane (1:12) to give the desired nitrile as a low-melting solid (28 g, 88%). NMR ($CDCl_3$): 2.42 (s, 3H), 7.2-7.8 (m, 8H); FAB-MS: m/z 194 (M$^+$+1).

Trimethylstannylazide

To a concentrated solution of $NaN_3$ (1.2 kg, 18.5 moles) in water (3 L), a solution of trimethyltin chloride (600 g, 3 moles) in dioxane (400 ml) was added in three portions under vigorous stirring. A precipitate formed instantaneously. The mixture, after stirring overnight at room temperature, was filtered. The residue was washed with water, and dried under suction and then in vacuo over $P_2O_5$. Yield 541 g (88%), mp 120°-122° C.

5-[2-(4'-Methylbiphenyl)]tetrazole

To a solution of 2-cyano-4'-methylbiphenyl (390 g, 2.02 moles) in toluene (2.3 L) was added trimethyltin azide (525 g, 2.55 moles) at room temperature. The mixture was refluxed for 24 hours, cooled to room temperature, filtered, washed with toluene and sucked dry in a funnel. The precipitate was resuspended in toluene ( 3.5 L) and THF (250 ml) was added. Anhydrous HCl was bubbled in at a moderate rate at room temperature to give a clear solution (45 minutes). Addition of HCl gas was continued for another 20 minutes with stirring whereupon a white precipitate formed. The reaction mixture was stirred overnight. The solid product was filtered, washed with toluene followed with ether and then dried under vacuum. This produced 250 g of the tetrazole. (53% yield). m.p. 152°–154° C.; $^1$H-NMR (CDCl$_3$): 2.40 (s, 3H), 7.19 (dd, 1H), 7.55 (m, 2H), 8.25 (dd, 1H).

N-Triphenylmethyl-5-[2-(4'-methylbiphenyl)]tetrazole

To a cloudy solution of 250 g (1.06 mole) of 5-[2-(4'-methylbiphenyl)]tetrazole in CH$_2$Cl$_2$ (4 L) was added triphenylmethylchloride (310 g, 1.11 mole) at room temperature. The reaction mixture was stirred and triethylamine (190 ml, 138 g, 1.36 mole) was added portionwise. After addition, the mixture was stirred at reflux for 90 minutes. The solution was cooled to room temperature, washed with water (2×1 L) and dried over MgSO$_4$, filtered through a silica gel plug and concentrated on the rotovap to a solid. This was crystallized from toluene to give the product as an off-white solid (425 g, 84%); m.p. 166°–168° C.; $^1$H-NMR (CDCl$_3$): 2.28 (s, 3H), 6.9–7.05 (m, 10H), 7.2–7.5 (m, 12H), 7.9 (dd, 1H).

N-Triphenylmethyl-5-[2-(4'-bromomethylbiphenyl)]-tetrazole

To a solution of N-triphenylmethyl-5-[2-(4'-methylbiphenyl)]tetrazole (425 g, 0.89 moles) in CCl$_4$ (4.0 L) were added freshly opened N-bromosuccinimide (159 g, 0.89 mole) and dibenzoyl peroxide (22 g, 0.089 moles). The mixture was refluxed for 2 hours, cooled to room temperature and filtered. The filtrate was concentrated in vacuo to give a thick oil. The addition of ether (2.0 L) to this oil resulted in a clear solution which was followed by crystallization, filtration gave a white solid (367 g, 74%). m.p. 137°–139.5° C.; $^1$H-NMR (CDCl$_3$): 4.38 (s, 2H), 6.9–8.0 (m, 23H).

Preparation of
4'-Bromomethylbiphenyl-2-tert-butylsulfonamide

Step 1: 2-bromobenzene(tert-butyl)-sulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 h, then the mixture evaporated to dryness. Flash chromatography (silica gel, 10,15% ethyl acetate-hexane) afforded 2-bromobenzene(tertbutyl)sulfonamide as a white solid; $^1$H NMR (300 MHz, CDCl$_3$) δ8.18 (d, J=8.5 Hz, 1H), 7.50–7.35 (m, 5.11 (s, 1H), 1.20 (s, 9H).

Step 2: p-Tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 hours then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°–40° C., 1 mm Hg) which was further purified by flash chromatography (silica gel, hexane) to give p-tolyltrimethyltin as a colorless liquid; $^1$H NMR (300 MHz, CDCl3) δ7.40 (d, J=7.7 Hz, 2H), 7.19 (d, J=7.7 Hz, 2H), 2.34 (s, 3H), 0.30 (s, 9H).

Step 3: 4'-methylbiphenyl-2-tert-butylsulfonamide

2-Bromobenzene (tert-butyl)sulfonamide (1.00 g, 3.92 mmol), p-tolyl-trimethyltin (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 hours. The black suspension was cooled to room temperature, then filtered through a pad a celite which was washed with tetrahydrofuran. The colorless filtrate was evaporated to dryness then chromatographed (silica gel, 8,10% ethyl acetate-hexane) to give 4'-methylbiphenyl-2-tertbutylsulfonamide as a white solid; $^1$H NMR (300 MHz, CDCl3) δ8.16 (d, J=7.9 Hz, 1H), 7.60–7.37 (m, 4H), 7.36–7.24 (m, 3H), 3.57 (s, 1H), 2.42 (s, 3H), 0.99 (s, 9H).

Step 4:
4'-Bromomethylbiphenyl-2-tert-butylsulfonamide

N-Bromosuccinimide (0,387 g, 2.17 mmol), a,a'-azoisobutyronitrile (catalytic), 4'-methylbiphenyl-2-tert-butylsulfonamide (0.55 g, 1.81 mmol) and carbon tetrachloride (50 ml) were heated with stirring at reflux for 3 hours. After cooling to room temperature the mixture was filtered and the filtrate evaporated to dryness. Flash chromatography (silica gel, 10,20% ethyl acetate-hexane) afforded 4'-bromo-methylbiphenyl-2-tert-butylsulfonamide (77% pure (the remainder of the material was 4'-dibromomethylbiphenyl-2-tert-butyl-sulfonamide)) as a white solid.

$^1$H NMR (300 MHz, CDCl3) δ8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

EXAMPLE 1

2-propyl-6-(N-benzoyl-N-butyl)amino-3-(2'-(tetrazol-5-yl)biphen-4-yl)methylpyrido[3,2-d]pyrimidin-4(3H)-one Step 1:
2-(N-benzoyl-N-butyl)amino-5-nitro-6-cyanopyridine To a solution of 3.0 g (16 mmol) of 2-chloro-5-nitro-6-cyano-pyridine in 10 ml of dry DMF was added at 0° C. 2.18 g (21.6 mmol) of triethylamine followed by 1.4 g (18 mmol) of n-butyl amine. The reaction mixture was stirred for 5 hours, diluted with 100 ml of EtOAc and washed with water (3×10 ml). The aqueous phase was extracted with EtOAc (2×10 ml). The combined organic phases were washed with brine (1×30 ml) and dried over MgSO$_4$. The solution was filtered and the filtrate was concentrated in vacuo. The residue was purified by flash chromatography over silica gel eluting with 80% CH$_2$Cl$_2$/hexanes to give 2.43 g of the intermediate 2-butyl amine. The amine was dissolved in 10 ml CH$_2$Cl$_2$ and treated with triethyl amine 1.63 g (16.2 mmol) followed by 1.67 g (11.9 mmol) of benzoyl chloride and a catalytic quantity of DMAP.

The solution was filtered and the filtrate was concentrated in vacuo to give a solid residue which was triturated with 20 ml of 20% EtOAc hexanes to give 2.7 g of a brown solid. 57% yield overall.

$^1$H-NMR (CDCl$_3$-400 MHz): 0.88 (t, 3H, J=7.4 Hz), 1.31 (m, 2H), 1.68 (m, 2H), 4.15 (t, 2H, J=7.6 Hz), 7.37–7.51 (m, 6H), 8.26 (d, 1H, J=8.9 Hz).

Step 2:
2-(N-benzoyl-N-butyl)amino-5-(N-butanoyl)amino-6-cyano-pyridine 1.0 g (3.8 mmol) of 2-(N-benzoyl-N-butyl)amino-5-nitro-6-cyano-pyridine was hydrogenated in 20 ml of dioxane in the presence of 0.5 g raney nickel at atmospheric pressure. The reaction mixture was filtered and concentrated in vacuo. The residue was dissolved in 10 ml of $CH_2Cl_2$ and treated with 0.72 g (5.6 mmol) of diisopropylethyl amine and 0.39 g (3.7 mmol) of butyroyl chloride. The reaction mixture was stirred overnight and diluted with 20 ml of $CH_2Cl_2$. The solution was washed with water (2×20 ml) and brine (1×20 ml) and was dried over $MgSO_4$. The solution was filtered and the filtrate was concentrated in vacuo. The residue was purified by flash chromatography over silica gel eluting with 35% EtOAc/hexanes to give 1.0 g of an oil. 80% yield.

$H^1$-NMR ($CDCl_3$-200 MHz): 0.91 (t, 3H, J=7.2 Hz), 0.99 (t, 3H), J=7.3 Hz), 1.39 (m, 2H), 1.59–1.82 (m, 4H), 2.39 (t, 2H, J=7.7 Hz), 4.03 (t, 2H, J=7.3 Hz), 5.46 (bs, 1H), 7.02 (d, 2H, J=9.01 Hz), 7.18–7.35 (m, 4H), 7.50 (bs, 1H), 8.98 (d, 1H, J=9.01 Hz), 7.18–7.35 (m, 4H), 7.50 (bs, 1H), 8.98 (d, 1H, J=9.0 Hz).

Step 3:
2-propyl-6-(N-benzoyl-N-butyl)amino-pyrido-[3,2-d]pyrimidin-4(3H)-one To a solution of 0.1 g (0.3 mmol) of 2-(N-benzoyl-N-butyl)amino-5-N-butanoyl)amino-6-cyanopyridine in 1.5 ml of MeOH was added 0.33 ml (0.33 mmol) of 1N NaOH followed by 34 μl (0.33 mmol) of 30% $H_2O_2$ in water. The reaction mixture was heated to 90° C. for 2 hours. The reaction mixture was diluted with 10 ml of EtOAc and 10 ml of water. The aqueous phase was extracted with EtOAc (3×5 ml). The combined organic phases were washed with brine and dried over $MgSO_4$. The solution was filtered and the filtrate was concentrated in vacuo. The residue was purified by flash chromatography over silica gel eluting with 60% EtOAc/hexanes to give 0.058 g of a glass. 60% yield.

$H^1$-NMR ($CDCl_3$-400 MHz): 0.86 (t, 3H, J=7.2 Hz), 1.04 (t, 3H, J=7.4 Hz), 1.31 (m, 2H), 1.63 (m, 2H), 1.89 (m, 2H), 2.79 (t, 2H, J=7.9 Hz), 4.26 (t, 2H, J=7.4 Hz), 7.05 (d, 1H, J=8.7 Hz), 7.22 (d, 2H, J=7.7 Hz), 7.31 9 t, 1 H, J=7.4 Hz), 7.38 (d, 2H, J=7.07 Hz), 7.66 (d, 1H J=8.7 Hz).

Step 4:
2propyl-6-(N-benzoyl-N-butyl)amino-3-(2'-(N-triphenylmethyltetrazole-5-yl)biphen-4-yl)-methyl-pyrido[3,2-d]pyrimidin-4(3H)-one To a solution of 0.058 g (0.16 mmol) of the product of Step 3 in 1 mL of DMF at 0° C. was added, under nitrogen, 0.17 mL of a 1M solution of sodium hexamethyl disilazide in THF. After 30 minutes a solution of N-triphenylmethyl-5-[2-(4'-bromomethylbiphenyl)] tetrazole dissolved in 1 mL of DMF was added. The reaction mixture was stirred overnight diluted with 25 ml of EtOAc and washed with water (3×5 ml) followed by brine (1×5 mL) and dried over $MgSO_4$. The suspension was filtered and the filtrate was concentrated in vacuo and the residue was purified by flash chromatography over silica gel eluting with 35% EtOAc/hexanes to give the title compound.

$H^1$-NMR ($CDCl_3$-200 MHz): 0.89 (t, 3H), 0.93 (t, 3H), 1.38 (m, 2H), 1.71 (m, 4H), 2.62 (t, 2H), 4.32 (m, 2H), 5.31 (bs, 2H), 6.91 (m, 4H), 7.08 (m, 4H), 7.21–7.37 (m, 4H), 7.39–7.51 (,m, 4H), 7.63 (d, 1H), 7.93 (dd, 1H).

Step 5:
2-propyl-6-(N-benzoyl-N-butyl)amino-3-(2'-tetrazol-5-yl)biphen-4-yl)methylpyrido-[3,2-d]pyrimidin-4(3H)-one Hydrolysis of the product of Step 4 was accomplished by stirring with 2 mL of 3:1:1 acetic acid:water:THF at room temperature overnight. The reaction mixture was concentrated in vacuo and the residue was purified by flash chromatography over silica gel eluting with 70: 30:1 EtOAc:hexanes:acetic acid to give the title compound.

$H^1$ NMR ($CDCl_3$-400 MHz): 0.80 (t, 3H, J=7.4 Hz), 0.97 (t, 3H, J=7.4 Hz), 0.97 (t, 3H, J=7.4 Hz), 1.21 (m, 2H), 1.52 (m, 2H), 1.79 (m, 2H), 2.72 (t, 2H, J=7.7 Hz), 5.32 (bs, 2H), 7.01 (d, 1H, J=8.8 Hz ), 7.08–7.23 (m, 7H), (d, 2H, J=7.3 Hz), 7.37 (d, 1H, J=7.7 Hz), 7.45 (t, 1H, J=6.8 Hz), 7.54 (t, 1H, J=6.8 Hz), 7.61 (d, 1H, J=8.7 Hz), 7.86 (d, 1H, J=7.7 Hz).

EXAMPLE 2
2-propyl-6-(2-pyridyl)-3-[2'-(N-butyloxycarbonylsulphonamido)-biphenyl-4-yl)methyl]pyrido-[3,2-d]pyrimidin-4(3H)-one Step 1: 2-chloro-5-(N-butyroylamino-6-cyano pyridine To a suspension of 1.0 g (6.5 mmol) of 2-chloro-5-(N-butyroyl)amino-6-cyano-pyridine in 8 ml of dry chloroethane was added 1.39 g (13 mmol) of diisopropylethyl amide followed by 0.86 g (28.1 mmol) of butyroyl chloride and a catalytic quantity of DMAP. Two products of less polar rf formed. The quantity of acylating agent and tertiary amine was doubled and the reaction mixture was heated at 65° C. overnight. The reaction mixture was diluted with 50 ml of $CH_2Cl_2$ and washed with 1N NaOH (2×10 ml). The product was dried over $MgSO_4$, filtered and concentrated in vacuo. The residue was purified by flash chromatography over silica gel eluting with 20% EtOAc/hexanes to give 1.42 g of the imide. The product was stirred in 20 ml of MeOH in presence of 5.8 ml of 1N NaOH solution for 30 minutes. The reaction mixture was concentrated in vacuo and the aqueous suspension was extracted into EtOAc (3×20 ml) after diluting the reaction mixture with 20 ml of water. The combined organic extracts were washed with water (1×20 ml ) and brine (1×20 ml) and dried over $MgSO_4$. The solution was filtered and concentrated in vacuo and the residue was purified by flash chromatography over silica gel eluting with 15% EtOAc/hexanes to give 0.8 of an off white glass.

$H^1$-NMR ($CDCl_3$-400 MHz): 1.01 (t, 3H, J=7.3 Hz), 1.76 (m, 2H), 2.45 (t, 2H, J=7.3 Hz), 7.49 (d, 1H, J=9.1 Hz), 7.74 (bs, 1H), 8.81 (d, 1H, J=9.1 Hz ).

Step 2: 2-propyl-6-chloro-pyrido [3,2-d]pyrimidin-4(3H)one

To a solution of 0.56 g (2.5 mol) of 2-chloro-5-(N-butyroyl)amino-6-cyano-pyridine in 5 ml of MeOH was added 2.78 ml (5.56 mmol) of 2N NaOH followed by 0.33 ml (5.0 mmol) of 30% $H_2O$. The reaction mixture was diluted with 10 ml of water and acidified with acetic acid. The mixture was extracted with EtOAc (3×20 ml). The combined organic phases were washed with brine and dried over $MgSO_4$. The solution was filtered and the filtrate was concentrated in vacuo. The residue was recrystallized from MeOH to give 0.35 g of pale yellow needles. mp: 264°–266° C.

H-NMR (CDCl$_3$-400 MHz): 1.02 (t, 3H, J=7.37 Hz), 1.88 (m, 2H), 2.83 (t, 2H, J=7.4 Hz), 7.64 (d, 1H, J=8.6 Hz), 7.96 (d, 1H, J=8.6 Hz), 12.45 (bs, 1H).

Step 3:
2-propyl-5-chloro-3-[2'-(t-butylsulphonamido)-biphenyl-4-yl)methyl]pyrido[3,2-d]-pyrimidin-4-(3H)-one 2-propyl-6-chloro-pyrido[3,2-d]pyrimidin-4(3H)-one was alkylated with 4'-bromomethylbiphenyl-2-t-butylsulphonamide as in the manner described above in Example 1, Step 4 to give, following purification by flash chromatography over silica gel eluting with 50% EtOAc/hexanes, 0.36 g of a white powder. 62% yield.

H$^1$-NMR (CDCl$_3$-200 MHz): 0.96 (s, 9H), 1.02 (t, 3H, J=7.3 Hz), 1.82 (m, 2H), 2.77 (t, 3H, J=7.8 Hz), 5.48 (bs, 2H), 7.21–7.35 (m, 3H), 7.42–7.53 (m, 4H), 7.64 9d, 1H, J=8.6 Hz), 7.95 (d, 1H, J=8.6 Hz), 8.14 (dd, 1H, J=1.7, 7.5 Hz).

Step 4:
2-Propyl-6-(2-pyridyl)-3-[2'-(t-butylsulphonamido)-biphen-4-yl)methyl-]pyrido [3,2-d]pyrimidin-4(3H)-one To a solution of 0.05 g (0.095 mmol) of 2-propyl-6-chloro-3-[2'-(t-butylsulphonamido)-biphen-4-yl)methyl-]pyrido [3,2-d]pyrimidin-4(3H)-one in 1 ml of dry DMF was added 27.5 mg (0.11 mmol) of 2-trimethylstannylpyridine followed by a catalytic quantity of bistriphenylphosphine palladium dichloride. The reaction mixture was heated at 100° C. for 1 hour at which time the mixture turned black. The reaction mixture was filtered through a silica pad after diluting with 5 ml of EtOAc. The filtrate was concentrated in vacuo and the residue was purified by Chromatotron eluting with 4% MeOH/CH$_2$Cl$_2$. Recovered 31.7 mg of a white solid. 59% yield.

H$^1$-NMR (CDCl$_3$-200 MHz): 0.98 (s, 9H), 1.05 (t, 3H, J=7.3 Hz), 1.89 (m, 2H), 2.80 (t, 2H, J=7.3Hz), 5.53 (bs, 2H), 7.2.1–7.55 (m, 9H), 7.85 (dt, 1H, J=1.7, 9.3 Hz), 8.12 (m, 2H), 8.70 (m, 1H), 8.87 (d, 1H, J=8.7 Hz).

Step 5:
2-Propyl-6-(2-pyridyl)-3-[2'-(N-butyloxycarbonylsulphonamido)-biphenyl-4-yl)methyl]pyrido[3,2-d]-pyrimidin-4(3H)-one 31.7 mg of 2-propyl-6-(2-pyridyl)-3-[2'-(t-butylsulphonamido)-biphenyl-4-yl)methyl]pyrido[3,2-d]-pyrimidin-4(3H)-one was stirred overnight with 1 ml of TFA and 0.1 ml of anisole. The reaction mixture was concentrated in vacuo and the intermediate sulphonamide was dissolved in 1 ml of anhydrous pyridine. The reaction mixture was treated with an excess of butylchloroformate and a catalytic quantity of DMAP. The solution was stirred for 3 days, concentrated in vacuo. The residue was purified by Chromatotron over silica gel eluting with 4% MeOH/CH$_2$Cl$_2$. To give 13.1 mg of a white powder.

H$^1$-NMR (CDCl$_3$-200 MHz): 0.78 (t, 3H, J=7.4 Hz), 1.01 (t, 3H, J=7.2 Hz), 1.13 (m, 2H), 1.42 (m, 2H), 1.82 (m, 2H), 2.77 (t, 2H, J=7.4 Hz), 3.95 (t, 2H, J=6.6 Hz), 7.21–7.32 (m, 5H), 7.53 (dt, 1H, J=1.4, 7.5 Hz), 7.59 (dt, 1H, J=1.4, 7.5 Hz), 7.93 (dt, 1H, J=1.8, 7.7 Hz), 8.08 (d, 1H, J=8.6 Hz), 8.23 (dd, 1H, J=7.9, 1.3 Hz), 8.50 (m, 1H), 8.67 (m, 1H), 8.70 (d, 1H, J=7.99 Hz), 8.82 (d, 1H, J=8.7 Hz).

EXAMPLE 3

Typical Pharmaceutical Compositions Containing a Compound of the Invention

A. Dry Filled Capsules Containing 50 mg of Active Ingredient Per Capsule

| Ingredient | Amount per capsule (mg) |
|---|---|
| 2-propyl-6-(N-benzoyl-N-butyl)amino-3-(2'-tetrazol-5-yl)biphen-4-yl)-methylpyrido[3,2-d]pyrimidin-4(3H)-one | 50 |
| Lactose | 149 |
| Magnesium stearate | 1 |
| Capsule (size No. 1) | 200 |

The 2-propyl-6-(N-benzoyl-N-butyl)amino-3-(2'-tetrazol-5-yl)biphen-4-yl) methyl]pyrido[3,2-d]-pyrimidin-4(3H)-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-propyl-6-(N-benzoyl-N-butyl)amino-3-(2'-tetrazol-5-yl)-biphen-4-yl)methylpyrido[3,2-d]pyrimidin-4-(3H)-one (25 mg), pregelatinized starch USP (82 mg), microcrystalline cellulose (82 mg) and magnesium stearate (1 mg).

C.: Combination Tablet

A typical combination tablet would contain, for example, a diuretic such as hydrochlorothiazide and consist of 2-propyl-6-(N-benzoyl-N-butyl)amino-3-(2'-tetrazol-5-yl)-biphen-4-yl)methylpyrido[3,2-d ]pyrimidin-4-(3H)-one (50 mg) pregelatinized starch USP (82 mg), microcrystalline cellulose (82 mg) and magnesium stearate (1 mg).

D: Suppository

Typical suppository formulations for rectal administration can contain 2-propyl-6-(N-benzoyl-N-butyl)amino-3- (2'-tetrazol-5-yl)-biphen-4-yl)methylpyrido[3,2-d ]pyrimidin-4-(3H)-one (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another anti-hypertensive and/or a diuretic and/or an a calcium angiotensin converting enzyme and/or a calcium channel blocker in pharmaceutically effective amounts as described, for example, in C above.

E: Injection

A typical injectible formulation would contain 2-propyl-6-(N-benzoyl-N-butyl)amino-3- (2'-tetrazol-5-yl)-biphen-4-yl)methylpyrido[3,2-d ]pyrimidin-4-(3H)-one sodium phosphate dibasic anhydrous (11.4 mg) benzylalcohol (0.01 ml ) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of formula (I):

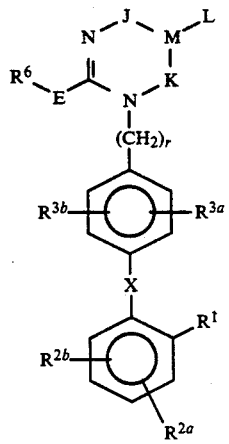

(I)

or a pharmaceutically acceptable salt thereof wherein:

M is a C atom;

L is C or N when connected to K or J to form a ring as defined below;

J is —C(=Y)-where Y is O or $NR^{21}$ and K and L are connected together to form a 6 membered aromatic ring containing one N atom that is not at K and five C atoms which can be substituted at the carbon atoms with $R^{8a}$ and $R^{8b}$;

K is —C(=Y)- where Y is O or $NR^{21}$ and J and L are connected together to form a 6 membered aromatic ring containing one N atom that is not at J and five C atoms which may be substituted at the carbon atoms with $R^{8a}$ and $R^{8b}$ provided that only one of J and K is —C(=Y)—;

$R^1$ is (a) —$CO_2R^4$,
(b) —$SO_3R^5$,
(c) —$NHSO_2CF_3$,
(d) —$PO(OR^5)_2$,
(e) —$SO_2$—NH—$R^9$,
(f) —$CONHOR^5$,

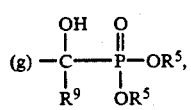

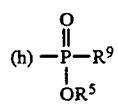

(i) —$SO_2NH$-heteroaryl as defined below,
(j) —$CH_2SO_2NH$-heteroaryl as defined below,
(k) —$SO_2NH$—CO—$R^{22}$,
(l) —$CH_2SO_2NH$—CO—$R^{22}$,
(m) —$CONH$—$SO_2R^{22}$,
(n) —$CH_2CONH$—$SO_2R^{22}$,
(o) —$NHSO_2NHCO$—$R^{22}$,
(p) —$NHCONHSO_2$—$R^{22}$,

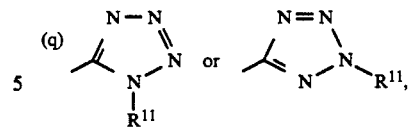

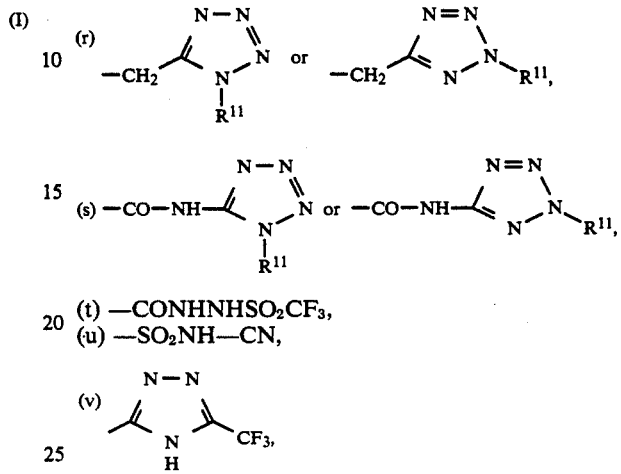

(t) —$CONHNHSO_2CF_3$,
(u) —$SO_2NH$—CN,

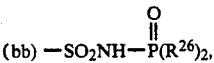

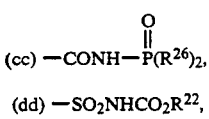

(x) —$PO(OR^5)(OR^4)$,
(y) —$SO_2NHCONR^4R^{22}$,
(z) —$SO_2N(R^{25})$—$OR^{25}$,
(aa) —$SO_2NHSO_2R^{22}$,

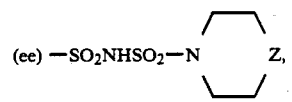

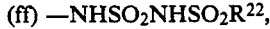

(dd) —$SO_2NHCO_2R^{22}$,

wherein Z is O, —$S(O)_x$, —$N(R^{11})$—, —$NCOR^{22}$, —$NSO_2R^{22}$, —$NCO_2R^{22}$ or —$NCON(R^4)R^{22}$;

(ff) —$NHSO_2NHSO_2R^{22}$,

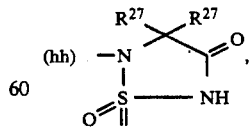

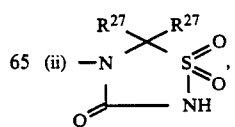

(jj) 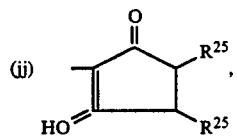

(kk) 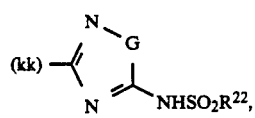

(ll) 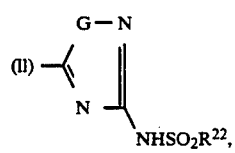

(mm) —SO$_2$NHSO$_2$—N<R$^4$/R$^9$, 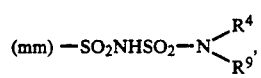

(nn) 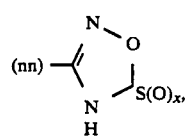

(oo) 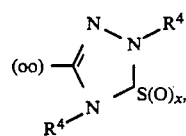

(pp) 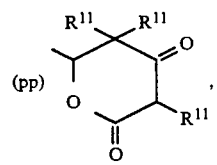

(qq) 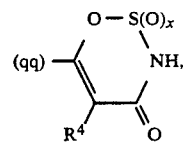

(rr) 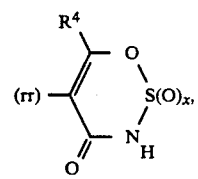

(ss) —N(R$^4$)—C(=O)—C(=O)—OH, 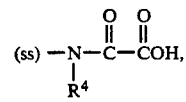

(tt) —NHSO$_2$R$^{22}$, 

(uu) —SO$_2$NHCON⟨ ⟩Z, or 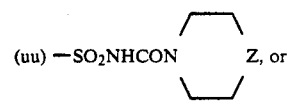

(vv) —SO$_2$NHCON⟨ ⟩(CH$_2$)$_n$; 

wherein
G is O or S:
wherein heteroaryl is are unsubstituted, monosubstituted or disubstituted five or six membered aromatic ring which can optionally contain from 1 to 3 heteroatoms selected from the group consisting of O, N or S,
wherein said ring is selected from the group consisting of pyridine pyrimidine pyrazine, triazine, furan, thiophene, oxazole, thiazole, imidazole, triazole, or thiadiazole, and
wherein the substituents are members selected from the group consisting of —OH, —SH, —C$_1$–C$_4$-alkyl, —C$_1$–C$_4$-alkoxy, —CF$_3$, halo (Cl, Br, F, I), —NO$_2$, —CO$_2$—CO$_2$-(C$_1$–C$_4$-alkyl), —NH$_2$, —NH(C$_1$–C$_4$-alkyl) and —N(C$_1$–C$_4$-alkyl)$_2$;

R$^{2a}$ and R$^{2b}$ are each independently
(a) H,
(b) halogen, (Cl, Br, I, F)
(c) NO$_2$,
(d) NH$_2$,
(e) C$_1$–C$_4$-alkylamino,
(f) di(C$_1$–C$_4$-alkyl)amino
(g) SO$_2$NHR$^9$,
(h) CF$_3$,
(i) C$_1$–C$_6$-alkyl,
(j) C$_1$–C$_6$-alkoxy,
(k) C$_1$–C$_6$-alkyl—S—,
(l) C$_2$–C$_6$-alkenyl,
(m) C$_2$–C$_6$-alkynyl;
(n) aryl as defined below,
(o) aryl(C$_1$–C$_4$-alkyl), wherein aryl is defined below;
(p) C$_3$–C$_7$-cycloalkyl;

R$^{3a}$ is
(a) H,
(b) halo,
(c) C$_1$–C$_6$-alkyl,
(d) C$_1$–C$_6$-alkoxy,
(e) C$_1$–C$_6$-alkoxyalkyl;

R$^{3b}$ is
(a) H,
(b) halo,
(c) NO$_2$,
(d) C$_1$–C$_6$-alkyl,
(e) C$_1$–C$_6$-acyloxy,
(f) C$_3$–C$_7$-cycloalkyl,
(g) C$_1$–C$_6$-alkoxy,
(h) —NHSO$_2$R$^4$,
(i) hydroxy(C$_1$–C$_4$-alkyl),
(j) aryl(C$_1$–C$_4$-alkyl), wherein aryl is defined below;
(k) C$_1$–C$_4$-alkylthio,
(l) C$_1$–C$_4$-alkyl sulfinyl,
(m) C$_1$–C$_4$-alkyl sulfonyl,
(n) NH$_2$,
(o) C$_1$–C$_4$-alkylamino,
(p) di(C$_1$–C$_4$-alkyl)amino,
(q) fluoro-C$_1$–C$_4$-alkyl-,
(r) —SO$_2$—NHR$^9$,
(s) aryl as defined below,
(t) furyl, (u) $CF_3$,
(v) $C_2$-$C_6$-alkenyl,
(w) $C_2$-$C_6$-alkynyl;

wherein aryl is phenyl or naphthyl optionally substituted with one or two substituents selected from the group consisting of halogen, $N(R^4)_2$, $CO_2R^4$, $C_1$-$C_4$-alkyl, $C_1$-$C_4$-alkoxy, $NO_2$, $CF_3$, $C_1$-$C_4$-alkylthio, OH,

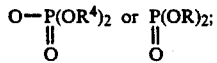

$R^4$ is H, aryl as defined above or straight chain or branched $C_1$-$C_6$ alkyl optionally substituted with aryl or heteroaryl as defined above;

$R^{4a}$ is aryl as defined above or straight chain or branched $C_1$-$C_6$-alkyl optionally substituted with aryl as defined above

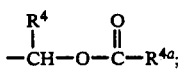

E is a single bond, $-NR^{13}(CH_2)_s-$, $-S(O)_x(CH_2)_s-$ where x is 0 to 2 and S is 0 to 5, $-CH(OH)-$, $-O-$, $CO-$;

$R^6$ is
(a) aryl as defined above optionally substituted with 1 or 2 substituents selected from the group consisting of halo $-O-C_1$-$C_4$-alkyl, $C_1$-$C_4$-alkyl, $-NO_2$, $-CF_3$, $-SO_2NR^9R^{10}$, $-S-C_1$-$C_4$-alkyl $-OH$, $-NH_2$, $C_3$-$C_7$-cycloalkyl, $C_3$-$C_{10}$-alkenyl;
(b) straight chain or branched $C_1$-$C_6$-alkyl, $C_2$-$C_5$-alkenyl or $C_2$-$C_5$-alkynyl each of which can be optionally substituted with a substituent selected from the group consisting of aryl as defined above, $C_3$-$C_7$-cycloalkyl, halo, $CF_3$, $CF_2CF_3$, $-NH_2$, $-NH(C_1$-$C_4$-alkyl), $-OR^4$—$N(C_1$-$C_4$-alkyl)$_2$, $-NH-SO_2R^4$, $-COOR^4$, $-SO_2NHR^9$; or
(c) heteroaryl, as defined above,
(d) $C_3$-$C_7$-cycloalkyl;
(e) perfluoro-$C_1$-$C_4$-alkyl,
(f) H;

$R^{8a}$ and $R^{8b}$ are independently
(a) H, provided they are not both H,
(b) $C_1$-$C_8$-alkyl substituted with a substituent selected from the group consisting of guanidino, $-O-COR^4$ -aryl, as defined above, -heteroaryl, as defined above, -tetrazol-5-yl, $-CONHSO_2R^{22}$, $-SO_2NH$-heteroaryl, wherein heteroaryl is defined above, $-SO_2NHCOR^{22}$, $-PO(OR^4)_2$, $-PO(OR^4)R^9$, $-SO_2NH-CN$, $-NR^1oCOOR^{22}$, morpholino, 4-$R^{22}$-piperazin-1-y, and 4-$COR^{22}$-piperazin-1-yl;
(c) $-CO$-aryl,
(d) -$C_3$-$C_7$-cycloalkyl,
(e) $-COOR^4$,
(f) $-SO_3H$,
(g) $-NR^4R^{22}$,
(h) $-NR^4COR^{22}$,
(i) $-NR^4COOR^{22}$,
(j) $-SO_2NR^4R^9$,
(k) $-NO_2$,
(l) $N(R^4)SO_2R^{22}$,
(m) $-NR^4CONR^4R^{22}$,

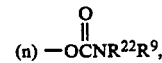

(o) -aryl or -heteroaryl as defined above,
(p) $-NHSO_2CF_3$,
(q) $-SO_2NH$-heteroaryl, wherein heteroaryl is defined above;
(r) $-SO_2NHCOR^{22}$,
(s) $-CONHSO_2R^{22}$,
(t) $-PO(OR^4)_2$,
(u) $-PO(OR^4)R^4$,
(v) -tetrazol-5-yl,
(w) $-CONH(tetrazol-5-yl)$,
(x) $-COR^4$,
(y) $-SO_2NHCN$,
(z) $-NR^4SO_2NR^4R^{22}$,
(aa) $-NR^4SO_2OR^{22}$,
(bb) $-CONR^4R^{22}$,

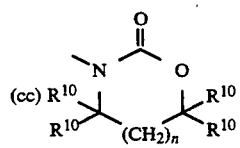

where n = 0 or 1.

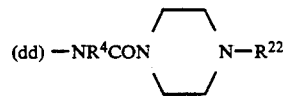

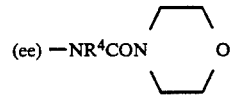

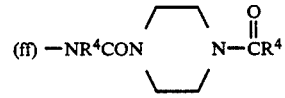

$R^9$ is H, $C_1$-$C_5$-alkyl, aryl or arylmethyl, wherein aryl is defined above;
$R^{10}$ is H, $C_1$-$C_4$-alkyl;
$R^{11}$ is H, $C_1$-$C_6$-alkyl, $C_1$-$C_4$-alkenyl, $C_1$-$C_4$-alkoxyalkyl, or

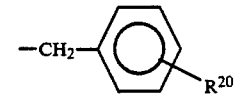

$R^{12}$ is $-CN$, $-NO_2$ or $-CO_2R^4$;
$R^{13}$ is H, $(C_1$-$C_4$-alkyl)CO—, $C_1$-$C_6$-alkyl, allyl, $C_3$-$C_6$-cycloalkyl, aryl or arylmethyl, wherein aryl is defend above;
$R^{14}$ is H, $C_1$-$C_8$-alkyl, $C_1$-$C_8$-perfluoroalkyl, $C_3$-$C_6$-cycloalkyl, aryl or arylmethyl, wherein aryl is defined above;
$R^{15}$ is H, $C_1$-$C_6$-alkyl;
$R^{16}$ is H, $C_1$-$C_6$-alkyl, $C_3$-$C_6$-cycloalkyl, aryl or arylmethyl, wherein aryl is defined above;
$R^{17}$ is $-NR^9R^{10}$, $-OR^{10}$, $-NHCONH_2$, $-NHCSNH_2$, $-NHSO_2-\langle\text{phenyl}\rangle-CH_3$ or $-NHSO_2-\langle\text{phenyl}\rangle$;

$R^{18}$ and $R^{19}$ are independently $C_1-C_4$-alkyl or taken together are $-(CH_2)_q-$ where q is 2 or 3;

$R^{20}$ is H, $-NO_2$, $-NH_2$, $-OH$ or $-OCH_3$;

$R^{21}$ is
  (a) aryl as defined above,
  (b) heteroaryl as defined above,
  (c) $C_1-C_4$-alkyl optionally substituted with a substituent selected from the group consisting of aryl as defined above, heteroaryl as defined above, $-OH$, $-NH_2$, $-NH(C_1-C_4$-alkyl), $-N(C_1-C_4$-alkyl)$_2$, $-CO_2R^{4a}$, halo, $-CF_3$;

$R^{22}$ is
  (a) aryl as defined above,
  (b) heteroaryl as defined above,
  (c) $C_3-C_7$-cycloalkyl,
  (d) $C_1-C_8$-alkyl optionally substituted with a substituent selected from the group consisting of aryl as defined above, heteroaryl as defined above, $-OH$, $-SH$, $C_1-C_4$-alkyl, $-O(C_1-C_4$-alkyl), $-S(C_1-C_4$-alkyl), $-CF_3$, halo (Cl, Br, F, I), $-NO_2$, $-CO_2H$, $CO_2$-($C_1-C_4$-alkyl), $-NH_2$, $-NH(C_1-C_4$-alkyl), $-N(C_1-C_4$-alkyl)$_2$, $-PO_3H_2$, $-PO(OH)(O-C_1-C_4$-alkyl); $-PO(OR^4)R^9$ or $-C_3-C_6$-cycloalkyl, or;
  (e) perfluoro-$C_1-C_4$-alkyl;

$R^{25}$ is
  (a) H,
  (b) aryl as defined above, or
  $C_1-C_6$-alkyl optionally substituted with aryl, F, Cl, Br, $-OH$, $-NH_2$, $-NH(C_1-C_4$-alkyl), $-N(C_1-C_4$-alkyl)$_2$, or $CF_3$;

$R^{26}$ is
  (a) aryl as defined above,
  (b) $C_1-C_6$-alkyl optionally substituted with aryl, F, Cl, Br, $-OH$, $-NH_2$, $-NH(C_1-C_4$-alkyl), $-N(C_1-C_4$-alkyl)$_2$, $CF_3$, $-COOR^4$, or CN,
  (c) $-OCH(R^4)-O-CO-R^{4a}$, or
  (d) $-OH$ or $-O-C_1-C_6$-alkyl wherein alkyl is as defined in (b);

$R^{27}$ is
  (a) H,
  (b) $C_1-C_6$-alkyl optionally substituted with aryl, as defined above F, Cl, Br, $-OH$, $-NH_2$, $-NH(C_1-C_4$-alkyl ), $-N(C_1-C_4$-alkyl)$_2$, $CF_3$, $-COOR^4$, or CN, or X is
  (a) a carbon-carbon single bond,
  (b) $-CO-$,
  (c) $-O-$,
  (d) $-S-$, (e) $-\underset{R^{13}}{N}-$, (f) $-\underset{R^{15}}{CON}-$, (g) $-\underset{R^{15}}{NCO}-$, (h) $-OCH_2-$,
(i) $-CH_2O)-$, (j) $-SCH_2-$,
(k) $-CH_2S-$,
(l) $-NHC(R^9)(R^{10})$,
(m) $-NR^9SO_2-$,
(n) $-SO_2NR^9-$,
(o) $-C(R^9)(R^{10})NH-$,
(p) $-CH=CH-$,
(q) $-CF=CF-$,
(r) $-CH=CF-$,
(s) $-CF=CH-$,
(t) $-CH_2CH_2-$,
(u) $-CF_2CF_2-$, (v) $-CH\overset{CH_2}{\underset{}{-}}CH-$ or $\overset{CH_2}{\underset{CH_2}{\diagdown C \diagup}}$, (w) $-\underset{}{\overset{OR^{14}}{CH}}-$, (x) $-\underset{}{\overset{OCOR^{16}}{CH}}-$, (y) $-\overset{NR^{17}}{\underset{}{C}}-$, or (z) $-\underset{}{\overset{R^{18}O \quad OR^{19}}{C}}-$ ;

and
r is 1 or 2.

2. A compound of claim 1 wherein:
M is a C atom;
J is $-C(O)-$;
K and L are connected together to form a 6 membered aromatic ring containing one N atom that is not at K and five C atoms which may be substituted at the carbon atoms with $R^{8a}$ and $R^{8b}$;
  (a) $-NH-SO_2CF_3$;
  (b) $-SO_2NH$-heteroaryl as defined above,
  (c) $-CH_2SO_21NH$-heteroaryl as defined above,
  (d) $-SO_2NH-CO-R^2$,
  (e) $-CH_2SO_2NH-CO-R^{22}$,
  (f) $-CONH-SO_2R^{22}$,
  (g) $-CH_2CONH-SO_2R^{22}$,
  (h) $-NHSO_2NHCO-R^{22}$,
  (i) $-NHCONHSO_2-R^{22}$,
  (j) $-SO_2NHCO_2R^{22}$,
  (k) $-SO_2NHCON^4R^{22}$,
  (l) $-COOH$ or,
  (m) $-$tetrazolyl;

$R^{2a}$ is H;
$R^{2b}$ is H, F, Cl, $CF_3$, $C_1-C_6$-alkyl, $C_2-C_6$-alkenyl, $C_2-C_6$-alkynyl, or aryl;
$R^{3a}$ is H;
$R^{3b}$ is H, F, Cl, $CF_3$, $C_1-C_4$-alkyl, $C_2-C_4$-alkenyl, $C_2-C_4$-alkynyl, $C_5-C_6$-cycloalkyl, $-COOCH_3$, $-COOC_2H_5$, $-SO_2-CH_3$, $NH_2$, $-N(C_1-C_4$-alkyl)$_2$ or $-NH-SO_2CH_3$;
E is a single bond, $-O-$ or $-S-$;
$R^6$ is
  (a) $C_1-C_5$ alkyl optionally substituted with a substituent selected from the group consisting of $C_3-C_5$-cycloalkyl, Cl, $CF_3$, $CCl_3$, $-O-CH_3$, $-OC_2H_5$, $-S-CH_3$, $-S-C_2H_5$, phenyl, or F;

(b) C₂-C₅-alkenyl or C₂-C₅-alkynyl; or,
(c) C₃-C₅-cycloalkyl;

R$^{8a}$ and R$^{8b}$ are independently
(a) H, provided they are not both H,
(b) C₁-C₈-alkyl substituted with OCOR$^{4a}$, or aryl;
(c) —NO₂, (d) $-\overset{R^4}{\underset{|}{N}}-\overset{O}{\overset{\|}{C}}-R^{22}$, (e) —CONR⁴R²², (f) $-NR^4-\overset{O}{\overset{\|}{C}}-O-R^{22}$, (g) —NR⁴—R²²,
(h) —CF₃,
(i) —CO₂R$^{4a}$,
(j) —CO-aryl
(k) —SO₂—NR⁴R⁹,
(l) —N(R⁴)SO₂R²²,
(m) aryl
(n) —NR⁴CONR⁴R²²,
(o) —N(R⁴)SO₂N(R⁴)R²²;

(p) 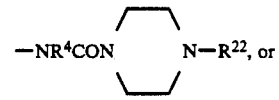 —NR⁴CON  N—R²², or (q) —NR⁴CON  N—CR⁴,
              ‖
              O (r) —N(R⁴)CON  O (s) heteroaryl X is a single bond;
r is one wherein aryl and heteroaryl are defined in claim 1.

3. A compound of claim 2 wherein:
R¹ is (a) —COOH,
(a) —NH—SO₂—CF₃,
(b) —SO₂NH-heteroaryl as defined above.
(c) —SO₂NH—CO—R²²,
(d) —CONH—SO₂R²²,
(e) —SO₂NHCO₂R²², or
(f) —SO₂NHCON⁴R²²,
(g) —COOH or
(h) —tetrazolyl:

E is a single bond;
r is one,
R²a, R$^{2b}$, R$^{3a}$ and R$^{3b}$ are each H, —C₁-C₆-alkyl, —C₂-C₆-alkenyl, —C₂-C₆-alkynyl, —Cl, —F, —NO₂, —CF₃;
R⁶ is —C₁-C₄-alkyl, -cyclopropyl, —CH₂CH₂CH₂CF₃, —CH₂CH₂CF₃, —C₂-C₅-alkenyl, -cyclopropylmethyl or methyl;
R$^{8a}$ and R$^{8b}$ are each independently H, —NO₂, —NR⁴R²², —NR⁴COOR²², —CH₂COOR$^{4a}$, NR⁴CONR⁴R²², CH₂OCO(C₁-C₄-alkyl), NR⁴COR²², CO₂R$^{4a}$, heteroayl, —CH₂Ph, —CONR⁴R²², —NR⁴CON  N—R²², or

—NR⁴CON  N—COR²² wherein aryl and heteroaryl are defined in claim 1.

4. A compound of claim 3 wherein:
R¹
(a) COOH,
(a) —SO₂NHCOR²²,
(b) —CONHSO₂R²²,
(c) —NHSO₂CF₃;
(d) —SO₂NHCO₂R²²,
(e) —SO₂NHCONR⁴R²²,
(f) —COOH, or
(g) —tetrazolyl;

R$^{2a}$, R$^{2b}$, and R$^{3a}$ and R$^{3b}$ each H, —C₁-C₄-alkyl, —Cl or F;

R⁶ is -n-propyl, ethyl, -n-butyl, -trans-2-butenyl, CH₂CH₂CF₃, —CH₂CH₂CH₂CF₃-cyclopropyl, -cyclopropylmethyl, or methyl;

R$^{8a}$ and R$^{8b}$ are each independently H, —NO₂, —NH₂, —NHCOCH₃, —NHCH₃, —N(CH₃)₂, —OCH₃, —COOH, —COOCH₃, —CH₂COOCH₃, —N(R⁴)CON(R⁴)₂, —N(R⁴)CO₂R²², —N(R⁴)COR²², —CH₂COOH, —N(R⁴)COR²², heteroaryl NHMe, CH₂Ph.

—NR⁴CON  N—R²², or

—NR⁴CON  NCOR²² wherein aryl and heteroaryl are defined in claim 1.

5. A compound of claim 1 wherein:
M is a C atom;
K is —C(O)—;
J and L are connected together to form a 6 membered aromatic ring containing one N atom that is not at J and five C atoms which may be substituted at the carbon atoms with R$^{8a}$ and R$^{8b}$;
R¹ is
(a) —NH—SO₂CF₃;
(b) —SO₂NH-heteroaryl as defined above,
(c) —CH₂SO₂NH-heteroaryl as defined above,
(d) —SO₂NH—CO—R²²,
(e) —CH₂SO₂NH—CO—R²²,
(f) —CONH—SO₂R²²,
(g) —CH₂CONH—SO₂R²²,
(h) —NHSO₂NHCO—R²²,
(i) —NHCONHSO₂—R²²,
(j) —SO₂NHCO₂R²²,
(k) —SO₂NHCONR⁴R²²,
(l) —COOH or,
(m) —tetrazolyl;
R²a is H;

$R^{2b}$ is H, F, Cl, $CF_3$, $C_1$-$C_6$-alkyl, $C_2$-$C_6$-alkenyl, $C_2$-$C_6$-alkynyl, or aryl;

$R^{3a}$ is H;

$R^{3b}$ is H, F, Cl, $CF_3$, $C_1$-$C_4$-alkyl, $C_2$-$C_4$-alkenyl, $C_2$-$C_4$-alkynyl, $C_5$-$C_6$-cycloalkyl, —$COOCH_3$, —$COO_2H_5$, —$SO_2$—$CH_3$, $NH_2$, —$N(C_1$-$C_4$-alkyl$)_2$ or —NH—$SO_2CH_3$;

E is a single bond, —O— or —S—;

$R^6$ is (a) $C_1$-$C_5$ alkyl optionally substituted with a substituent selected from the group consisting of $C_3$-$C_5$-cycloalkyl, Cl, $CF_3$, $CCl_3$, —O—$CH_3$, —$OC_2H_5$, —S—$CH_3$, —S—$C_2H_5$, phenyl, or F;

(b) $C_2$-$C_5$-alkenyl or $C_2$-$C_5$-alkynyl; or, (c) $C_3$-$C_5$-cycloalkyl;

$R^{8a}$ and $R^{8b}$ are independently (a) H, provided they are not both H, (b) $C_1$-$C_8$-alkyl substituted with $OCOR^{4a}$, or aryl;

(c) —$NO_2$, (d) 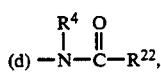—N—C—$R^{22}$, (e) —$CONR^4R^{22}$, (f) 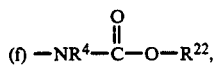—$NR^4$—C—O—$R^{22}$, (g) —$NR^4$—$R^{22}$, (h) —$CF_3$, (i) —$CO_2R^{4a}$, (j) —CO-aryl as defined above, (k) —$SO_2$—$NR^4R^9$, (l) —$N(R^4)SO_2R^{22}$, (m) aryl as defined above, (n) —$NR^4CONR^4R^{22}$, (o) —$N(R^4)SO_2N(R^4)R^{22}$, (p) —$NR^4CON$⟨ ⟩N—$R^{22}$, (q) 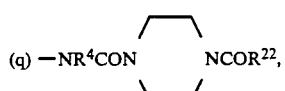—$NR^4CON$⟨ ⟩$NCOR^{22}$, (r) 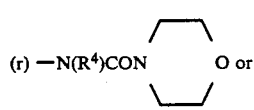—$N(R^4)CON$⟨ ⟩O or (s) heteroaryl X is a single bond;

r is one wherein aryl and heteroaryl are defined in claim 1.

6. A compound of claim 5 wherein:

$R^1$ is (a) —NH—$SO_2$—$CF_3$, (b) —$SO_2NH$-heteroaryl as defined above, (c) —$SO_2NH$—CO—$R^{22}$, (d) —$CONH$—$SO_2R^{22}$, (e) —$SO_2NHCO_2R^{22}$, (f) —$SO_2NHCONR^4R^{22}$;

(g) —COOH or (h) —tetrazolyl;

E is a single bond;

r is one, $R^{2a}$, $R^{2b}$, $R^{3a}$ and $R^{3b}$ are each H, —$C_1$-$C_6$-alkyl, —$C_2$-$C_6$-alkenyl, —$C_2$-$C_6$-alkynyl, —Cl, —F, —$NO_2$, —$CF_3$;

$R^6$ is —$C_1$-$C_4$-alkyl, -cyclopropyl, —$CH_2CH_2CH_2CF_3$, —$CH_2CH_2CF_3$, —$C_2$-$C_5$-alkenyl, -cyclopropylmethyl, or methyl;

$R^{8a}$ and $R^{8b}$ are each independently H, —$NO_2$, —$NR^4R^{22}$, —$NR^4COOR^{22}$, $NR^4ONR^4R^{22}$, $CH_2OCO(C_1$-$C_4$- alkyl), —$NR^4COR^{22}$, $CO_2R^{4a}$, heteroayl, —$CH_2Ph$, —$CONR^4R^{22}$,

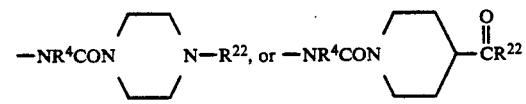—$NR^4CON$⟨ ⟩N—$R^{22}$, or —$NR^4CON$⟨ ⟩—$CR^{22}$

7. A compound of claim 6 wherein:

$R^1$ is (a) —$SO_2$—$NHCOR^{22}$, (b) —$CONHSO_2R^{22}$, (c) —$NHSO_2CF_3$, (d) —$SO_2NHCO_2R^{22}$, or (e) —$SO_2NHCONR^4R^{22}$;

(f) —COOH or (g) —tetrazolyl:

$R^{2a}$, $R^{2b}$, $R^{3a}$ and $R^{3b}$ are each H, —$C_1$-$C_4$-alkyl, —Cl or F;

$R^6$ is -n-propyl, ethyl, -n-butyl, -trans-2-butenyl, $CH_2CH_2CF_3$, —$CH_2CH_2CH_2CF_3$-cyclopropyl, -cyclopropylmethyl;

$R^{8a}$ and $R^{8b}$ are each independently H, —$NO_2$, —$NH_2$, —$NHCOCH_3$, —$N(CH_3)_2$, —COOH, —$COOCH_3$, —$CH_2OCOCH_3$, —$N(R^4)CON(R^4)_2$, —$N(R^4)CO_2R^{22}$, —$N(R^4)COR^{22}$, NHMe, $CH_2Ph$,

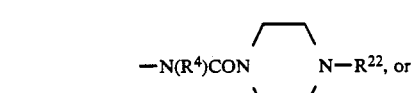—$N(R^4)CON$⟨ ⟩N—$R^{22}$, or

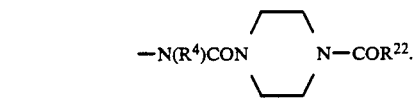—$N(R^4)CON$⟨ ⟩N—$COR^{22}$.

8. A compound of claim 7 which is:

2-Propyl-6-(N-benzoyl-N-butyl)amino-3-(2'-tetrazol-5-yl)biphen-4-yl) methyl]pyrido[3,2-d]-pyrimidin-4(3H)-one 2-Propyl-6-(2-pyridyl)3-[2'-(N-butyloxycarbonylsulfamido)biphen-4-yl) methyl]pyrido[3,2-d]-pyrimidin-4(3H)-one.

9. A compound of claim 1 wherein:

M is a C atom;

K is C=$NR^{22}$;

J and L are connected together to form a 6 membered aromatic ring containing one N atom that is not at J and five C atoms which may be substituted at the carbon atoms with $R^{8a}$ and $R^8$;

$R^1$ is (a) —NH—$SO_2CF_3$;

(b) —$SO_2NH$-heteroaryl as defined above, (c) —$CH_2SO_21NH$-heteroaryl as defined above, (d) —$SO_2NH$—CO—$R^{22}$, (e) —CH$_2$SO$_2$NH—CO—R$^{22}$,
(f) —CONH—SO$_2$R$^{22}$,
(g) —CH$_2$CONH—SO$_2$R$^{22}$,
(h) —NHSO$_2$NHCO—R$^{22}$,
(i) —NHCONHSO$_2$—R$^{22}$,
(j) —SO$_2$NHCO$_2$R$^{22}$, or
(k) —SO$_2$NHCONR$^4$R$^{22}$,
(l) —COOH or,
(m) —tetrazolyl;

R$^{2a}$ is H;
R$^{2b}$ is H, F, Cl, CF$_3$, C$_1$-C$_6$-alkyl, C$_2$-C$_6$-alkenyl, C$_2$-C$_6$-alkynyl, or aryl;
R$^{3a}$ is H;
R$^{3b}$ is H, F, Cl, CF$_3$, C$_1$-C$_4$-alkyl, C$_2$-C$_4$-alkenyl, C$_2$-C$_4$-alkynyl, C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$ or —NH—SO$_2$CH$_3$;
E is a single bond, —O— or —S—;
R$^6$ is
(a) C$_1$-C$_5$ alkyl optionally substituted with a substituent selected from the group consisting of C$_3$-C$_5$-cycloalkyl, Cl, CF$_3$, CCl$_3$, —O—CH$_3$, —OC$_2$H$_5$, —S—CH$_3$, —S—C$_2$H$_5$, phenyl, or F;
(b) C$_2$-C$_5$-alkenyl or C$_2$-C$_5$-alkynyl; or,
(c) C$_3$-C$_5$-cycloalkyl;

R$^{8a}$ and R$^{8b}$ are independently
(a) H,
(b) C$_1$-C$_8$-alkyl optionally substituted with OCOR$^{4a}$, or, aryl;
(c) —NO$_2$,

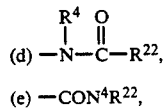

(e) —CON$^4$R$^{22}$,
(g) —NR$^4$R$^{22}$,
(h) —CF$_3$,
(i) —CO$_2$R$^{4a}$,
(j) —CO-aryl, as defined above,
(k) —SO$_2$—NR$^4$R$^9$,
(l) —N(R$^4$)SO$_2$R$^{22}$,
(m) aryl as defined above,
(n) —NR$^4$CONR$^4$R$^{22}$;
(o) —N(R$^4$)SO$_2$N(R$^4$)R$^{22}$;

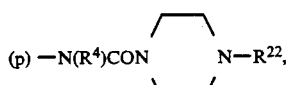

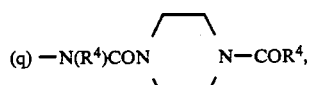

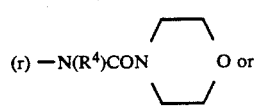

(s) heteroaryl;
X is a single bond;
r is one wherein aryl and heteroaryl are defined in claim 1.

10. A compound of claim 9 wherein:
R$^1$ is
(a) —COOH,
(a) —NH—SO$_2$—CF$_3$,
(b) —SO$_2$NH-heteroaryl as defined above.
(c) —SO$_2$NH—CO—R$^{22}$,
(d) —CONH—SO$_2$R$^{22}$,
(e) —SO$_2$NHCOR$^{22}$, or
(f) —SO$_2$NHCONR$^4$R$^{22}$;
(g) —COOH or
(h) —tetrazolyl:
E is a single bond;
r is one,
R$^{2a}$, R$^{2b}$, R$^{3a}$ and R$^{3b}$ are each H, —C$_1$-C$_6$-alkyl, —C$_2$-C$_6$-alkenyl, —C$_2$-C$_6$-alkynyl, —Cl, —F, —NO$_2$, —CF$_3$;
R$^6$ is —C$_1$-C$_4$-alkyl, -cyclopropyl, —CH$_2$CH$_2$CH$_2$CF$_3$, —CH$_2$CH$_2$CF$_3$, —C$_2$-C$_5$-alkenyl, -cyclopropylmethyl or methyl;
R$^{8a}$ and R$^{8b}$ are each independently H, —NO$_2$, —NR$^4$R$^{22}$, —NR$^4$COOR$^{22}$, NR$^4$CONR$^4$R$^{22}$, CH$_2$OCO(C$_1$-C$_4$- alkyl), —NR$^4$COR$^{22}$, CO$_2$R$^{4a}$, heteroayl, —CH$_2$Ph, —CONR$^4$R$^{22}$,

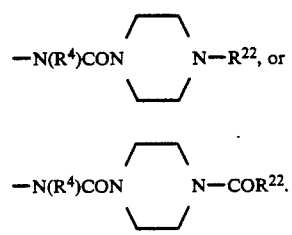

11. A compound of claim 10 wherein:
R$^1$ is
(a) —SO$_2$—NHCOR$^{22}$,
(b) —CONHSO$_2$R$^{22}$,
(c) —NHSO$_2$CF$_3$,
(d) —SO$_2$NHCO$_2$R$^{22}$,
(e) —SO$_2$NHCON$^4$R$^{22}$,
(f) —COOH or
(g) —tetrazolyl:
R$^{2a}$, R$^{2b}$, R$^{3a}$ and R$^{3b}$ are each H, —C$_1$-C$_6$-alkyl, —Cl or F;
R$^6$ is -n-propyl, ethyl, -n-butyl, -trans-2-butenyl, CH$_2$CH$_2$CF$_3$, —CH$_2$CH$_2$CH$_2$CF$_3$-cyclopropyl, -cyclopropylmethyl, or methyl;
R$^{8a}$ and R$^{8b}$ are each independently H, —NO$_2$, —NH$_2$, —NHCOCH$_3$, —N(CH$_3$)$_2$, —COOH, —COOCH$_3$, —CH$_2$OCOCH$_3$, —N(R$^4$)CON(R$^4$)$_2$, —N(R$^4$)CO$_2$R$^{22}$, —N(R$^4$)COR$^{22}$, NHMe, CH$_2$Ph.

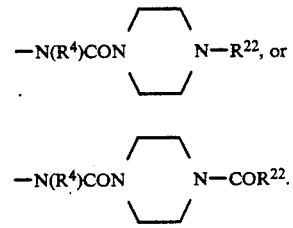

12. A pharmaceutical composition useful in the treatment of hypertension which comprises a pharmaceutically acceptable carrier and a pharmaceutically effective amount of a compound of claim 1.

13. A method of treating hypertension which comprises administering to a patient in need of such treatment a pharmaceutically effective amount of a compound of claim 1.

14. An ophthalmological formulation for the treatment of ocular hypertension comprising an opthalmologically acceptable carrier and an effective ocular antihypertensive amount of a compound of claim 1.

15. A method of treating ocular hypertension comprising administering to a patient in need of such treatment an effective ocular antihypertensive amount of a compound of claim 1.

* * * * *